US010828283B2

(12) United States Patent
Cory et al.

(10) Patent No.: US 10,828,283 B2
(45) Date of Patent: *Nov. 10, 2020

(54) TREATMENT OF HEPATITIS DELTA VIRUS INFECTION

(71) Applicant: Eiger BioPharmaceuticals, Inc., Palo Alto, CA (US)

(72) Inventors: David A. Cory, Palo Alto, CA (US); Ingrid Choong, Palo Alto, CA (US); Jeffrey S. Glenn, Palo Alto, CA (US)

(73) Assignee: Eiger Biopharmaceuticals, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/052,386

(22) Filed: Aug. 1, 2018

(65) Prior Publication Data

US 2019/0167646 A1   Jun. 6, 2019

Related U.S. Application Data

(63) Continuation of application No. 15/335,327, filed on Oct. 26, 2016, now Pat. No. 10,076,512, which is a continuation-in-part of application No. PCT/US2015/028933, filed on May 1, 2015.

(60) Provisional application No. 62/151,349, filed on Apr. 22, 2015, provisional application No. 62/073,413, filed on Oct. 31, 2014, provisional application No. 62/044,766, filed on Sep. 2, 2014, provisional application No. 61/987,315, filed on May 1, 2014, provisional application No. 62/251,026, filed on Nov. 4, 2015, provisional application No. 62/297,740, filed on Feb. 19, 2016, provisional application No. 62/321,623, filed on Apr. 12, 2016.

(51) Int. Cl.

| A61K 31/427 | (2006.01) |
| A61K 31/4545 | (2006.01) |
| A61K 9/00 | (2006.01) |
| A61K 38/21 | (2006.01) |
| A61K 9/14 | (2006.01) |
| A61K 47/60 | (2017.01) |

(52) U.S. Cl.
CPC .......... *A61K 31/427* (2013.01); *A61K 9/0053* (2013.01); *A61K 9/146* (2013.01); *A61K 31/4545* (2013.01); *A61K 38/21* (2013.01); *A61K 38/212* (2013.01); *A61K 47/60* (2017.08)

(58) Field of Classification Search
CPC .................. A61K 31/427; A61K 31/4545
See application file for complete search history.

(56) References Cited

U.S. PATENT DOCUMENTS

| 4,695,623 A | 9/1987 | Stabinsky |
| 4,897,471 A | 1/1990 | Stabinsky |
| 5,382,657 A | 1/1995 | Karasiewicz et al. |
| 5,541,206 A | 7/1996 | Kempf et al. |
| 5,648,497 A | 7/1997 | Kempf et al. |
| 5,951,974 A | 9/1999 | Gilbert et al. |
| 5,981,709 A | 11/1999 | Greenwald et al. |
| 6,169,096 B1 | 1/2001 | Venet et al. |
| 6,365,600 B1 | 4/2002 | End et al. |
| 6,420,387 B1 | 7/2002 | Venet et al. |
| 6,627,223 B2 | 9/2003 | Percel et al. |
| 6,734,194 B2 | 5/2004 | End et al. |
| 6,743,805 B2 | 6/2004 | End et al. |
| 6,838,467 B2 | 1/2005 | End |
| 6,927,040 B2 | 8/2005 | Sheppard et al. |
| 7,038,032 B2 | 5/2006 | Sheppard et al. |
| 7,135,170 B2 | 11/2006 | Klucher et al. |
| 7,148,459 B2 | 12/2006 | Williford et al. |
| 7,157,559 B2 | 1/2007 | Brady et al. |
| 7,183,416 B2 | 2/2007 | Chemburkar et al. |
| 7,253,183 B2 | 8/2007 | End et al. |
| 7,511,027 B2 | 3/2009 | Casey et al. |
| 7,595,174 B2 | 9/2009 | Brady et al. |
| 7,759,092 B2 | 7/2010 | Zamost et al. |
| 7,968,315 B2 | 6/2011 | Zamost et al. |
| 8,211,670 B2 | 7/2012 | Zamost et al. |
| 8,293,726 B2 * | 10/2012 | Habib ............... A61K 31/575 514/182 |
| 8,759,027 B2 | 6/2014 | Zamost et al. |
| 8,980,245 B2 | 3/2015 | Ho |
| 9,096,556 B2 | 8/2015 | Reddy et al. |
| 10,076,512 B2 | 9/2018 | Cory et al. |
| 2003/0114471 A1 | 6/2003 | Venet et al. |
| 2003/0181355 A1 | 9/2003 | Glenn |

(Continued)

FOREIGN PATENT DOCUMENTS

| JP | 2002-533435 A | 10/2002 |
| JP | 2004-510762 A | 4/2004 |

(Continued)

OTHER PUBLICATIONS

Abbas, Z. et al. *Management of Hepatitis Delta: Need for Novel Therapeutic Options.* World Journal of Gastroenterology, vol. 21, No. 32. Published Aug. 28, 2015. 6 pages.

Blanchet et al., "Use of FDA approved therapeutics with hNTCP metabolic inhibitory properties to impair the HDV lifecycle", Antiviral Research, Elsevier Masson, 2014, pp. 111-115.

Ghosal et al., Identification of Human Liver Cytochrome P450 Enzymes Responsible for the Metabolism of Lonafarnib (Sarasar), Drug Metabolism and Disposition, vol. 34, No. 4, Jan. 27, 2006, pp. 628-635.

(Continued)

Primary Examiner — Gina C Justice
(74) Attorney, Agent, or Firm — Kilpatrick Townsend & Stockton LLP

(57) ABSTRACT

Methods of reducing hepatitis delta virus (HDV) viral loads in a patient are provided. In some embodiments, the method comprises treating the patient with lonafarnib-ritonavir cotherapy. In some embodiments, the method further comprises treating the patient with an interferon.

20 Claims, 36 Drawing Sheets

(56) References Cited

U.S. PATENT DOCUMENTS

| | | |
|---|---|---|
| 2006/0111398 A1 | 5/2006 | Fourie |
| 2007/0287664 A1 | 12/2007 | Ralston et al. |
| 2008/0021078 A1 | 1/2008 | Tidmarsh et al. |
| 2009/0142393 A1 | 6/2009 | Xu et al. |
| 2010/0029667 A1 | 2/2010 | Ketner et al. |
| 2011/0105557 A1 | 5/2011 | End et al. |
| 2011/0313009 A1 | 12/2011 | Tidmarsh et al. |
| 2013/0102526 A1 | 4/2013 | Bernstein et al. |
| 2013/0165371 A1 | 6/2013 | Dobry et al. |
| 2013/0193598 A1 | 8/2013 | Friesen et al. |
| 2014/0017314 A1 | 1/2014 | Beyerinck et al. |
| 2014/0210117 A1 | 7/2014 | Friesen et al. |
| 2014/0220141 A1 | 8/2014 | Giardiello et al. |
| 2015/0028503 A1 | 1/2015 | Beyerinck et al. |
| 2015/0273354 A1 | 10/2015 | Dobry et al. |
| 2015/0374827 A1 | 12/2015 | Miller et al. |
| 2017/0042862 A1 | 2/2017 | Cory et al. |
| 2018/0110734 A1 | 4/2018 | Gosselin et al. |
| 2018/0338993 A1 | 11/2018 | Cory et al. |

FOREIGN PATENT DOCUMENTS

| | | | |
|---|---|---|---|
| JP | 2009-530382 A | | 8/2009 |
| JP | 2012-111775 A | | 6/2012 |
| JP | 2012-524753 A | | 10/2012 |
| JP | 2014-509630 A | | 4/2014 |
| JP | 2014-523878 A | | 9/2014 |
| JP | 2014-530874 A | | 11/2014 |
| WO | 97-01349 | A1 | 1/1997 |
| WO | 97-23478 | A1 | 7/1997 |
| WO | 97-31641 | A1 | 9/1997 |
| WO | 00-39082 | A2 | 7/2000 |
| WO | 2005-097165 | A2 | 10/2005 |
| WO | 2005/117864 | A1 | 12/2005 |
| WO | 2007-012033 | A2 | 1/2007 |
| WO | 2007-013944 | A2 | 2/2007 |
| WO | 2007-041713 | A1 | 4/2007 |
| WO | 2008-137692 | A1 | 11/2008 |
| WO | 2009-042960 | A1 | 4/2009 |
| WO | 2011/088126 | A2 | 7/2011 |
| WO | 2012-131061 | A1 | 10/2012 |
| WO | 2012-164575 | A2 | 12/2012 |
| WO | 2012-174220 | A1 | 12/2012 |
| WO | 2013-024494 | A2 | 2/2013 |
| WO | 2013-034927 | A1 | 3/2013 |
| WO | 2013-059638 | A1 | 4/2013 |
| WO | 2013-116720 | A1 | 8/2013 |
| WO | 2014-071231 | A1 | 5/2014 |
| WO | 2015/168648 | A1 | 11/2015 |
| WO | 2016-090107 | A2 | 6/2016 |
| WO | 2016-172342 | A1 | 10/2016 |
| WO | 2016/172342 | A1 | 12/2016 |
| WO | 2017/079009 | A1 | 5/2017 |

OTHER PUBLICATIONS

Hanrahan et al., A Phase II Study of Lonafarnib (SCH66336) in Patients With Chemo refractory, Advanced Squamous Cell Carcinoma of the Head and Neck, American Journal of Clinical Oncology, vol. 32, No. 3, Jun. 2009, pp. 274-279.

Heidrich, B. et al. "Treatment options for hepatitis delta virus infections", Curr Infect Dis Rep Feb. 2013, 15(1):31-8.

International Search Report and Written Opinion received in International Patent Application No. PCT/US16/58937, filed Oct. 26, 2016. Received Mar. 2, 2017. 18 pages.

International Application No. PCT/US2015/028933, International Preliminary Report on Patentability dated Nov. 10, 2016, 5 pages.

International Application No. PCT/US2015/028933, International Search Report and Written Opinion dated Jul. 15, 2015, 5 pages.

Koh et al., Oral prenylation inhibition with lonafarnib in chronic hepatitis D infection: a proof-of-concept randomized, double-blind, placebo-controlled phase 2A trial, Lancet Infect Dis, vol. 15, No. 10, Oct. 2015, 8 pages.

Li et al., Effect of hepatitis B virus infection on human P450 3 A4, Nal Med J China, vol. 86, No. 38, Oct. 17, 2006, pp. 2703-2706.

Liaw, Hepatitis flares and hepatitis B e antigen seroconversion: Implication in anti-hepatitis B virus therapy, Journal of Gastroenterology and Hepatology, vol. 18, 2003, pp. 246-252.

Noureddin, M. et al. "Hepatitis delta: epidemiology, diagnosis and management 36 years after discovery", Curr Gastroenterol Rep, Jan. 2014; 16 (1): 365.

Wedemeyer et al., Epidemiology, pathogenesis and management of hepatitis D: update and challenges ahead, Nature Reviews Gastroenterology and Hepatology, vol. 7, Jan. 2010, pp. 31-40.

Yurdaydin, C. et al. *Optimizing the Prenylation Inhibitor Lonafarnib Using Ritonavir Boosting in Patients with Chronic Delta Hepatitis.* Journal of Hepatology, vol. 62, Supplement 2. Published Apr. 2015. Retrieved from the internet on Dec. 17, 2016. Retrieved from the internet: URL<http://www.journal-of-hepatology.eu/article/S0168-8278(15)30137-9/abstract>.4 pages.

Yu, L., et al., "Amorphous pharmaceutical solids: stabilization", Advanced Drug Delivery Reviews, Volume preparation, characterization and 48,2001, p. 27-42.

International Search Report and Written Opinion dated Jul. 26, 2016 in International Patent Application No. PCT/US2016/028651, 15 pages.

International Preliminary Report on Patentability dated Oct. 24, 2017 in International Patent Application No. PCT/US2016/028651, 7 pages.

International Search Report and Written Opinion dated Feb. 23, 2016 in International Patent Application No. PCT/US2015/063674, 12 pages.

International Preliminary Report on Patentability dated Jun. 6, 2017 in International Patent Application No. PCT/US2015/063674, 9 pages.

Erhardt, A., et al., "Treatment of chronic hepatitis delta with pegylated interferon-α2b", Liver international: official journal of the International Association for the Study of the Liver, vol. 26, No. 7, Sep. 2006, p. 805-810, DOI:10.1111/j.1478-3231.2006.01279.x.

Canini, L., et al., "Understanding hepatitis delta virus dynamics and antiviral efficacy of the prenylation inhibitor lonafarnib", AASLD Abstracts, Hepatology, vol. 60, No. 4, Oct. 2014, p. 317A-321A.

Bordier, B.B., et al., "In vivo antiviral efficacy of prenylation inhibitors against hepatitis delta virus", The Journal of Clinical Investigation, vol. 112, No. 3, Aug. 1, 2003, p. 407-414, DOI:10.1172/JC1200317704.

Bordier, B.B., et al. "A prenylation inhibitor prevents production of infectious hepatitis delta virus particles", J. Virol., vol. 76, Issue 20, Oct. 2002, p. 10465-10472, DOI:10.1128/jvi.76.20.10465-10472.2002.

Extended European Search Report dated Oct. 13, 2017 in European Patent Application No. 15785846.5, 9 pages.

Replacement Supplemental Extended European Search Report dated Nov. 24, 2017 in European Patent Application No. 15785846.5, 8 pages.

Erba, H.P., et al. "Four different regimens of farnesyltransferase inhibitor tipifarnib in older, untreated acute myeloid leukemia patients: North American Intergroup Phase II study SWOG S0432", Leukemia Research, vol. 38, Issue 3, Mar. 2014, p. 329-333, DOI:https://doi,orgi10.1016/j.leukres2013.12.001.

Extended European Search Report dated Apr. 26, 2018 in European Patent Application No. 15865819.5, 8 pages.

International Preliminary Report on Patentability dated May 8, 2018 in International Patent Application No. PCT/US2016/058937, 8 pages.

Glenn, J., et al. "Use of a Prenylation Inhibitor as a Novel Antiviral Agent", Journal of Virology, vol. 72, Issue 11, Nov. 1998, p. 9303-9306, DOI:10.1128/Jvi.72.11.9303-9306.1998.

Velasco, M., et al. "Resolution of Chronic Hepatitis B after Ritonavir Treatment in an HIV-Infected Patient," The New England Journal of Medicine, vol. 340, No. 22, 1999, p. 1765-1766.

Extended European Search Report dated Dec. 7, 2018 in European Patent Application No. 16783855.6, 4 pages.

Hu, Q. et al., "Highly efficient miniaturized coprecipitation screening (MiCoS) for amorphous solid dispersion formulation develop-

(56) References Cited

OTHER PUBLICATIONS ment," International Journal of Pharmaceutics, vol. 450, Issues 1-2, Jun. 25, 2013, p. 53-62, DOI:https://doi.org/10.1016/j.ijpharm.2013.04.040.

Tho, I., et al. "Formation of nano/micro-dispersions with improved dissolution properties upon dispersion of ritonavir melt extrudate in aqueous media", European Journal of Pharmaceutical Sciences, vol. 40, Issue 1, Apr. 2010, p. 25-32, DOI:https://doi.org/10.1016/j.ejps.2010.02.003.

Osborn, B. L., et al. "Pharmacokinetic and Pharmacodynamic Studies of a Human Serum Albumin-Interferon-α Fusion Protein in Cynomolgus Monkeys", the Journal of Pharmacology and Experimental Therapeutics, vol. 303, No. 2, year 2002, p. 540-548, DOI:https://doi.org/10.1124/jpet.102.037002.

Limdi, J.K., et al. "Evaluation of abnormal liver function tests", Postgraduate Medical Journal, vol. 79, Issue 932, year 2003, p. 307-312, DOI:10.1136/pmj.79.932.307.

Lucia, M.B., et al. "HIV-Protease Inhibitors Contribute to P-Glycoprotein Efflux Function Defect in Peripheral Blood Lymphocytes From HIV-Positive Patients Receiving HAART", JAIDS (Journal of Acquired Immune Deficiency Syndromes), vol. 27, Issue 4, Aug. 1, 2001, p. 321-330.

Miller, M.M., et al. "The role of dolutegravir in the management of HIV infections", Infection and Drug Resistance, vol. 8, Feb. 19, 2015, p. 19-29, DOI:https://doi.org/10.2147/Idr.S58706.

Otto, J.C., et al. "The Hepatitis Delta Virus Large Antigen Is Farnesylated Both in Vitro and in Animal Cells", the Journal of Biological Chemistry, vol. 271, No. 9, Mar. 1, 1996, p. 4569-4572, DOI:10.1074/jbc.271.9.4569.

Lau, D.T., et al., "Lamivudine for chronic delta hepatitis", Hepatology, vol. 30, Issue 2, Aug. 1999, p. 546-549, DOI:https://doi.org/10.1002/hep.510300217.

Liu, Y.P., et al. "Rapid and quantitative detection of hepatitis B virus", World Journal of Gastroenterology, vol. 21, Issue 42, Nov. 14, 2015, p. 11954-11963, DOI:10.3748/wjg.v21.i42.11954.

Karatayli, E., et al. "A one step real time PCR method for the quantification of hepatitis delta virus RNA using an external armored RNA standard and intrinsic internal control.", Journal of Clinical Virology, vol. 60, Issue 1, May 2014, p. 11-15, DOI:10.1016/j.jcv.2014.01.021.

Bergmeyer, H.U., et al. "Approved recommendation (1985) on IFCC methods for the measurement of catalytic concentration of enzymes", J. Clin. Chem. Clin. Biochem., vol. 24, No. 7, Jan. 1986, p. 481-495.

Glenn, J.S., et al. "Identification of a prenylation site in delta virus large antigen" Science, vol. 256, Issue 5061, May 29, 1992, p. 1331-1333, DOI:10.1126/science.1598578.

Zhang, F.L., et al. "Protein Prenylation: Molecular Mechanisms and Functional Consequences", Annual Review of Biochemistry, vol. 65, Jul. 1996, p. 241-269, DOI:10.1146/annurev.bi.65.070196.001325.

Masci, P., et al. "New and modified interferon alfas: Preclinical and clinical data", Current Oncology Reports, vol. 5, Apr. 2003, p. 108-113, DOI:https://doi.org/10.11107/s11912-003-0097-4.

Kodani, M., et al., "One-step real-time PCR assay for detection and quantitation of hepatitis D virus RNA", Journal of Virological Methods, vol. 193, Issue 2, Nov. 2013, p. 531-535, DOI:10.1016/j.jviromet.2013.07.033.

List A.F., et al., "Phase !study of continuous oral administration of lonafarnib (Sarasar) in patients with advanced hematologic malignancies", Blood, vol. 100, year 2002, p. 789a.

Koh, C., et al., "Prenylation inhibition with lonafarnib decreases hepatitis D levels in humans," Hepatology, Assld Abstracts, Abstract No. 1860, vol. 60, No. 4, Oct. 2014, p. 1092A-1093A.

Bedossa, P., et al., "Intraobserver and Interobserver Variations in Liver Biopsy Interpretation in Patients with Chronic Hepatitis C", Hepatology, vol. 20, Issue 1, Jul. 1994, p. 15-20, DOI:https://doi.org/10.1002/hep.1840200104.

Brunt, E., "Grading and staging the histopathological lesions of chronic hepatitis: The Knodell histology activity index and beyond" Hepatology, vol. 31, Issue 1, Dec. 30, 2003, p. 241-246, DOI:https://doi.org/10.1002/hep.510310136.

Chudy, M., et al. "Collaborative study to establish a World Health Organization international standard for hepatitis D virus RNA for nucleic acid amplification technique (NAT)-based assays", World Health Organization, Oct. 2013, 29 pages.

Hill, a., et al. "How much ritonavir is needed to boost protease inhibitors? Systematic review of 17 dose-ranging pharmacokinetic trials", AIDS, vol. 23, Issue 17, Nov. 13, 2009, p. 2237-2245, DOI:10.1097/QAD.0b013e328332c3a5.

Saldanha, J., et al. "An international collaborative study to establish a World Health Organization international standard for hepatitis B virus DNA nucleic acid amplification techniques", Vox Sanguinis, vol. 80, Issue 1, Jan. 2001, p. 63-71, DOI:10.1046/j.1423-0410.2001.00003.x.

Tong, W., et al., "Identification of unstable metabolites of Lonafarnib using liquid chromatography-quadrupole time-of-flight mass spectrometry, stable isotope incorporation and ion source temperature alteration", Journal of Mass Spectrometry, vol. 41, Issue 11, Nov. 2006, p. 1430-1441, DOI:10.1002/jms.1114.

Ning, L., "Pharmaceutics", Planned Textbook for Pharmacy and Bioengineering in Colleges and Universities, No. 186643, Dec. 31, 2007, p. 273-276.

* cited by examiner

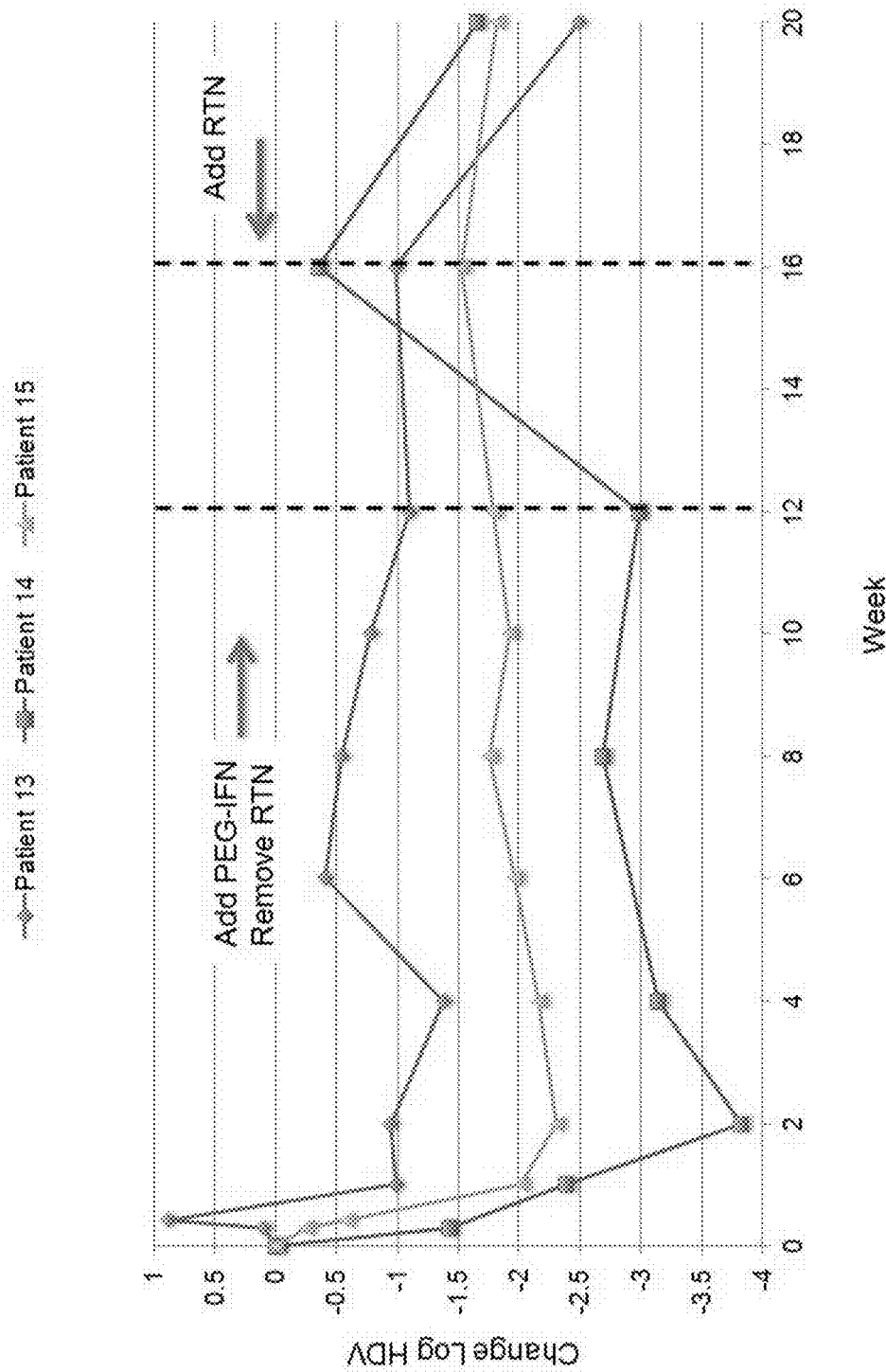

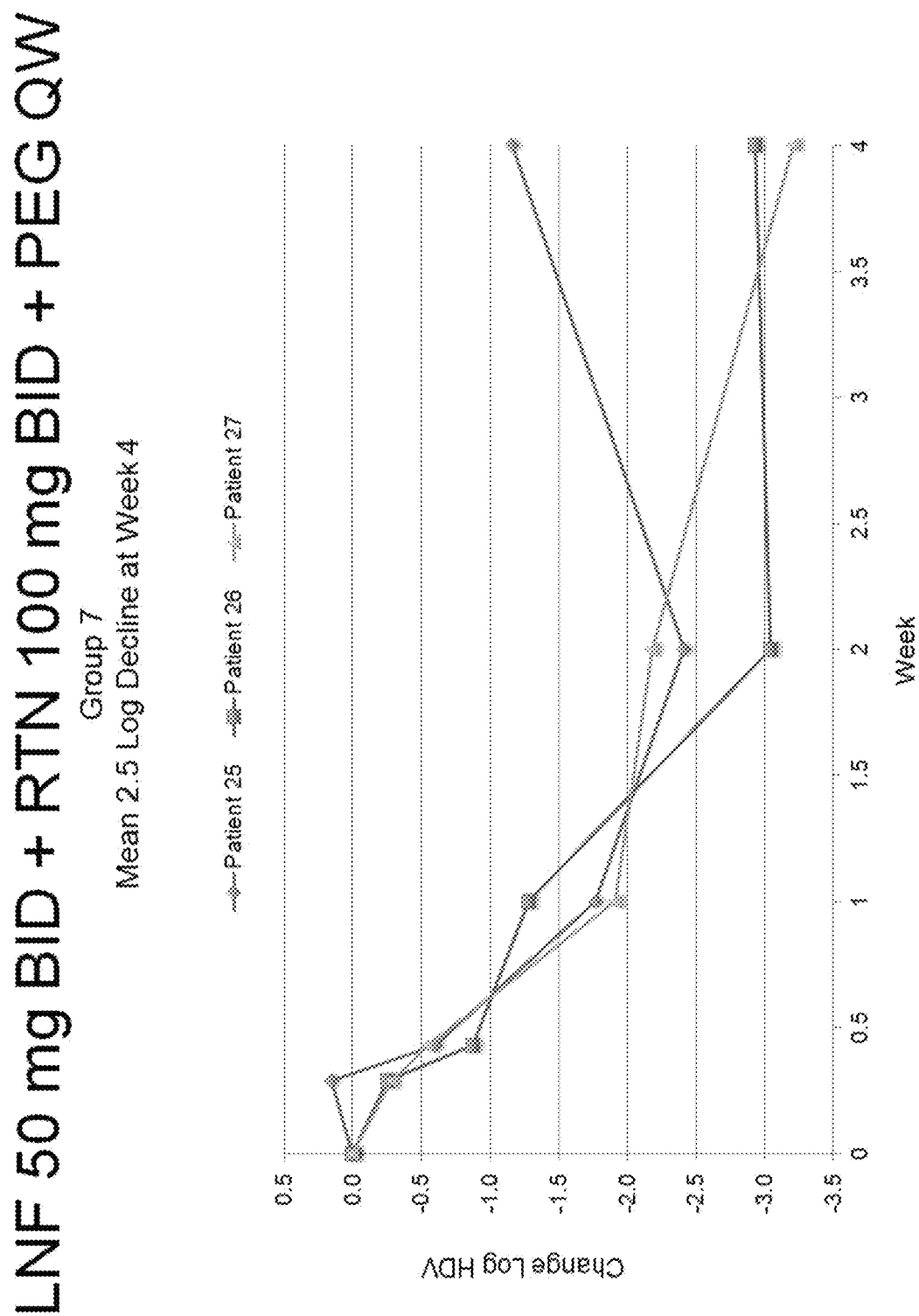

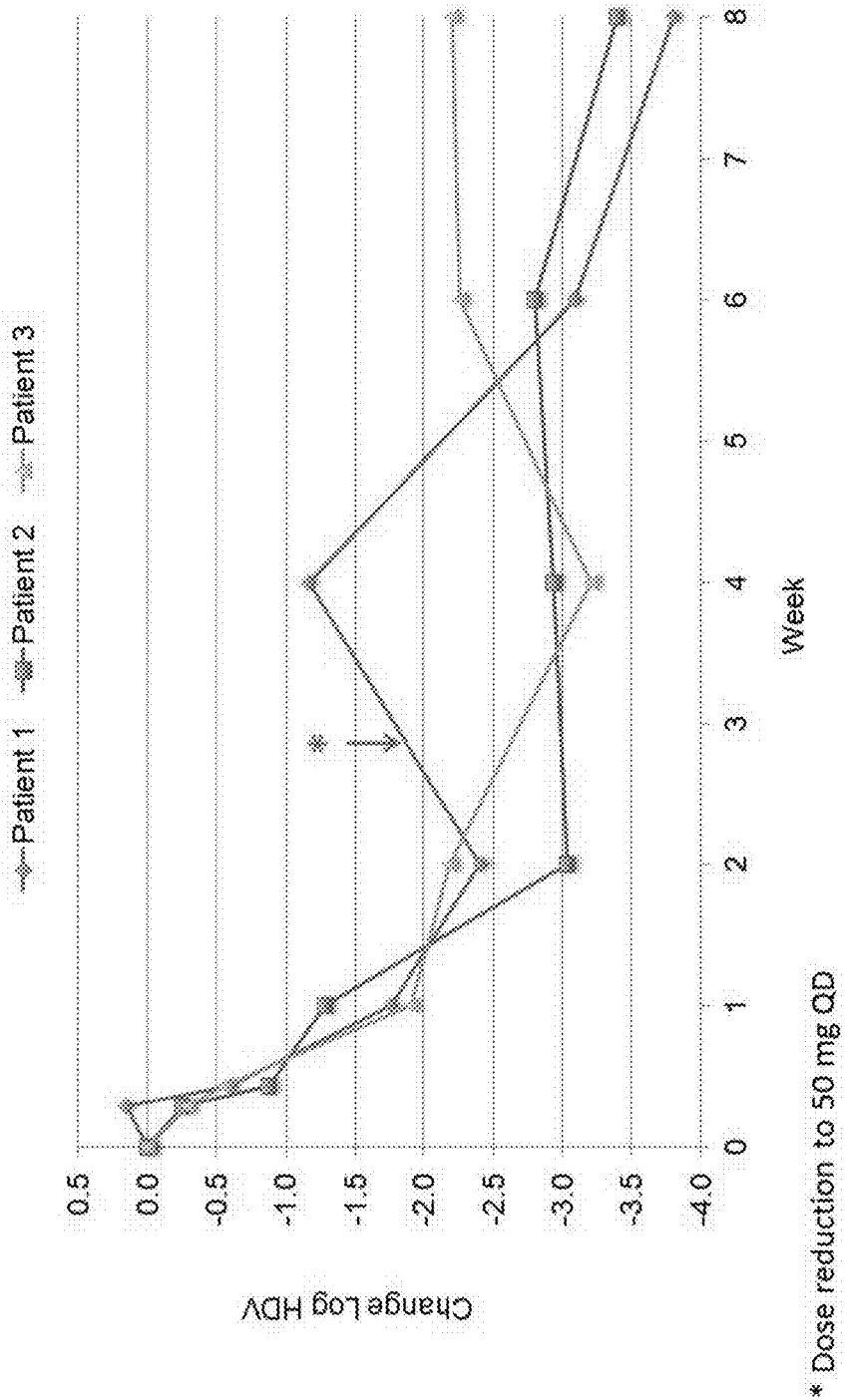

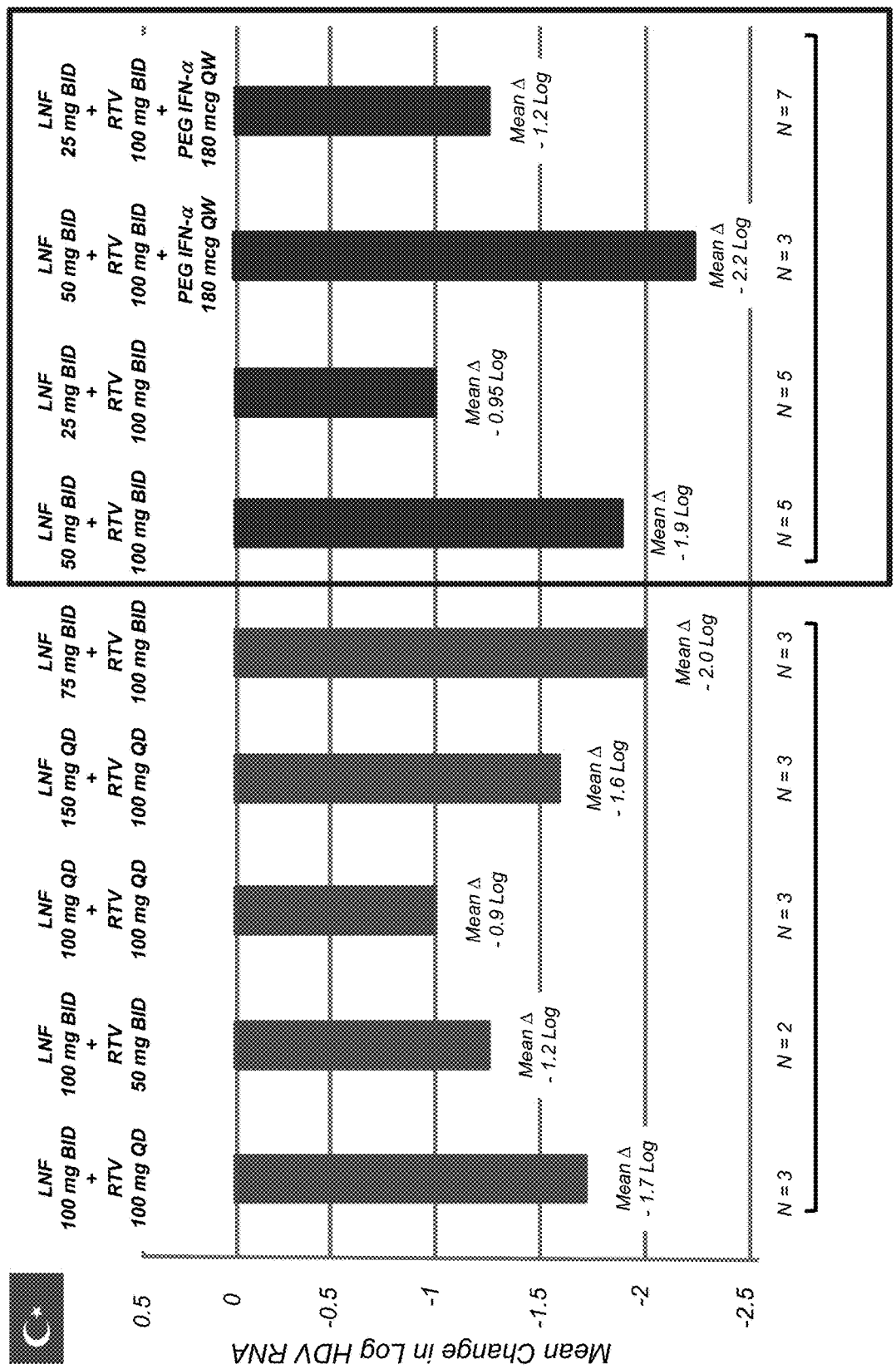

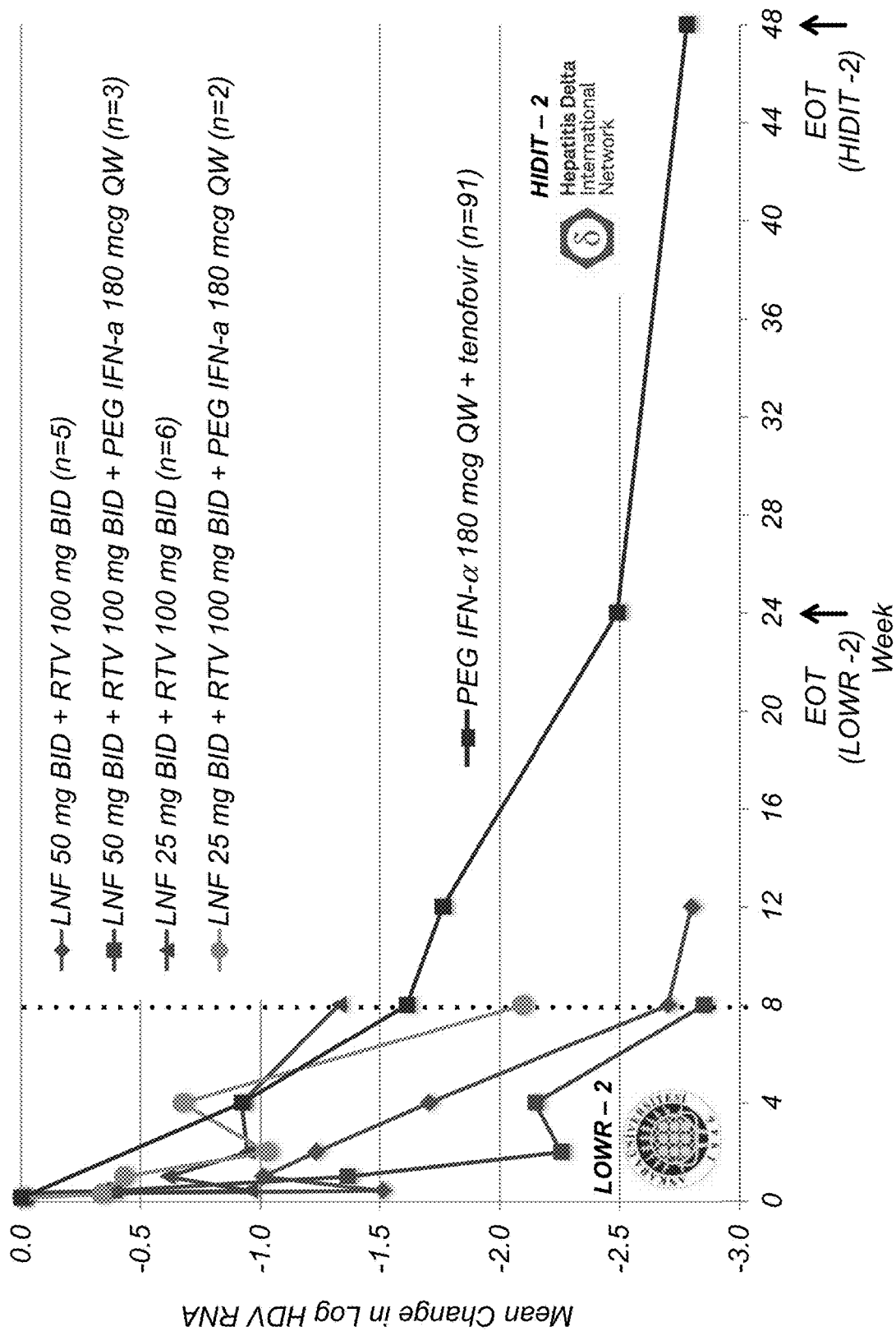

FIG. 24
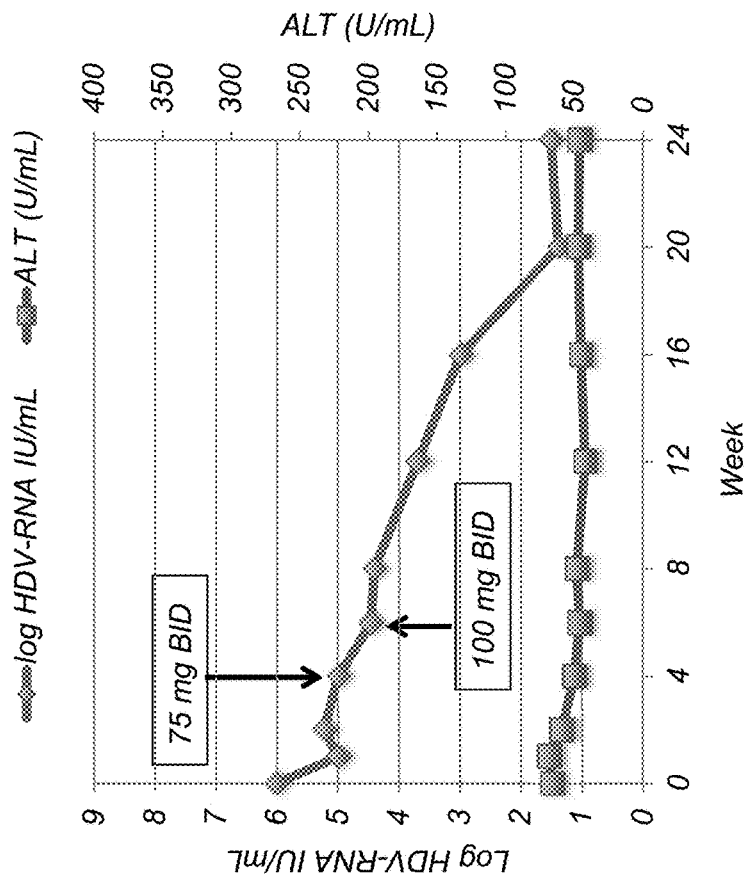
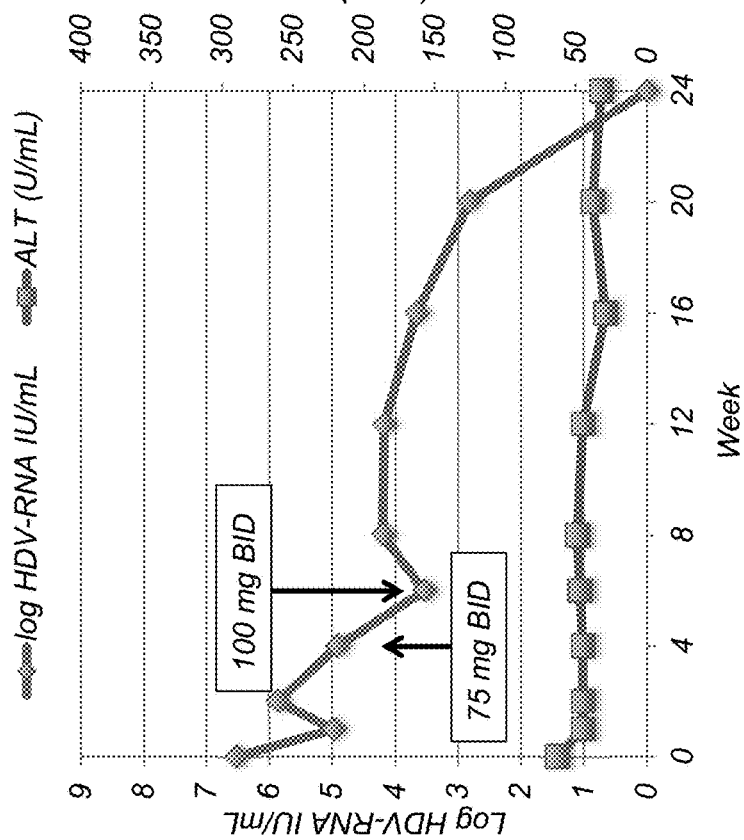

TREATMENT OF HEPATITIS DELTA VIRUS INFECTION

CROSS-REFERENCE TO RELATED APPLICATIONS

This application is a continuation of U.S. patent application Ser. No. 15/335,327, filed Oct. 26, 2016, which is a continuation-in-part of International Application No. PCT/US2015/028933, filed May 1, 2015, which claims priority to U.S. Provisional Application Nos. 61/987,315, filed May 1, 2014, 62/044,766, filed Sep. 2, 2014, 62/073,413, filed Oct. 31, 2014, and 62/151,349, filed Apr. 22, 2015, the contents of each of which are incorporated by reference herein. U.S. patent application Ser. No. 15/335,327 also claims priority to U.S. Provisional Application Nos. 62/251,026, filed Nov. 4, 2015, 62/297,740, filed Feb. 19, 2016, and 62/321,623, filed Apr. 12, 2016, the contents of each of which are incorporated by reference herein. This application is also related to U.S. Provisional Application No. 62/150,721, filed Apr. 21, 2015, U.S. Provisional Application No. 62/153,815, filed Apr. 28, 2015, and International Application No. PCT/US2016/028651, filed Apr. 21, 2016, the contents of each of which are incorporated by reference herein.

FIELD OF INVENTION

The present invention provides methods for treating viral hepatitis resulting from hepatitis delta virus (HDV) infection, and so relates to the fields of chemistry, medicinal chemistry, medicine, molecular biology, and pharmacology.

BACKGROUND OF THE INVENTION

Hepatitis delta virus (HDV) causes the most severe form of viral hepatitis, and there is no effective medical therapy (see Lau, 1999, Hepatology 30:546-549). HDV always presents as a co-infection with hepatitis B virus (HBV), and a co-infected patient is much more likely to die of complications of viral infection than a patient infected with HBV alone.

The HDV large delta antigen protein contains a CXXX box rendering it a substrate for prenylation (see Zhang and Casey, 1996, Annu. Rev. Biochem. 65:241-269) by the prenyl lipid farnesyltransferase (see Glenn et al., 1992, Science 256:1331-1333, and Otto and Casey, 1996, J. Biol. Chem. 271:4569-4572). Farnesylation of proteins catalyzed by FTase is an essential step in processing a variety of proteins and occurs by transfer of the farnesyl group of farnesyl pyrophosphate to a cysteine at the C-terminal tetrapeptide of a protein in a structural motif sometimes referred to as the CAAX box. Further post-translational modifications of a farnesylated protein, including proteolytic cleavage at the cysteine residue of the CAAX box and methylation of the cysteine carboxyl, generally follow farnesylation. Molecular genetic experiments demonstrated that specific mutation of the prenylation site in large delta antigen prevents both its prenylation and HDV particle formation (see Glenn et al., 1992, supra; also see Glenn et al., 1998 J. Virol. 72(11): 9303-9306; also see Bordier et al., 2002 J. Virol. 76(20): 10465-10472. There continues to be an ongoing need for agents to treat HDV infection.

BRIEF SUMMARY OF THE INVENTION

In one aspect, methods are provided for treating hepatitis delta virus (HDV) infection by oral administration of lonafarnib in combination with a CYP3A4 inhibitor (e.g., ritonavir or cobicistat). In one aspect, methods are provided for treating HDV infection by oral administration of lonafarnib at a dose of about 25 mg BID or 50 mg BID, in combination with ritonavir administered at 100 mg BID or 100 mg QD. In one aspect, methods are provided for treating HDV infection by oral administration of lonafarnib at a dose of about 25 mg QD or BID, 50 mg QD or BID, or about 75 mg QD or BID, in combination with ritonavir administered QD or BID at a therapeutically effective dose. In some embodiments, methods are provided for treating HDV infection by oral administration of lonafarnib at a dose of about 25 mg QD or BID, 50 mg QD or BID, or about 75 mg QD or BID, in combination with ritonavir administered QD or BID at a therapeutically effective dose and further in combination with an interferon (e.g., unpegylated or pegylated interferon alpha or interferon lambda) administered QW at a therapeutically effective dose.

In another aspect, methods of reducing HDV viral load in a human patient are provided. In some embodiments, the method comprises treating the patient with lonafarnib-ritonavir co-therapy for at least 30 days. In some embodiments, the patient has a chronic HDV infection. In some embodiments, the method comprises treating the patient with lonafarnib, ritonavir, and an interferon (e.g., unpegylated or pegylated interferon alpha or interferon lambda) for at least 30 days. In some embodiments, the method comprises treating the patient with lonafarnib-ritonavir co-therapy for at least 30 days, wherein the patient has a baseline viral load of at least $10^5$ IU/mL serum before the initiation of treatment, and treatment results in a reduction of viral load to less than $10^3$ IU/mL serum.

In some embodiments, the method comprises administering (e.g., orally administering) lonafarnib at a daily dose in the range of 50 mg to 150 mg. In some embodiments, lonafarnib is administered at a daily dose of 50 mg. In some embodiments, lonafarnib is administered at a daily dose of 100 mg. In some embodiments, lonafarnib is administered at a dose of 25 mg BID. In some embodiments, lonafarnib is administered at a dose of 50 mg QD. In some embodiments, lonafarnib is administered at a dose of 50 mg BID. In some embodiments, lonafarnib is administered at a dose of 75 mg QD. In some embodiments, lonafarnib is administered at a dose of 75 mg BID.

In some embodiments, the patient is treated with lonafarnib-ritonavir co-therapy for at least 60 days. In some embodiments, the patient is treated with lonafarnib-ritonavir co-therapy for at least 90 days. In some embodiments, the patient is treated with lonafarnib-ritonavir co-therapy for at least one year.

In one embodiment the patient receiving lonafarnib-ritonavir co-therapy receives lonafarnib at a daily dose of 50 mg/day to 150 mg/day, or at a daily dose of 50 mg/day to 100 mg/day, for example, 25 mg/day, 50 mg/day, 75 mg/day, or 100 mg/day, preferably wherein each administration of lonafarnib is no more than 75 mg, e.g., 25 mg or 50 mg; and ritonavir at a daily dose of 100 mg/day-200 mg/day, preferably wherein each administration of ritonavir is no more than 100 mg.

In one embodiment, the patient may receive 75 mg lonafarnib BID and 100 mg ritonavir BID.

In one embodiment, the patient may receive 50 mg lonafarnib BID and 100 mg ritonavir BID.

In one embodiment, the patient may receive 25 mg lonafarnib BID and 100 mg ritonavir BID.

In one embodiment, the patient may receive 75 mg lonafarnib BID and 100 mg ritonavir QD.

In one embodiment, the patient receives a daily dose of 100 mg lonafarnib and 200 mg ritonavir. For example, the patient may receive 50 mg lonafarnib BID and 100 mg ritonavir BID.

In one embodiment, the patient receives a daily dose of 75 mg lonafarnib and 100 mg ritonavir. For example, the patient may receive 75 mg lonafarnib QD and 100 mg ritonavir QD.

In one embodiment, the patient receives a daily dose of 50 mg lonafarnib and 100 mg ritonavir. For example, the patient may receive 50 mg lonafarnib QD and 100 mg ritonavir QD.

In one embodiment, the patient receives a daily dose of 50 mg lonafarnib and 200 mg ritonavir. For example, the patient may receive 25 mg lonafarnib BID and 100 mg ritonavir BID.

In some embodiments, in the treatment methods described herein, the lonafarnib and the ritonavir are administered together in a single unit dose form. In some embodiments, the unit dose form comprises amorphous lonafarnib. In some embodiments, the unit dose form comprises lonafarnib (e.g., amorphous lonafarnib), ritonavir, and a co-polymer. In some embodiments, the co-polymer is povidone.

In some embodiments, in the treatment methods described herein, the lonafarnib and the ritonavir are administered at about the same time as separate unit dose forms.

In some embodiments, in the treatment methods described herein, the lonafarnib and the ritonavir are administered together in a liquid formulation containing both lonafarnib and ritonavir.

In one embodiment, the patient receives oral lonafarnib at a dose of 50 mg/day, 75 mg/day, or 100 mg/day, administered BID or QD and oral ritonavir at a daily dose of 100 mg/day administered BID or QD, for example 100 mg/day, where the treatment results in a serum lonafarnib concentration greater than 2,000 ng/mL, preferably greater than 4,000 ng/mL, more preferably in the range of about 3,500 ng/mL to about 7,500 ng/mL.

In one embodiment, the patient receives oral lonafarnib at a daily dose of 50 mg/day, 75 mg/day, or 100 mg/day, administered BID or QD, optionally with a boosting agent, where the treatment results in a serum lonafarnib concentration greater than 2,000 ng/mL, preferably greater than 4,000 ng/mL, more preferably in the range of about 3,500 ng/mL to about 7,500 ng/m L.

In some embodiments, the patient has a baseline viral load of at least $10^4$ HDV RNA copies per mL serum before treatment, and treatment results in a viral load of less than $10^2$ HDV RNA copies per mL serum. In some embodiments, the patient has a baseline viral load of at least $10^7$ HDV RNA copies per mL serum before treatment, and treatment results in a viral load of less than $10^5$ HDV RNA copies per mL serum.

In some embodiments, wherein treatment results in a viral load of less than $10^2$ HDV RNA copies per mL serum, the patient receives an additional course of treatment of lonafarnib-ritonavir co-therapy for 30 days, and the viral load remains at less than $10^2$ HDV RNA copies per mL serum after the additional course of treatment.

In some embodiments, the treatment further comprises administering an interferon. In some embodiments, the interferon is interferon alpha or interferon lambda. In some embodiments, the interferon is a pegylated interferon. In some embodiments, the interferon is pegylated interferon alpha-2a or pegylated interferon lambda-1a.

In some embodiments, lonafarnib and ritonavir or a similar boosting agent, optionally in combination with an interferon, are administered to the patient in a course of therapy extending at least 30 days, more often at least 60 days or at least 90 days, even more often at least 120 days, sometimes for at least 150 days, and sometimes for at least 180 days. In some embodiments, lonafarnib and ritonavir or a similar boosting agent are administered to the patient in a course of therapy extending at least 6 months, at least 9 months, at least 12 months, at least 15 months, at least 18 months, at least 24 months, or longer. In some embodiments, dosing will be discontinued after virus levels have decreased to below 3 log HDV RNA copies/mL (below 1,000 copies/mL) or below the level of detection for a period of time (such as 1 to 3 months or longer).

In some embodiments the therapeutic approaches disclosed herein result in HDV RNA levels below 1,000 copies/mL serum or below 1,000 IU/mL serum, and in some cases may remain at the low level for at least one month. In some embodiments, after the HDV RNA level is determined to be below the threshold level (e.g., below 1,000 copies/mL serum or below 1,000 IU/mL serum), the lonafarnib-ritonavir co-therapy is continued.

In some embodiments the therapeutic approaches disclosed herein result in HDV RNA levels below 100 copies/mL serum or below 100 IU/mL serum and in some cases may remain at the low level for at least one month. In some embodiments, after the HDV RNA level is determined to be below the threshold level (e.g., below 100 copies/mL serum or below 100 IU/mL serum), the lonafarnib-ritonavir co-therapy is continued.

In some embodiments the therapeutic approaches disclosed herein result in HDV RNA levels that are below the level of detection and in some cases may remain at the low level for at least one month. In some embodiments, after the HDV RNA level is determined to be below the threshold level (e.g., below the level of detection), the lonafarnib-ritonavir co-therapy is continued.

In some embodiments the patient has a baseline viral load of at least $10^5$ HDV RNA copies per mL serum before the initiation of treatment, and treatment results in a reduction of viral load to less than $10^2$ HDV RNA copies per mL serum.

In some embodiments the patient has a baseline viral load of at least $10^5$ IU/mL serum before the initiation of treatment, and treatment results in a reduction of viral load to less than $10^2$ IU/mL serum.

In some embodiments, after the patient is determined to have a viral load of less than $10^2$ HDV RNA copies per mL serum (or, alternatively, less than $10^2$ IU/mL serum), treatment with lonafarnib-ritonavir co-therapy continues for at least 30 days.

In some embodiments, prior to the initiation of treatment, the patient has a baseline viral load of at least $10^7$ HDV RNA copies per mL serum (or, alternatively, less than $10^7$ IU/mL serum), and treatment results in a viral load of less than $10^5$ HDV RNA copies per mL serum (or, alternatively, less than $10^5$ IU/mL serum).

In some embodiments, the therapeutic approaches disclosed herein comprise administering lonafarnib at a first dose followed by administering lonafarnib at a second dose, wherein the second dose is lower than the first dose. In some embodiments, the therapeutic approaches disclosed herein comprise an escalating dosage regimen comprising administering lonafarnib at a first dose for a first treatment period and then administering lonafarnib at a second dose that is higher than the first dose for a second treatment period. In some embodiments, the patient receives lonafarnib at a first dose of 25 mg BID for the first treatment period followed by lonafarnib at a second dose of 50 mg BID for the second treatment period. In some embodiments, the therapeutic approach comprises administering the lonafarnib at a first dose for a first treatment period and then administering lonafarnib at a second dose that is higher than the first dose for a second treatment period if the patient does not experiences unacceptable gastrointestinal side effects during the first treatment period, or administering the lonafarnib at a first dose for a first treatment period and then administering lonafarnib at a second dose that is lower than the first dose for a second treatment period if the patient experiences unacceptable gastrointestinal side effects during the first treatment period.

In another aspect, methods for inducing immune reactivation in a patient infected with HDV and HBV are provided. In some embodiments, the method comprises administering lonafarnib at a total daily dose in the range of 50 mg to 150 mg for at least 12 weeks and/or until a hepatitis flare is observed. In some embodiments, the hepatitis flare is accompanied by a transient increase in the patient's HBV viral load. In some embodiments, the method comprises administering lonafarnib-ritonavir co-therapy in which ritonavir is administered at a total daily dose of 100-200 mg. Following immune reactivation, HDV viral load may be reduced by at least 2 log, by at least 3 log, or reduced to an undetectable level.

In one embodiment, inducing immune reactivation in a patient infected with HDV and HBV involves administering lonafarnib at a first dose followed by administering lonafarnib at a second dose, wherein the second dose is lower than the first dose. For example, in some cases the first dose is administered for at least 8 weeks and the second dose is administered for at least 2 weeks, and optionally at least 4 weeks. In some cases the first dose of lonafarnib is 50 mg BID and the second dose of lonafarnib is 50 mg QD. In some cases the first dose of lonafarnib and the second dose of lonafarnib are administered in combination with ritonavir at a dose of 100 mg BID.

In another aspect, lonafarnib-ritonavir co-therapy, as described herein, is stopped after a period of from 10-24 weeks of treatment, and lonafarnib-ritonavir co-therapy is not administered to the patient for at least 4 weeks. In some embodiments, lonafarnib-ritonavir co-therapy is stopped after a period of 10 to 14 weeks of treatment, or the lonafarnib-ritonavir co-therapy is stopped at 12 weeks of treatment.

In some embodiments, the therapeutic approaches disclosed herein comprise the step of detecting the occurrence of a hepatitis flare, and/or the step of detecting a transient increase of at least 3 log in the patient's hepatitis B virus (HBV) viral load. In some embodiments, the hepatitis flare is characterized by an abrupt elevation of serum alanine aminotransferase (ALT) to a level over 200 U/L. In some embodiments, the hepatitis flare is characterized by an abrupt elevation of serum alanine aminotransferase (ALT) to a level over 800 U/L. In some embodiments, therapy is discontinued within 25 weeks (e.g., within 20 weeks or within 12 weeks) following a hepatitis flare. In some embodiments, therapy is stopped at 12 weeks of treatment. In some embodiments, therapy is stopped after a period of 10 to 14 weeks of treatment. In some embodiments, wherein the therapy is stopped after a period of treatment (e.g., after a period of from 10-24 weeks of treatment, after a period of 10-14 weeks of treatment, or at 12 weeks of treatment), the therapy (e.g., lonafarnib-ritonavir co-therapy) is not administered to the patient for at least 4 weeks, e.g., at least 8 weeks, at least 12 weeks, or longer. In some embodiments, therapy is stopped prior to detecting the occurrence of the hepatitis flare and/or prior to detecting the transient increase.

In yet another aspect, methods for reducing HBV viral load in a patient infected with HBV and HDV are provided. In some embodiments, the patient has a chronic HBV infection and the course of treatment results in a reduction of the patient's HBV viral load compared to the baseline level at the initiation of treatment. In one approach, the method involves administering lonafarnib at a total daily dose in the range of 50 mg to 150 mg for at least 12 weeks, and optionally administering lonafarnib and ritonavir, and detecting a reduction of at least 1 log in HBV viral load. In some cases treatment results in an at least 2 log reduction of HBV viral load. In some cases the patient is not being treated with antiviral nucleotide or nucleoside analogs. In some embodiments, the patient is also treated by administration of interferon, which may be pegylated interferon lambda, and which may be administered at a dose of 120 mcg QW or 180 mcg QW.

In yet another aspect, a method of reducing hepatitis delta virus (HDV) viral load in a human patient with a chronic HDV infection, is provided, in which the patient receives lonafarnib-interferon co-therapy for at least 30 days, where the co-therapy includes oral administration of lonafarnib at a total daily dose in the range of 50 mg to 150 mg and oral administration of interferon lambda-1a at a total weekly dose in the range of 120 mcg to 180 mcg. Exemplary lonafarnib doses are 25 mg BID and 50 mg BID. In certain embodiments the interferon lambda-1a is pegylated interferon lambda-1a.

In one aspect, prior to the initiation of oral administration of lonafarnib and ritonavir, patient is prophylactically treated with at least one, and typically a combination of at least two GI modifying agents (one or more of an anti-emetic agent, an anti-diarrheal, and an antacid).

In another aspect, the GI modifying agents are administered at the same time as lonafarnib and ritonavir, and lonafarnib is administered as a delayed release formulation, and does not release until after the GI modifying agents begin take effect.

In still another aspect, unit dose forms comprising lonafarnib and ritonavir are provided. In some embodiments, the unit dose form is formulated for oral administration. In some embodiments, the unit dose form comprises lonafarnib and ritonavir in a ratio of about 1:2 (w/w) or about 1:4 (w/w), wherein the unit dose form is formulated for oral administration. In some embodiments, the unit dose form comprises lonafarnib in an amount from about 25 mg to about 100 mg and ritonavir in an amount of from about 50 mg to about 100 mg. In some embodiments, the unit dose form comprises amorphous lonafarnib. In some embodiments, the unit dose form comprises 25 mg amorphous lonafarnib and 100 mg ritonavir. In some embodiments, the unit dose form comprises 50 mg amorphous lonafarnib and 100 mg ritonavir. In some embodiments, the unit dose form comprises an admixture of lonafarnib and ritonavir, a multiparticulate formulation, or a bilayer formulation. In some embodiments, the unit dose form further comprises a co-polymer. In some embodiments, the co-polymer is selected from the group consisting of hydroxypropyl cellulose, hydroxypropyl methylcellulose, hypromellose phthalate, polyvinylpyrrolidone-vinylacetate copolymer, hypromellose-acetate-succinate, and mixtures thereof. In some embodiments, the co-polymer is not povidone. In some embodiments, the co-polymer is povidone. In some embodiments, the povidone is povidone K30. In some embodiments, the unit dose form is formulated as a capsule or a tablet. In some embodiments, one or both of the lonafarnib and the ritonavir are formulated for immediate release. In some embodiments, one or both of the lonafarnib and the ritonavir are formulated for controlled release.

In another aspect, liquid formulations comprising lonafarnib and ritonavir are provided. In some embodiments, the liquid formulation comprises lonafarnib and ritonavir at a ratio of 1:4 or 1:2.

In still another aspect, pharmaceutical packages comprising unit dose forms of lonafarnib and ritonavir are provided.

These and other aspects and embodiments of the invention are described in more detail below.

BRIEF DESCRIPTION OF THE DRAWINGS

FIG. 6A graphically illustrates changes in HDV RNA viral titers from a normalized baseline in patients treated with lonafarnib and ritonavir at doses described in Example 5 for a period of 28 days. FIG. 6B graphically illustrates changes in HDV RNA viral titers in patients treated with lonafarnib and ritonavir at doses described in Example 5 for a period of 56 days. FIG. 6C graphically illustrates changes in HDV RNA viral titers in patients treated with lonafarnib and ritonavir at doses described in Example 5 for a period of 84 days.

FIG. 12. Changes in HDV RNA viral titers in patients treated with lonafarnib, ritonavir and interferon using the combinations, doses, and schedule shown in the figure and described in Example 6.

FIG. 13. Changes in HDV RNA viral titers in patients treated with lonafarnib, ritonavir and interferon using the combinations, doses, and schedule shown in the figure and described in Example 7.

FIG. 14. Changes in HDV RNA viral titers in patients treated with lonafarnib, ritonavir and interferon using the combinations, doses, and schedule shown in the figure and described in Example 8.

FIG. 15A-15B. Changes in HDV RNA viral titers in patients treated with lonafarnib-ritonavir cotherapy with or without pegylated interferon-α as described in Example 12. (A) Changes in HDV RNA viral titers measured after 4 weeks. (B) Changes in HDV RNA viral titers measured after 8 weeks.

FIG. 16. Changes in HDV RNA viral titers at various timepoints for patients treated with lonafarnib-ritonavir cotherapy with or without pegylated interferon-α as described in Example 12.

FIG. 24. Time course of HDV RNA levels (copies/mL) and ALT levels (U/L) in patients treated with lonafarnib/ritonavir co-therapy as described in Example 14.

In FIGS. 26-30, the limit of quantification (LOQ) for the assay for HDV is 3.2 log IU/mL and the LOQ for the assay for HBV is 2 log IU/mL. Accordingly, for HDV, measurements graphed as >0 log and <3.2 log should be considered indicative of the presence of HDV at a concentration more than zero IU/mL and less than 3.2 log IU/mL, but are not indicative of a precise quantity within this range. Likewise, for HBV, measurements graphed as >0 log and <2 log should be considered indicative of the presence of HBV at a concentration more than zero IU/mL and less than 2 log IU/mL, but are not indicative of a precise quantity within that range.

FIG. 27. Post-treatment ALT flare in patient A-001-1 treated with 300 mg BID lonafarnib as described in Example 15, showing HDV-RNA negativity and ALT normalization following ALT flare and suppression of HDV RNA and HBV DNA.

FIG. 28. Post-treatment ALT flare in patient A-002-3 treated with 100 mg BID lonafarnib in combination with 50 mg BID ritonavir for about 10 weeks followed by lonafarnib (150 mg QD) and ritonavir (50 mg BID) for 2 weeks, as described in Example 15, showing HDV-RNA negativity and ALT normalization following ALT flare and HDV RNA and HBV DNA decline in parallel.

FIG. 29. Post-treatment ALT flare in patient A-002-14 treated with 75 mg BID lonafarnib in combination with 100 mg BID ritonavir for weeks 1-12, 50 mg BID lonafarnib in combination with 100 mg BID ritonavir for weeks 13-24, and pegylated interferon alpha from weeks 16-24, as described in Example 15, showing HDV-RNA and ALT decline following ALT flare and suppression of HDV RNA and HBV DNA.

FIG. 30. Post-treatment ALT flare in patient A-002-23 treated with 50 mg BID lonafarnib in combination with 100 mg BID ritonavir as described in Example 15 showing HDV-RNA decline and ALT normalization following ALT flare and suppression of HDV RNA and HBV DNA.

DETAILED DESCRIPTION OF THE INVENTION

Figure 1:
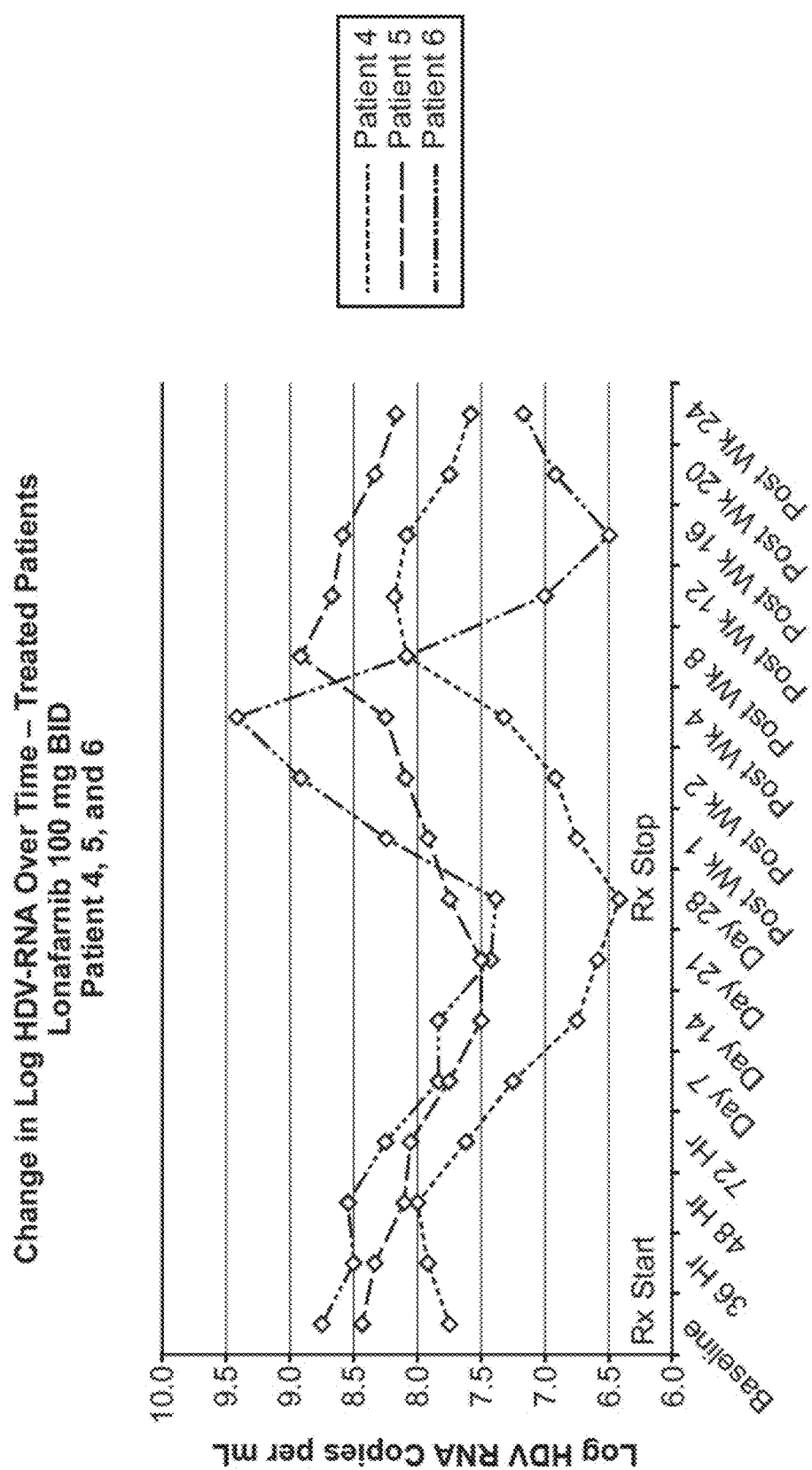
FIG. 1. Time course of HDV RNA levels (copies/mL) in patients treated with 100 mg lonafarnib BID for 28 days. See Example 1.

This detailed description of the invention is divided into sections for the convenience of the reader. As will be apparent to those of skill in the art upon reading this disclosure, each of the individual embodiments described and illustrated herein has discrete components and features which may be readily separated from or combined with the features of any of the other several embodiments (whether described in the same or different sections of this disclosure) without departing from the scope or spirit of the present disclosure. Any recited method can be carried out in the order of events recited or in any other order that is logically possible. Embodiments of the present disclosure will employ, unless otherwise indicated, techniques of synthetic organic chemistry, biochemistry, biology, molecular biology, recombinant DNA techniques, pharmacology, and the like, which are within the skill of the art. Such techniques are explained fully in the literature. This disclosure is not limited to particular embodiments described, and the embodiment of the invention in practice may, of course, vary from that described herein.

I. Definitions

The terminology used herein is for the purpose of describing particular embodiments only, and is not intended to be limiting, because the scope of the present invention will be limited only by the appended claims. Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings unless a contrary intention is apparent. In some cases, terms with commonly understood meanings are defined herein for clarity and/or for ready reference, and the inclusion of such definitions herein should not be construed as representing a substantial difference over the definition of the term as generally understood in the art.

Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

All numerical designations, e.g., pH, temperature, time, concentration, and molecular weight, including ranges, are approximations which are varied (+) or (−) by increments of 0.1 or 1.0, as appropriate. It is to be understood, although not always explicitly stated that all numerical designations are preceded by the term "about."

HDV levels are generally presented using login units, following the normal conventions of virology. HDV RNA levels may be presented in units of "RNA copies per mL" or as "International Units (IU) per mL." See, Chudy et al., 2013, Collaborative Study to establish a World Health Organization International standard for hepatitis D virus RNA for nucleic acid amplification technique (NAT)-based assays." WHO Expert Committee on Biological Standardization WHO/BS/2013.2227. Both units are used in this specification. As used herein, recitation of "HDV RNA copies per mL," (not including discussions related to clinical trial results, e.g., as presented in the examples) should be read, for purposes of written description or basis, as "HDV RNA copies/mL or HDV IU/mL." Where a specific quantity of HDV RNA copies per mL is recited, a multiplier of 1.2 may be applied, for the purposes of written description and support, to convert the quantity of HDV RNA copies/mL to the quantity of IU/mL. For example, "120 HDV RNA copies per mL" should be read as "120 copies/mL or 100 IU/mL."

HBV DNA levels are generally described in the art using the IU convention (see Saldanha et al., 2001, An international collaborative study to establish a World Health Organization international standard for hepatitis B virus DNA nucleic acid amplification techniques VoxSanguinis 80(1) 63-71).

Changes in HDV RNA levels may be represented as a "log reduction" following the normal conventions of virology. For example, a 1 log reduction (i.e., −1 log) in viral load (e.g., from 7 log to 6 log) is a 10-fold reduction, and a 2 log reduction (i.e., −2 log) in viral load (e.g., from 7 log to 5 log) is a 100-fold reduction. A reduction from 7 log RNA copies/mL to 6 log RNA copies/mL is equivalent to a reduction from 7 log IU/mL to 6 log IU/mL. Changes in HBV DNA levels may described using the same terminology.

The singular forms "a," "an," and "the" include plural referents unless the context clearly dictates otherwise. Thus, for example, reference to "a compound" includes a plurality of compounds.

The term "administration" refers to introducing a compound, a composition, or an agent of the present disclosure into a host, such as a human. One preferred route of administration of the agents is oral administration. Other routes are intravenous administration and subcutaneous administration.

"Anti-diarrheal agents" may be either of two types: Those that thicken the stool and those that slow intestinal spasms. Thickening mixtures (such as psyllium) absorb water. This helps bulk up the stool and make it more firm. Antispasmodic antidiarrheal products slow the spasms of the intestine by acting on the μ-opioid receptors in the myenteric plexus of the large intestine. By decreasing the activity of the myenteric plexus, which in turn decreases the tone of the longitudinal and circular smooth muscles of the intestinal wall, the amount of time substances stay in the intestine increases, allowing for more water to be absorbed out of the fecal matter. Anti-spasmodics also decrease colonic mass movements and suppress the gastrocolic reflex.

The term "antacid" refers to agents that reduce, or reduce the effects of, gastric acid secretion, and includes H2-Receptor antagonists and proton pump inhibitors.

The terms "baseline," unless otherwise specified or apparent from context, refers to a measurement (of, e.g., viral load, patient condition, ALT level) made prior to a course of therapy.

The terms "BID" (twice a day), "QD" (once per day), "QW" (once per week), and the like have their normal meaning in the medical arts.

The term "comprising" is intended to mean that the compounds, compositions and methods include the recited elements, but not excluding others. "Consisting essentially of" when used to define compounds, compositions and methods, shall mean excluding other elements that would materially affect the basic and novel characteristics of the claimed invention. "Consisting of" shall mean excluding any element, step, or ingredient not specified in the claim. Embodiments defined by each of these transition terms are within the scope of this invention.

The terms "course of treatment" and "course of therapy" are used interchangeably herein, and refer to the medical interventions made after a patient is diagnosed, e.g., as being infected with HDV and in need of medical intervention. Medical interventions include, without limitation, the administration of drugs for a period of time, typically, for HDV infected patients, at least one and typically several or many months or even years.

The term "GI intolerance" refers to any one of diarrhea, nausea, and vomiting individually, or combinations thereof.

The terms "hepatitis flare," "ALT flare" and "immune reactivation," are used interchangeably and refer an abrupt elevation of serum alanine aminotransferase (ALT) to a level over two-fold baseline ALT in a hepatitis patient. In some embodiments, a hepatitis flare is characterized by an abrupt elevation of serum ALT to a level that is over five-fold the upper limit of normal (ULN). In some cases, the serum ALT level is 200 U/L or higher. See, Liaw, Journal of Gastroenterology and Hepatology, 2003, 18:246-252. Methods of measuring serum ALT levels are known in the art. See, e.g., J. Clin. Chem. Clin. Biochem., 1986, 24:481-495. In some embodiments, a hepatitis flare may be indicative of therapeutic efficacy in an HDV patient receiving treatment with lonafarnib.

The term "HDV RNA viral load" or "viral load" of a human serum or plasma sample refers to the amount of HDV RNA in a given amount of a human serum or plasma sample. HDV RNA is generally detected by quantitative real-time reverse transcription-polymerase chain reaction (qRT-PCR) assays. In such assays, the amount of signal generated during the assay is proportional to the amount of HDV RNA in the sample. The signal from the test sample is compared to that of a dilution series of a quantified Hepatitis Delta RNA standard, and a copy number of genome copies is calculated. See, e.g., Kodani et al., 2013, J. Virol. Methods, 193(2), 531; Karatayli et al., 2014, J. Clin. Virol, 60(1), 11. HDV RNA viral load may be reported as RNA copies per mL serum (or plasma) or using International Units (IU) per mL serum (or plasma) (see Chudy et al., 2013, supra). A commercially available assay is available from ARUP Laboratories (Salt Lake City, Utah). The limit of detection for the ARUP HDV RNA assay has been reported to be 31 IU/mL. Analytik Jena AG (Germany) offers the RoboGene® HDV RNA Quantification Kit 2.0, which is CE-IVD certified with WHO standard references to assess the response to antiviral treatment. The limit of detection for the RoboGene® assay is reported to be 6 IU/mL. Reference to a "viral load" without specified units (e.g., "a viral load of less than 100") refers to copies of HDV RNA per mL serum, unless otherwise indicated or apparent from context. Unless otherwise specified, reference to below the level of detection means below 6 IU/mL.

The term "HDV infection" with respect to a human (host) refers to the fact that the host is suffering from HDV infection. Typically, an HDV infected human host will have a viral load of HDV RNA of at least about 2 log HDV RNA copies/mL of host serum or plasma or $10^2$ copies of HDV-RNA/mL of host serum or plasma, often at least about 3 log HDV RNA copies/mL of host serum or plasma or $10^3$ copies of HDV-RNA/mL of host serum or plasma, and, often, especially for patients not on any therapy, at least about 4 log HDV RNA copies/mL of host serum or plasma or $10^4$ copies of HDV-RNA/mL of host serum or plasma, such as about 4 log HDV RNA copies/mL of host serum or plasma to 8 log HDV RNA copies/mL of host serum or plasma or $10^4$-$10^8$ copies of HDV-RNA/mL of host serum or plasma. As used herein, the term "chronic HDV infection" with respect to a human host refers to an HDV infection that has persisted in the human host for at least 6 months, as documented by a positive HDV antibody (Ab) test and/or detectable HDV RNA by qRT-PCR. Diagnosis and pathogenesis of HDV is described, for example, in Wedemeyer et al., Nat. Rev. Gastroenterol. Hepatol, 2010, 7:31-40.

The term "HBV infection" refers to hepatitis B (HBV) infection. It will be appreciated by a person of ordinary skill in the art that HDV infection can only occur in individuals who are also infected with HBV. Thus, a human host having an HDV infection will also have an HBV infection. Diagnosis of HBV infection can be based on the presence of an HBV serologic marker, such as hepatitis B surface antigen (HBsAg), hepatitis B core IgM antibody (anti-HBc IgM), and/or the presence of HBV DNA. Methods of detecting and quantifying HBV serologic markers and HBV DNA are described in the art. See, e.g., Liu et al., 2015, World J Gastroenterol 21:11954-11963. In some embodiments, a human host having an HDV infection and a HBV infection will have a HBV viral load of at least about 2 log HBV DNA copies/mL of host serum or plasma or $10^2$ copies of HBV-DNA/mL of host serum or plasma, often at least about 3 log HBV DNA copies/mL of host serum or plasma or $10^3$ copies of HBV-DNA/mL of host serum or plasma, or at least about 4 log HBV DNA copies/mL of host serum or plasma or $10^4$ copies of HBV-DNA/mL of host serum or plasma.

The term "HBV viral load" of a human serum or plasma sample refers to the number of copies of human HBV DNA in a given amount of human serum or plasma sample. HBV DNA may be detected and quantitated using real-time PCR. Commercial assays for quantitating HBV DNA are available. In the United States, Abbott offers the RealTime HBV assay, which is an in vitro PCR assay for the quantitation of HBV DNA in human serum or plasma. A CE certified kit for real-time PCR-based detection of HBV is commercially available from Analytik Jena, Germany (RoboGene® HBV DNA Quantification Kit 2.0).

"H2-Receptor antagonists" are a class of drugs used to block the action of histamine on parietal cells (specifically the histamine H2 receptors) in the stomach, decreasing the production of acid by these cells. H2 antagonists are used in the treatment of dyspepsia.

"5-HT3 antagonists" are a class of drugs that act as receptor antagonists at the 5-HT3 receptor, a subtype of serotonin receptor found in several critical sites involved in emesis, including vagal afferents, the solitary tract nucleus (STN), and the area postrema itself. The 5-HT3 receptor antagonists suppress vomiting and nausea by inhibiting serotonin binding to the 5-HT3 receptors.

The term "lonafarnib" or "LNF" or "EBP994", also known under the trade name Sarasar (Schering), refers to an FTase inhibitor 4(2[4-[(11R)-3,10-dibromo-8-chloro-6,11-dihydro-5H benzo[5,6]-cyclohepta[1,2b]pyridin-11yl]-piperidino]-2-oxoethyl]-1-piperidinecarboxamide) (also identified as Sch-66336 or SCH 66336) having the structure shown below:

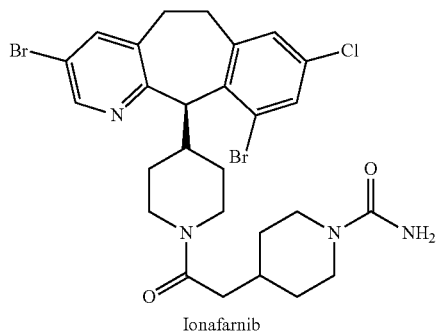 [SMILES: NC(=O)N1CCC(CC(=O)N2CCC([C@H]3c4ncc(Br)cc4CCc4cc(Cl)cc(Br)c43)CC2)CC1]

Lonafarnib

Lonafarnib is a crystalline solid with a melting point of approximately 200° C. and is non-hygroscopic. Its molecular weight is 638.7. In the solid state, the compound is thermally stable. In solution, it is stable at neutral pH but will hydrolyze in acidic or basic conditions. It is a poorly water soluble tricyclic compound, which when formulated in crystalline forms results in low and variable bioavailability in animals. Considerable effort has been devoted to formulation development to improve the oral bioavailability. In addition to the drug substance, suitable pharmaceutical formulations of lonafarnib for administration in capsules contain povidone, poloxamer 188, croscarmellose sodium, silicon dioxide, and magnesium stearate. The product is formulated with a drug: povidone (1:1) coprecipitate to achieve optimal bioavailability. These are safe and well tested excipients that are commonly used in marketed products.

A patient is considered "HDV-RNA negative," or, equivalently, "cleared of HDV," when the quantity of HDV RNA per mL serum or plasma is below the limit of detection for the assay used (i.e., a qRT-PCR assay). A patient is considered "persistently HDV-RNA negative" when the quantity of HDV RNA per mL serum or plasma is below the limit of detection in one viral load measurement and remains below the limit of detection in a subsequent viral load measurement or measurements carried out over an extended period of time, such as at least 6 weeks, at least 12 weeks, at least 24 weeks, at least 36 weeks, at least 48 weeks, or at least 1 year. If not otherwise specified, a patient is considered "persistently HDV-RNA negative" if two viral load measurements at least 24 weeks apart do not detect HDV virus and viral RNA is not detected in any intervening viral load measurement. It will be appreciated that measurements made from a serum sample may not detect the presence of low levels of virus in hepatocytes ("reservoir"). In many instances the presence of low levels will not give rise to any symptoms. In some instances a reservoir viral population may expand, causing the patient to relapse and require further treatment.

"NK1" is a G protein-coupled receptor located in the central and peripheral nervous system. This receptor has a dominant ligand known as Substance P (SP). SP is a neuropeptide, composed of 11 amino acids, which sends and receives impulses and messages from the brain. It is found in high concentrations in the vomiting center of the brain, and results in a vomiting reflux when activated. NK-1 receptor antagonists block signals given off by NK1 receptors.

The term "oral dosage form," as used herein, refers to a dosage form that is suitable for oral administration such as tablets, capsules, gel caps, syrups, elixirs, and suspensions. "Solid oral dosage forms" include tablets, capsules, caplets, and the like.

The term "oral unit dosage form," as used herein, refers to a unit dosage form that is intended to be orally administered.

The terms "patient", "host," or "subject," are used interchangeably and refer to a human infected with HDV, including patients previously infected with HDV in whom virus has cleared.

The term "pharmaceutical composition" is meant to encompass a composition suitable for administration to a subject. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intratracheal, intramuscular, subcutaneous, inhalational, and the like.

The terms "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one and more such excipients, diluents, carriers, and adjuvants. A wide variety of pharmaceutically acceptable excipients, such as vehicles, adjuvants, carriers or diluents, and auxiliary substances, such as pH adjusting and buffering agents, tonicity adjusting agents, stabilizers, wetting agents and the like, are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc. For oral preparations, lonafarnib and/or ritonavir can be used alone or in pharmaceutical formulations of the invention comprising, or consisting essentially of, or consisting of lonafarnib in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The term "pharmaceutically acceptable salt" refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. In the event that embodiments of the disclosed agents form salts, these salts are within the scope of the present disclosure. Reference to an agent of any of the formulas herein is understood to include reference to salts thereof, unless otherwise indicated.

As used herein, the term "polymer" refers to an organic substance composed of a plurality of repeating structural units (monomeric units) covalently linked to one another. The term "polymer" as used herein encompasses organic and inorganic polymers. In some embodiments, a polymer is a compound of natural origin (e.g., protein-based polymers such as collagen, albumin, or gelatin, or polysaccharides such as alginate, cyclodextrin, dextran, agarose, chitosan, hyaluronic acid, starch, or cellulose). In some embodiments, a polymer is a semi-synthetic compound (e.g., cellulose derivatives). In some embodiments, a polymer is a synthetic compound (e.g., polyethylene glycols, poloxamers, polylactides, acrylic acid polymers, or polyamides). In some embodiments, a polymer is a natural biodegradable polymer (e.g., albumin, collagen, gelatin, or starch). In some embodiments, a polymer is a synthetic biodegradable polymer (e.g., polylactides, polyamides). In some embodiments, a polymer is a non-biodegradable polymer (e.g., polyethylenes, polymethyl methacrylates, polyvinyl pyrolidine, or cellulose derivatives).

"Proton pump inhibitors" are a class of antisecretory compounds that suppress gastric acid secretion by specific inhibition of the H+/K+ ATPase enzyme system at the secretory surface of the gastric parietal cell. Because this enzyme system is regarded as the acid (proton) pump within the gastric mucosa, inhibitors of this system have been characterized as a gastric acid-pump inhibitors in that they block the final step of acid production. This effect is dose-related and leads to inhibition of both basal and stimulated acid secretion irrespective of the stimulus.

The term "therapeutically effective amount" as used herein refers to that amount of an embodiment of the agent (which may be referred to as a compound, an inhibitory agent, and/or a drug) being administered that will treat to some extent a disease, disorder, or condition, e.g., relieve one or more of the symptoms of the disease, i.e., infection, being treated, and/or that amount that will prevent, to some extent, one or more of the symptoms of the disease, i.e., infection, that the subject being treated has or is at risk of developing.

The terms "treatment", "treating", and "treat" are defined as acting upon a disease, disorder, or condition with an agent to reduce or ameliorate the pharmacologic and/or physiologic effects of the disease, disorder, or condition and/or its symptoms. "Treatment," as used herein, covers any treatment of a disease in a human subject, and includes: (a) reducing the risk of occurrence of the disease in a subject determined to be predisposed to the disease but not yet diagnosed as infected with the disease, (b) impeding the development of the disease, and/or (c) relieving the disease, i.e., causing regression of the disease and/or relieving one or more disease symptoms. "Treatment" is also meant to encompass delivery of an inhibiting agent to provide a pharmacologic effect, even in the absence of a disease or condition. For example, "treatment" encompasses delivery of a disease or pathogen inhibiting agent that provides for enhanced or desirable effects in the subject (e.g., reduction of pathogen viral load, reduction of disease symptoms, etc.).

The term "undetectable," as used with reference to HDV RNA levels, means that no HDV RNA copies can be detected by the assay methodology employed. In some embodiments, the assay is quantitative RT-PCR. The term "essentially undetectable," as used with reference to HDV RNA levels, means that fewer than 50 HDV RNA copies/mL serum or plasma can be detected by the assay methodology employed (e.g., quantitative RT-PCR), sometimes fewer than 25 HDV RNA copies/mL, sometimes fewer than 10 HDV RNA copies/mL.

The term "unacceptable gastrointestinal side effects" refers to gastrointestinal side effects that that prevent a patient from completing a recommended course of therapy.

The term "unit dosage form," as used herein, refers to physically discrete units suitable as unitary dosages for human subjects, each unit containing a predetermined quantity of a compound (e.g., an anti-viral compound and/or boosting agent, as described herein) or compounds, calculated in an amount sufficient to produce the desired treatment effect in association with a pharmaceutically acceptable diluent, carrier or vehicle.

All deuterated analogs (a compound is a deuterated analog of another compound, the "parent compound", if it differs from the parent compound by only replacement of one or more hydrogen atoms with one or more deuterium atoms) of any active pharmaceutical ingredient described herein, including without limitation, lonafarnib, and the boosting agents ritonavir and cobicistat, are, for purposes of the present invention, encompassed by reference to the parent compound.

All stereoisomers of any agent described herein, including without limitation, lonafarnib, ritonavir, cobicistat, and any other active pharmaceutical agent described herein, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

II. Introduction

In one aspect, the present invention relates to treatment of patients infected with hepatitis D virus (HDV) by co-administering the prenyltransferase inhibitor lonafarnib and the CYP3A4 inhibitor ritonavir. As is described herein below, it has been discovered that although administration of lonafarnib at 100 mg BID for 28 days reduced viral load, the reduction was not sufficient for development as a therapeutic. Higher doses of lonafarnib were poorly tolerated and resulted in an unacceptable level of adverse events. Thus, when administered at 200 mg BID, serum levels of lonafarnib dropped after about one month of treatment, mostly likely due to poor tolerability, poor compliance by patients, and loss of agents that pass through the GI tract. When administered at 300 mg BID, serum levels of lonafarnib were lower than expected, again, likely a result of poor tolerability. See, e.g., Table 11 below. Thus, while administration of lonafarnib at 100 mg BID was not sufficiently efficacious, higher doses were associated with significant GI-related adverse effects, rendering the treatment unsuitable as routine therapies for patients infected with HDV.

The present invention relates in part to the discovery that administration of lonafarnib in combination with ritonavir ("lonafarnib-ritonavir cotherapy") according to dose schedules described herein is efficacious for treatment of HDV and results in superior outcomes compared to lonafarnib monotherapy. Surprisingly, administration of 100 mg lonafarnib BID and 100 mg ritonavir QD resulted in higher serum concentrations of lonafarnib than observed with lonafarnib monotherapy measured after 56 days of treatment, but a lower frequency of adverse effects (see, e.g., Table 10 and Table 11 below). It has also been discovered that even lower doses of lonafarnib (e.g., 25 mg lonafarnib BID or 50 mg lonafarnib BID), administered in combination with ritonavir, are efficacious in reducing HDV RNA viral load and are better tolerated (see, e.g., FIGS. 15A-B and Table 16 below).

Further, it has been discovered that lonafarnib-ritonavir co-therapy may be supplemented or combined with prophylactic administration of GI modifying agents (in particular prophylactic administration of one or more of an anti-emetic agent, an anti-diarrheal, and an antacid) to improve patient outcomes. Thus, one aspect of the invention relates to lonafarnib-ritonavir co-therapy combined with prophylactic administration of a combination of GI modifying agents.

In one embodiment the patient receiving lonafarnib-ritonavir co-therapy receives lonafarnib at a daily dose of 50-150 mg per day, for example 50 mg per day, 75 mg per day, 100 mg per day, or 150 mg per day, and receives ritonavir at a daily dose of 100-200 mg per day, for example 100 mg per day or 200 mg per day. Certain aforementioned doses can be achieved by administering lonafarnib QD or BID and administering ritonavir QD or BID. Preferably, each administration of lonafarnib is no more than 75 mg, e.g., no more than 50 mg, and each administration of ritonavir is no more than 100 mg. In one approach, lonafarnib is administered BID and ritonavir is administered QD. In one approach both lonafarnib and ritonavir are administered BID. In one approach both lonafarnib and ritonavir are administered QD.

III. HDV Treatment

In one aspect, the present invention provides methods for treating HDV infection, in which an HDV-infected patient is treated by oral administration of lonafarnib and ritonavir (which may be referred to as "lonafarnib administration," "lonafarnib-ritonavir co-therapy," and the like). In some embodiments, lonafarnib and ritonavir are administered according to doses and dosing schedules described herein. In some embodiments, the HDV-infected patient receives prophylactic treatment with one, two, or three or more classes of gastrointestinal (GI) modifying agents. In some embodiments patients receiving lonafarnib-ritonavir co-therapy are also treated with interferon (e.g., unpegylated or pegylated interferon-alpha or interferon-lambda).

Lonafarnib has been investigated for treatment of solid and hematological malignancies, Hutchinson-Gilford progeria syndrome, and chronic hepatitis delta virus infection, but is not approved for any indication. The majority of reports concerning lonafarnib dosing are related to administration of lonafarnib to patients with cancer in combination with one or multiple antineoplastic agents.

Ritonavir (CAS Registry No. 155213-67-5), which is marketed under the trade name Norvir® by AbbVie, Inc., has been administered as an antiretroviral agent, in combination with other antiviral agents, for treatment of HIV-1 infected individuals. See Miller et al., 2015, Infection and Drug Resistance, 8:19-29. For treatment of HIV-1 in adult patients, the recommended dosage of ritonavir is 600 mg twice daily by mouth to be taken with meals. See Norvir® package insert. Ritonavir has also been used as a pharmacologic enhancer or boosting agent. Pharmacokinetic "boosting" refers to the pharmacological enhancement of orally dosed drugs through the co-dosing with pharmacological enhancers which render these drugs more effective. Ritonavir has been used to boost the $C_{max}$ of proteases used to treat HIV infection. The boosting effect of ritonavir results from several properties of the drug. Ritonavir inhibits two key stages of metabolism.

First, ritonavir inhibits first-pass metabolism during absorption. Enterocytes that line the intestine contain both CYP3A4, one of the key cytochrome P450 isoenzymes associated with drug metabolism, and P-glycoprotein, an efflux transporter that can effectively pump drugs out of the gut wall and back into the intestinal lumen. Ritonavir inhibits both of these proteins. Consequently, co-administration of ritonavir and a drug transported by P-glycoprotein and/or metabolized by enterocyte CYP3A4 may increase the Cmax of the co-administered drug. Second, ritonavir inhibits CYP3A4 in the liver, thereby maintaining a drug's plasma half-life.

Several factors make it impossible to predict, and difficult to determine, what an acceptable dose of ritonavir is for use as a boosting agent.

First, the boosting effects of ritonavir vary broadly and unpredictably depending on the primary (i.e., co-administered) drug. This is illustrated by the Norvir® package insert (available at the FDA website www.rxabbvie.com/pdf/norvirtab_pi.pdf) which shows that the effect of co-administration of ritonavir with a primary drug can range from a 350-fold increase AUC of the primary drug (Fluticasone propionate, delivered as aqueous nasal spray) to an 11-fold increase (sidenafil) to a 1.2-fold increase (trimethoprim). There is also great variance even within a single drug class. For example, in a meta-study of 17 dose-ranging pharmacokinetic trials of protease inhibitors, Hill et al. evaluated the ritonavir boosting effect at doses of 50-800 mg daily with seven protease inhibitors: amprenavir, atazanavir, darunavir, indinavir, lopinavir, saquinavir and tipranavir. Hill concluded that ritonavir has a dose-dependent boosting effect on Indinavir, tipranavir and lopinavir, but that the boosting effect of ritonavir on darunavir or saquinavir is not correlated with its dose.

In addition, the pharmacokinetics of ritonavir in patients with hepatitis is likely more unpredictable relative to other treatment populations. Li et al. reported that hepatic CYP3A4 expression is down-regulated in individuals with chronic HBV infection. Although the subpopulation of HBV-infected patients co-infected with HDV was not separately studied, it is likely CYP3A4 down-regulation occurs in HDV positive individuals. See Li et al., 2006, Zhonghua Yi Xue Za Zhi, 86:2703-2706.

It has also been reported that ritonavir may inhibit P-glycoprotein found in peripheral blood lymphocytes. See Lucia et al., 2001, J Acquir Immune Defic Syndr. 27:321-30. If lonafarnib is a substrate of P-glycoprotein, the co-administration of ritonavir could cause less lonafarnib to be transported back out of the cell, thereby increasing the drug's intracellular half-life.

Further, the HDV patient subpopulation is characterized by higher levels of cirrhosis (which develops in about 60 to 70% of patients with chronic hepatitis D) than patients infected with HBV only. The pharmacokinetics of ritonavir in the HDV patient population is more unpredictable relative to other populations with lower levels of or no cirrhosis.

The therapeutic effects of co-administration of lonafarnib and ritonavir to patients with chronic HDV were not known prior to the present invention, and nothing in the medical literature prior to the present invention described administration regimens (e.g., doses and dose scheduling) that are safe, tolerable, and effective for treating HDV patients and patients with chronic HDV infection.

In addition, the side effect profiles of administration of lonafarnib and co-administration of lonafarnib and ritonavir have not been previously determined. Diarrhea, nausea, and vomiting are reported as side-effects of both lonafarnib administration (see, Schering IB) and ritonavir administration (see Norvir Package Insert). In cancer patients, a dose of 200 mg BID lonafarnib was characterized as "well tolerated." See Hanrahan et al., 2009, "A phase II study of Lonafarnib (SCH66336) in patients with chemorefractory, advanced squamous cell carcinoma of the head and neck," *Am J Clin Oncol.* 32:274-279 (describing lonafarnib therapy following platinum-based therapy for recurrent SCCHN) and List et al., 2002, *Blood,* 100:789A (a lonafarnib dose of 200 mg BID was well tolerated in patients with advanced hematologic malignancies). However, the side-effect profile of administration of therapeutically effective levels of lonafarnib to patients with chronic HDV infection was not known, and the side-effect profile of lonafarnib-ritonavir co-therapy was not known for any population.

Effect of Lonafarnib Administration on HDV Infection

As described below in Example 1, a cohort of patients with chronic delta hepatitis (HDV) received treatment with 100 mg lonafarnib BID for 28 days and showed a mean change in HDV RNA levels from baseline to nadir of −0.74 log HDV RNA copies/mL, compared to −0.24 log HDV RNA copies/mL in patients receiving placebo. See also, Table 1 below. Plasma levels of lonafarnib ranged between 200 ng/mL and 1,100 ng/mL during treatment, and subjects with higher plasma levels of lonafarnib experienced greater declines in HDV RNA titers during treatment. See FIG. 2. However, a more robust reduction in viral load was desired.

As described in Example 2 below, administration of higher doses of lonafarnib to HDV-infected patients resulted in a more dramatic reduction of viral load but with unacceptable tolerability. In patients receiving 200 mg BID lonafarnib for 28 days the mean change in viral load was −1.63 log HDV RNA copies/mL. In patients receiving 300 mg BID lonafarnib 28 days the mean change in viral load was −2.00 log HDV RNA copies/mL. See also, Table 1 below.

Although daily administration of 200 or 300 mg BID lonafarnib provided superior viral load declines in HDV patients compared to a daily administration of 100 mg BID lonafarnib, administration of lonafarnib 200 mg BID or 300 mg BID resulted in significant adverse effects, which renders these dosage regimens unsuitable for long term therapy.

Effect of Lonafarnib-Ritonavir Co-Administration on HDV Infection

Figure 5:
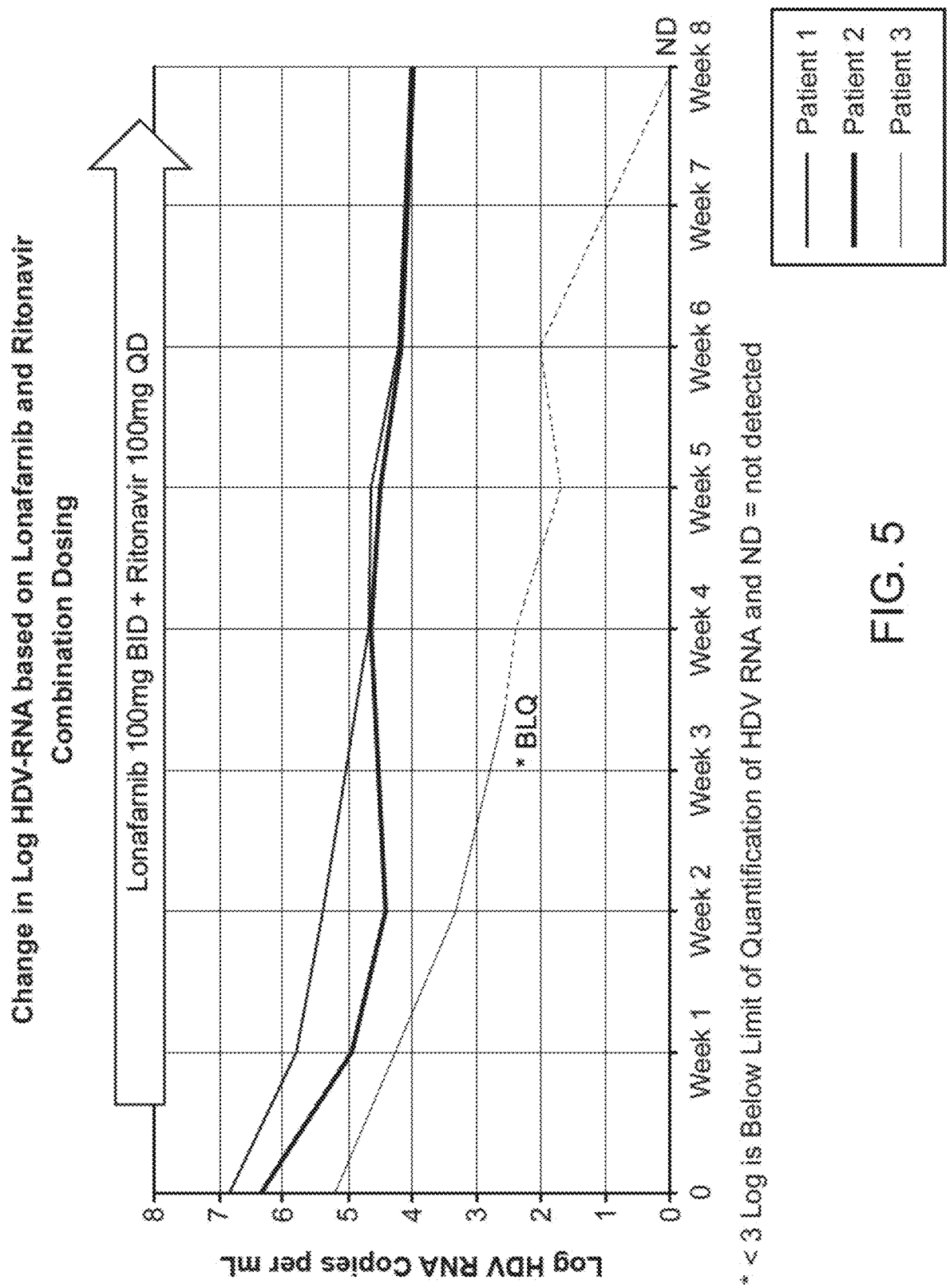
FIG. 5. HDV RNA viral titers in patients treated with lonafarnib at doses of 100 mg BID and ritonavir at 100 mg QD for a period of 28 days. See Example 4.
Figure 17:
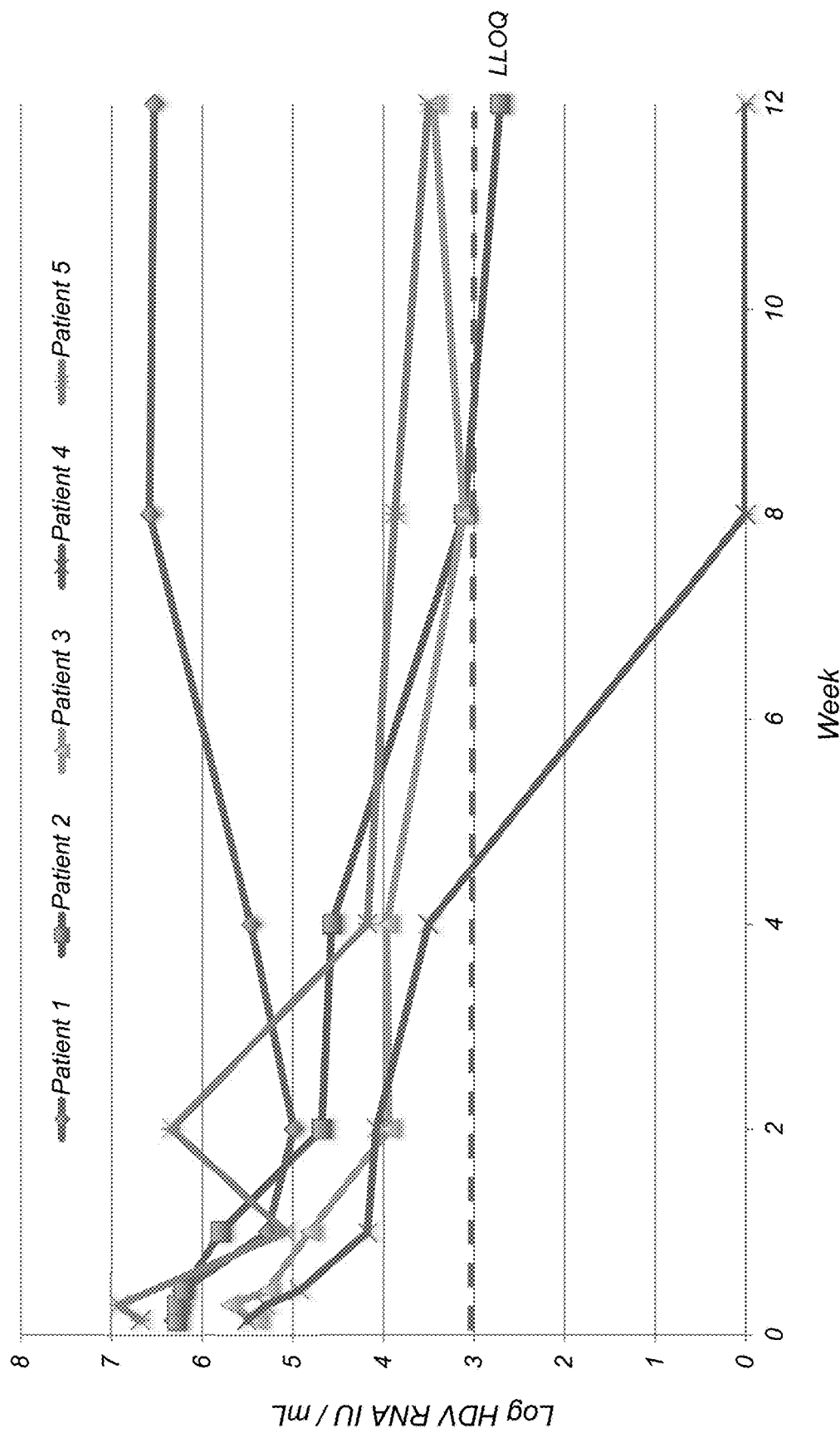
FIG. 17. Time course of HDV RNA levels (copies/mL) in patients treated with 50 mg BID lonafarnib and 100 mg BID ritonavir as described in Example 12.

As illustrated in Examples 4-6 and 12, below, lonafarnib-ritonavir co-therapy substantially reduced HDV viral load in patients at different combinations of doses. Example 4 describes the superior efficacy observed with lonafarnib-ritonavir co-therapy as compared to lonafarnib monotherapy. In patients receiving 100 mg BID lonafarnib in combination with 100 mg QD ritonavir for 28 days, the mean change in viral load was −2.2 log HDV RNA copies/mL. See also Table 1 below. Example 12 demonstrates that comparable HDV RNA viral load decline was observed for patients receiving 25 mg BID or 50 mg BID lonafarnib in combination with 100 mg BID ritonavir as for patients receiving higher doses of lonafarnib in the lonafarnib-ritonavir co-therapy. Furthermore, in some instances, lonafarnib-ritonavir co-therapy reduced HDV viral load to undetectable levels at week 8. See FIG. 5 and FIG. 17. Thus, in accordance with the invention, the use of lower doses of lonafarnib in combination with a boosting agent, alone or in combination with an interferon, can enable patients to achieve significant therapeutic benefit, with the lower lonafarnib dose in the range of 25 mg QD to 100 mg BID, and preferred doses of 50 mg BID lonafarnib in combination with 100 mg BID ritonavir.

TABLE 1

Change in Viral Load in Patients After 28 Days Lonafarnib Therapy or Lonafarnib-Ritonavir Co-Therapy

| | Mean Log Change in Serum HDV RNA at Day 28 | N |
|---|---|---|
| Placebo | −0.24 | 4 |
| Lonafarnib 100 mg BID* | −0.74 | 6 |
| Lonafarnib 200 mg BID | −1.63 | 6 |
| Lonafarnib 300 mg BID | −2.00 | 3 |
| Lonafarnib 100 mg BID with Ritonavir 100 mg QD | −2.20 | 3 |

*Mean Plasma levels of lonafarnib ranged between 540 ng/mL and 890 ng/mL

Accordingly, in various methods of the invention, lonafarnib and ritonavir each are administered in combination with the other orally on a continuous, daily basis, at least once per day (QD), and in various embodiments two times per day (BID), to an HDV patient. In some embodiments, lonafarnib-ritonavir co-therapy is administered daily for at least 30 consecutive days. In some embodiments, lonafarnib-ritonavir co-therapy is administered daily for at least several months. In some embodiments, patients may receive lonafarnib-ritonavir co-therapy for the rest of their lives.

Figure 2:
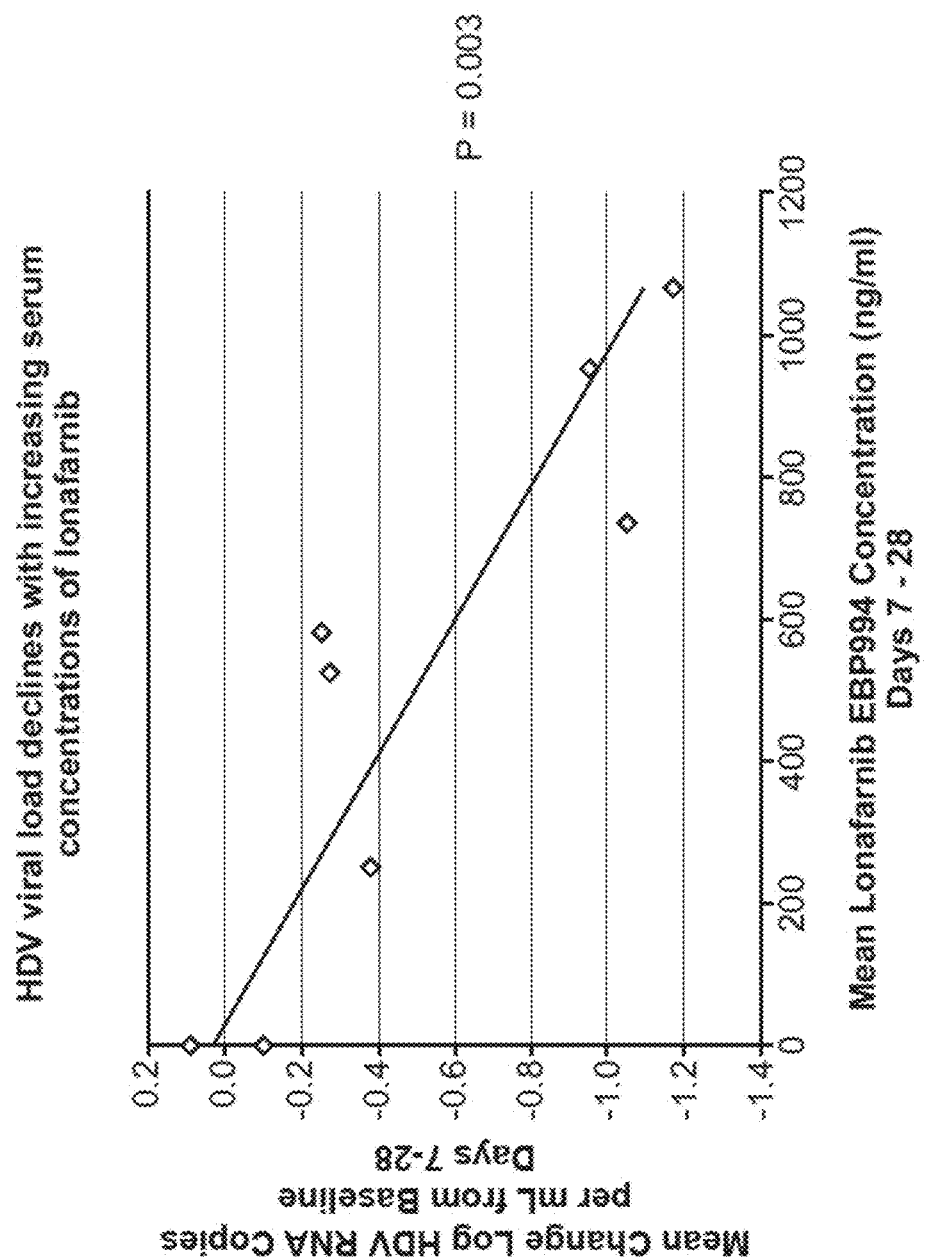
FIG. 2. Change in HDV RNA viral load, relative to serum levels of lonafarnib, in patients treated with 100 mg lonafarnib BID for 28 days. See Example 1.
Figure 7:
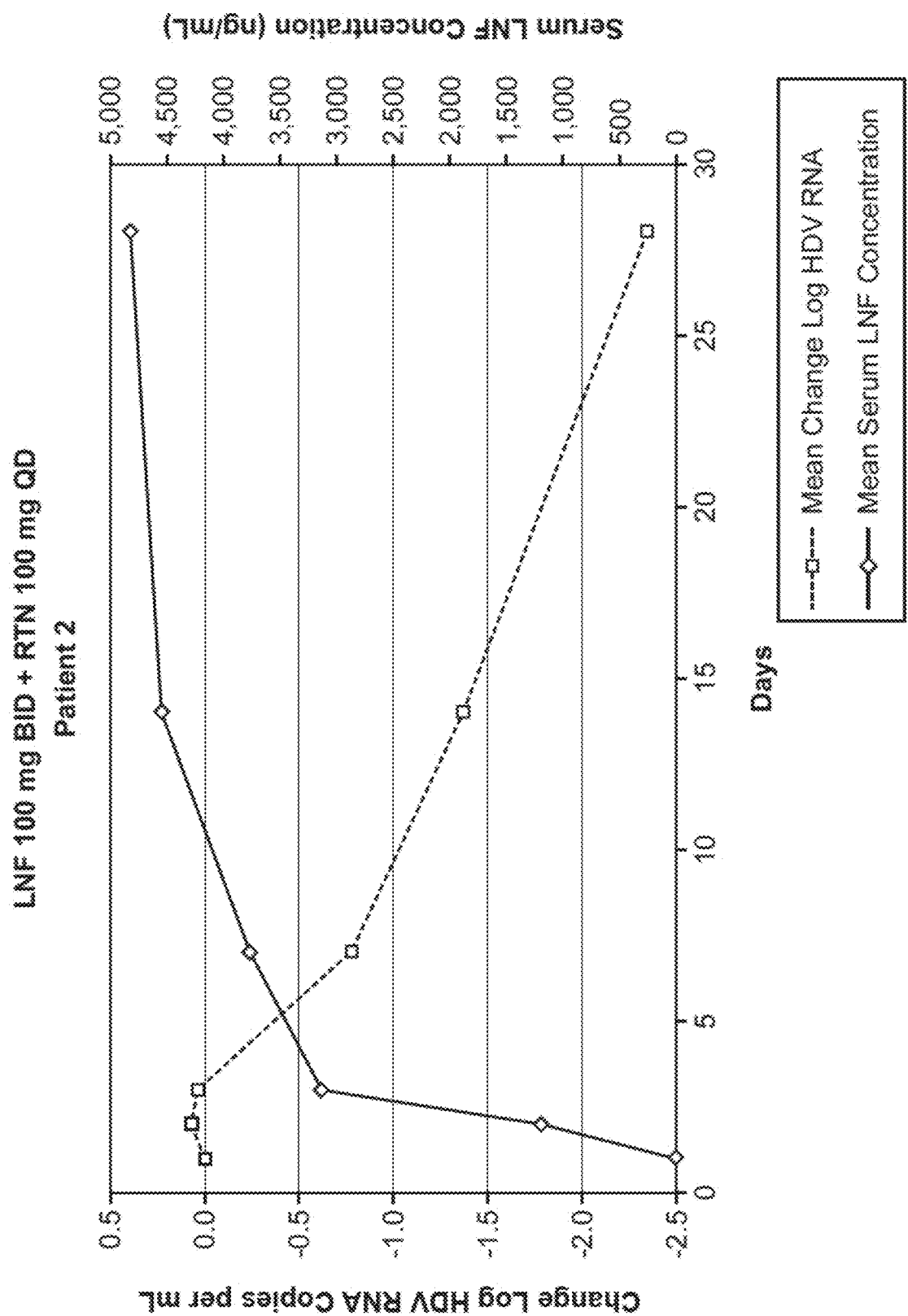
FIG. 7. Inverse correlation between higher lonafarnib serum levels and HDV viral load in a patient administered 100 mg lonafarnib BID and 100 mg ritonavir QD.

As shown in FIG. 2, HDV viral load declines with increasing serum concentrations of lonafarnib. The correlation between lonafarnib serum levels and viral load in patients receiving lonafarnib-ritonavir co-therapy is seen by comparing the viral load of a patient who maintained a serum lonafarnib concentration in the range of about 3,500 to 5,000 ng/mL for about 21 days (see FIG. 7) with the viral load of a patient who maintained a serum lonafarnib concentration in the range of about 1500 to 2500 ng/mL for about 21 days (see FIGS. 7 and 8), with the former patient doing markedly better. See also Table 12, showing that the patient with the highest lonafarnib serum level after four weeks of co-therapy had the greatest decrease in viral load, and that patients with lonafarnib serum levels greater than 2,000 ng/mL had, in general, more dramatic reductions in viral load than patients with serum levels lower than 2,000 ng/mL (patient 4 is an exception to the trend).

Accordingly, in certain embodiments, lonafarnib and ritonavir are co-administered according to a schedule that results in serum lonafarnib levels greater than 2,000 ng/mL, for example, greater than 4,000 ng/mL. In some embodiments, lonafarnib and ritonavir are co-administered according to a schedule that results in serum lonafarnib levels in the range of about 3,500 ng/mL to about 8,500 ng/mL (e.g., about 4,500 ng/mL to about 7,500 ng/mL, about 5,000 ng/mL to about 6,000 ng/mL, about 5,500 ng/mL to about 6,500 ng/mL, about 6,000 ng/mL to about 7,000 ng/mL, or about 6,500 ng/mL to about 7,500 ng/mL) or about 5,000 ng/mL to about 7,000 ng/mL.

As used herein, a serum lonafarnib level or concentration can be measured from a serum sample obtained from a subject periodically (such as weekly, biweekly, monthly or according to other schedules) and the levels during intervening periods can be extrapolated. For example, if a measurement of 4,000 ng/mL is obtained at 4 weeks and a measurement of 6,000 ng/mL is obtained at 6 weeks, for purposes of this analysis it is concluded that the serum level during the intervening two weeks ranged between 4,000 and 6,000 ng/mL. In some embodiments the first measurement is made no earlier than one week after the initiation of oral therapy.

Serum levels of lonafarnib can be measured using art-known methods, including radioimmunoassays, chromatographic assays, mass spectrometry and the like. In some embodiments of the invention, patient serum samples were extracted using a protein precipitation method (Acetonitrile). The samples were then loaded onto Waters CSH C18, 2.1×50 mm, 1.7 µm column for separation, followed by LC-MS/MS in positive ion mode for detection of lonafarnib. The assay range for lonafarnib was 1-2500 ng/mL.

Lonafarnib and Ritonavir Doses

In some embodiments, lonafarnib-ritonavir co-therapy comprises administering lonafarnib at a total daily dose in the range of 50 mg to 150 mg (e.g., a total daily dose of about 50 mg, about 75 mg, about 100 mg, about 125 mg, or about 150 mg) and administering ritonavir at a total daily dose in the range of 100 mg to 200 mg (e.g., a total daily dose of about 100 mg, about 150 mg, or about 200 mg). In some embodiments, the total daily dose of lonafarnib is 50 mg and the total daily dose of ritonavir is 200 mg. In some embodiments, the total daily dose of lonafarnib is 100 mg and the total daily dose of ritonavir is 200 mg. In some embodiments, the total daily dose of lonafarnib is 150 mg and the total daily dose of ritonavir is 200 mg.

In some embodiments, lonafarnib is administered BID. In some embodiments, lonafarnib is administered QD. In some embodiments, lonafarnib is administered at a dose of 25 mg BID. In some embodiments, lonafarnib is administered at a dose of 50 mg BID. In some embodiments, lonafarnib is administered at a dose of 50 mg QD. In some embodiments, lonafarnib is administered at a dose of 75 mg BID. In some embodiments, lonafarnib is administered at a dose of 75 mg QD. In some embodiments, lonafarnib is administered at a dose of 100 mg QD.

In some embodiments, ritonavir is administered BID. In some embodiments, ritonavir is administered QD. In some embodiments, ritonavir is administered at a dose of 100 mg BID. In some embodiments, ritonavir is administered at a dose of 100 mg QD. In some embodiments, ritonavir is administered at a dose of 75 mg BID. In some embodiments, ritonavir is administered at a dose of 50 mg BID.

Exemplary doses, for illustration and not for limitation, are provided in Table 2 below. Usually, lonafarnib and ritonavir are administered (e.g., self-administered by the patient) together at about the same time (e.g., simultaneously or within about 15 minutes of each other).

TABLE 2

|  | Embodiment 1 | Embodiment 2 | Embodiment 3 | Embodiment 4 |
|---|---|---|---|---|
| Dose lonafarnib | 75 mg BID | 50 mg BID | 75 mg BID | 25 mg BID |
| Dose ritonavir | 100 mg BID | 100 mg BID | 100 mg QD | 100 mg BID |
|  | Embodiment 5 | Embodiment 6 | Embodiment 7 | Embodiment 8 |
| Dose lonafarnib | 75 mg QD | 50 mg QD | 75 mg QD | 50 mg QD |
| Dose ritonavir | 100 mg QD | 100 mg QD | 100 mg BID | 100 mg BID |

Each of Embodiments 1-8 in Table 2 may be administered with prophylactic GI modifying agents (e.g., an anti-emetic agent, an anti-diarrheal agent, and an antacid), and/or with an interferon (e.g., interferon alpha or interferon lambda). See, Section V and Section VI below.

In some embodiments, lonafarnib and ritonavir (or similar boosting agent, such as cobicistat) are administered to the patient, and both the ritonavir dose and the lonafarnib dose are at least 50 mg QD or at least 100 mg QD for at least 30 days, usually at least about 60 or even 90 days or longer, including 6 months to a year or longer. In some embodiments, dosing will be discontinued after virus levels have decreased to undetectable levels for a period of time (such as 1 to 3 months or longer). In one approach suitable doses of lonafarnib/ritonavir include for least for 30 days, more often at least 60 days, and typically at least 90 days, or longer than 90 days. In one approach treatment of hepatitis delta virus (HDV) infection in a human involves administering a daily dose of about 50 mg/day, about 100 mg/day, or about 150 mg/day of lonafarnib (e.g., about 25 mg BID, about 50 mg BID, about 50 mg QD, about 75 mg BID, about 75 mg QD, or about 100 mg QD of lonafarnib), and a therapeutically effective amount of a CYP3A4 inhibitor (e.g., ritonavir or cobicistat) for at least about 30 days, thereby treating the HDV infection. In one approach ritonavir is dosed at 100 mg QD.

In some embodiments, treatment with lonafarnib-ritonavir co-therapy results in a serum lonafarnib concentration that is greater than 2,000 ng/mL when measured after 4 weeks of treatment. In some embodiments, treatment with lonafarnib-ritonavir co-therapy results in a serum lonafarnib concentration that is greater than 3,000 ng/mL when measured after 4 weeks of treatment.

Patient Population

In some embodiments, a patient to be treated with a co-therapy described herein is a patient having a chronic HDV infection. In some embodiments, the patient to be treated has a chronic HDV infection of at least 6 months duration documented by a positive HDV antibody (Ab) test, and/or detectable HDV RNA by qRT-PCR. In some embodiments, a patient to be treated with a co-therapy method described herein is a patient having an acute HDV infection, one that is newly diagnosed or otherwise believed not to have existed in the patient for more than six months. Diagnosis and pathogenesis of HDV is described, for example, in Wedemeyer et al., Nat. Rev. Gastroenterol. Hepatol, 2010, 7:31-40. HDV is known to exist in a variety of subtypes; the methods described herein are suitable for treating all HDV patients, regardless of HDV subtype.

In some embodiments, a patient to be treated has a baseline viral load of at least $10^4$ HDV RNA copies per mL serum, e.g., at least $10^5$ HDV RNA copies per mL serum or plasma, at least $10^6$ HDV RNA copies per mL serum or plasma, at least $10^7$ HDV RNA copies per mL serum or plasma, or at least $10^8$ HDV RNA copies per mL serum or plasma. In some embodiments, HDV viral load is measured using serum samples from the patient. In some embodiments, HDV viral load is measured using plasma samples from the patient. In some embodiments, viral load is measured by quantitative RT-PCR. qRT-PCR assays for quantification of HDV RNA in serum or plasma are known in the art, e.g., as described above.

In some embodiments, a patient to be treated exhibits one or more symptoms of liver dysfunction. In some embodiments, the patient exhibits one or more liver function parameters that are outside the normal parameters for a healthy control (e.g., a subject that is not infected with HDV or HBV). In some embodiments, the liver function parameter is selected from the group consisting of serum albumin, bilirubin, alanine aminotransferase (ALT), aspartate aminotransferase (AST), and prothrombin activity. In some embodiments, the patient has a serum ALT level that is at least two-fold higher than the upper limit of normal (ULN) (e.g., at least 2-fold, at least 3-fold, at least 4-fold, at least 5-fold, at least 6-fold, at least 7-fold, at least 8-fold or higher than the ULN). Liver function parameters are described in the art. See, e.g., Limdi et al., Postgrad Med J, 2003, 79:307-312. Methods of measuring these liver function parameters are known in the art and are also commercially available.

Dose Escalation and Dose Reduction

In one embodiment the patient being treated for HDV infection receives an escalating dosage regimen of lonafarnib, in that one or more later doses is a larger dose than one or more earlier doses. In some embodiments, an escalating dosage regimen may increase the patient's tolerance to the drug and minimize side effects. In some embodiments, dose escalation comprises administering lonafarnib at a first dose for a first treatment period followed by administering lonafarnib at a second dose that is higher than the first dose for a second treatment period. In some embodiments, the length of time for the first treatment period is the same as the length of time for the second treatment period. In some embodiments, the first treatment period and the second treatment period are different lengths of time. In some embodiments, dose escalation further comprises administering one or more additional doses of lonafarnib for one or more additional treatment periods.

In some embodiments, the duration of the administration of each dosage in the escalating regimen is within 1-4 weeks. The duration of each dosage may be adjusted (e.g., accelerated) by a clinician based on the patient's response. For example, without limitation, a patient may be given lonafarnib 25 mg BID for an initial two-week period, followed by 50 mg BID for a second two-week period until a predetermined desired final dose is reached. Typically the escalating doses are co-administered with ritonavir at a suitable dose, for example, 100 mg QD or BID. Dose escalation may continue to 75 mg BID or higher (e.g., 75 mg BID), including 100 mg BID and higher (e.g., 100 mg BID).

In some embodiments, the lonafarnib-ritonavir co-therapy comprises administering the lonafarnib at a first dose for a first treatment period and then administering lonafarnib at a second dose that is higher than the first dose for a second treatment period if the patient does not experience unacceptable gastrointestinal side effects during the first treatment period. As a non-limiting example, in some embodiments, lonafarnib is administered at a first dose of 50 mg BID for a first treatment period, and if the patient does not experience unacceptable gastrointestinal side effects during the first treatment period, the patient is administered a second dose of 75 mg BID for a second treatment period.

In some embodiments, the lonafarnib-ritonavir co-therapy comprises administering the lonafarnib at a first dose for a first treatment period and then administering lonafarnib at a second dose that is lower than the first dose for a second treatment period if the patient experiences unacceptable gastrointestinal side effects during the first treatment period. As a non-limiting example, in some embodiments, lonafarnib is administered at a first dose of 75 mg BID for a first treatment period, and if the patient experiences unacceptable gastrointestinal side effects during the first treatment period, the patient is administered a second dose of 50 mg BID for a second treatment period.

Duration of Treatment, Induction of Immunologic Reactivation, and Treatment Endpoints Patients may receive lonafarnib-ritonavir co-therapy for a predetermined time, an indefinite time, or until an endpoint is reached. Treatment may be continued on a continuous daily basis for at least two to three months. Therapy is typically for at least 30 days or one month, more often at least 60 days or two months, or at least 90 days or three months, even more often at least 120 days or four months, sometimes for at least 150 days or five months, and sometimes for at least 180 days or six months. In some embodiments, treatment is continued for at least six months to one year. In other embodiments, treatment is continued for the rest of the patient's life or until administration is no longer effective in maintaining the virus at a sufficiently low level to provide meaningful therapeutic benefit.

In accordance with the methods of the invention, some HDV patients will respond to co-therapy herein by clearing virus to undetectable levels, often after experiencing a hepatitis flare, after which treatment may be suspended unless and until the HDV levels return to detectable levels. Other patients will experience a reduction in viral load and improvement of symptoms but will not clear the virus to undetectable levels but will remain on "long term therapy" for so long as it provides therapeutic benefit.

In some cases, a patient is treated to a specified endpoint (e.g., a viral load less than $10^2$ or $10^3$; a hepatitis flare; or clearance of virus) in a first course of treatment. When the patient has achieved the endpoint, the medical provider may elect to discontinue therapy, e.g., lonafarnib-ritonavir co-therapy. Alternatively, when the patient has achieved the endpoint, the medical provider may elect to continue therapy, e.g., lonafarnib-ritonavir co-therapy. For convenience the post-endpoint therapy is sometimes referred to as a "second (or "additional") course of treatment." The first and second courses of therapy may (and typically do) comprise administration of the same dosage regimen (i.e., the same dose and frequency of administration). For avoidance of doubt, although the terminology is sometimes convenient, a patient may receive a "single course of treatment" that extends through an endpoint.

In some embodiments, the patient receiving lonafarnib-ritonavir co-therapy has a baseline viral load of at least $10^4$ HDV RNA copies per mL serum, and treatment results in a viral load of less than $10^2$ HDV RNA copies per mL serum. In some embodiments, a patient having a baseline viral load of at least $10^4$ HDV RNA copies per mL serum receives a first course of treatment that results in a viral load of less than $10^2$ HDV RNA copies per mL serum, and subsequently receives an additional course of treatment, wherein the viral load remains at less than $10^2$ HDV RNA copies per mL serum after the additional course of treatment. In some embodiments, treatment results in an HDV viral load below the level of detection.

In some embodiments, the patient receiving lonafarnib-ritonavir co-therapy has a baseline viral load of at least $10^5$ HDV RNA copies per mL serum, and treatment results in a viral load of less than $10^3$ HDV RNA copies per mL serum. In some embodiments, a patient having a baseline viral load of at least $10^5$ HDV RNA copies per mL serum receives a first course of treatment that results in a viral load of less than $10^3$ HDV RNA copies per mL serum, and subsequently receives an additional course of treatment, wherein the viral load remains at less than $10^3$ HDV RNA copies per mL serum after the additional course of treatment. In some embodiments, the patient receiving lonafarnib-ritonavir co-therapy has a baseline viral load of at least $10^5$ HDV RNA copies per mL serum, and treatment results in a viral load of less than $10^2$ HDV RNA copies per mL serum. In some embodiments, treatment results in an HDV viral load below the level of detection.

In some embodiments, the patient receiving lonafarnib-ritonavir co-therapy has a baseline viral load of at least $10^6$ HDV RNA copies per mL serum, and treatment results in a reduced viral load of less than $10^4$ HDV RNA copies per mL serum, less than $10^3$ HDV RNA, or less than $10^2$ HDV RNA. In some embodiments, the patient receiving lonafarnib-ritonavir co-therapy has a baseline viral load of at least $10^7$ HDV RNA copies per mL serum, and treatment results in a reduced viral load of less than $10^5$ HDV RNA copies per mL serum, less than $10^4$ HDV RNA, or less than $10^3$ HDV RNA, or less than $10^2$ HDV RNA. In some embodiments, treatment results in an HDV viral load below the level of detection.

In some embodiments, treatment with lonafarnib-ritonavir co-therapy results in a reduction of HDV viral load in the patient of at least 1.5 log HDV RNA copies/mL serum when measured after 8 weeks of treatment. In some embodiments, treatment with lonafarnib-ritonavir co-therapy results in a reduction of HDV viral load in the patient of at least 2.0 log HDV RNA copies/mL serum when measured after 8 weeks of treatment. In some embodiments, treatment with lonafarnib-ritonavir co-therapy results in a reduction of HDV viral load in the patient of at least 2.5 log HDV RNA copies/mL serum when measured after 8 weeks of treatment.

In some embodiments, treatment with lonafarnib-ritonavir co-therapy results in a reduction of HDV viral load in the patient of at least −1 log, or at least −2 log, or at least −3 log or at least −5 log, or at least −6 log when measured a number or weeks (e.g. 12, 24, 36, 48, 60, 72 or 90 weeks after the initiation of treatment.

In some embodiments, treatment with lonafarnib-ritonavir co-therapy results in a sustained reduction in HDV RNA levels. For example, in some embodiments, treatment results in a decrease in the level of HDV RNA in the patient's serum or plasma, and this decreased level is sustained for a period of time (e.g., 1 month, 2 months, 3 months, 6 months, 9 months, 1 year, or longer). In some embodiments, a decreased level of HDV RNA is sustained for a period of time (e.g., 1 month, 3 months, 1 year or longer) after a course of treatment is finished. In some embodiments, a decreased level of HDV RNA is sustained for a period of time (e.g., 1 month, 3 months, 1 year or longer) while a course of treatment is still ongoing. In some embodiments, the course of treatment results in HDV RNA levels (e.g., serum HDV RNA levels or plasma HDV RNA levels) below 1,000 copies/mL. In some embodiments, the HDV RNA levels remain below 1,000 copies/mL for at least one month, at least three months, at least one year, or longer. In some embodiments, the course of treatment results in HDV RNA levels (e.g., serum HDV RNA levels or plasma HDV RNA levels) below 100 copies/mL. In some embodiments, the HDV RNA levels remain below 100 copies/mL for at least one month, at least three months, at least one year, or longer. The phrase "remains below" an initial measured value (e.g., 100 copies/mL or 100 IU/mL) for 1 month (or another specified time) means that a viral load measurement taken at least 1 month (or at another specified time) after determination of the initial measured value is no higher than the initial value. In some embodiments, the patient does not receive lonafarnib or lonafarnib-ritonavir co-therapy during the specified time. In some embodiments, the patient does not receive any anti-HDV treatment during the specified time.

In some embodiments, therapy as disclosed herein is continued for a period of time until HDV RNA levels are below 3 log HDV RNA copies/mL (below 1,000 copies/mL), or sometimes until HDV RNA levels are below 2 log HDV RNA copies/mL (below 100 copies/mL) or below the level of detection. In some cases therapy may be continued for a period of time (such as 1 to 3 months or longer) after viral load has dropped to acceptably low levels (e.g., undetectable levels). In some embodiments, therapy is continued until the HDV viral load is reduced to undetectable levels.

In some cases, therapy is continued until a "hepatitis flare" or "ALT flare" is observed in the patient. Hepatitis flares (or acute exacerbations) are an abrupt elevation of serum alanine aminotransferase (ALT) over fivefold the upper limit of normal, about 40 U/L, observed in chronic hepatitis B virus (HBV) infection. HBV flares in HBV patients result from an HLA-I restricted, cytotoxic T lymphocyte (CTL)-mediated immune response against HBV and its downstream mechanisms. Higher ALT levels reflect a more robust immune clearance of HBV. See Liaw, 2003, "Hepatitis flares and hepatitis B e antigen seroconversion: implication in anti-hepatitis B virus therapy," *J Gastroenterol Hepatol* 18:246-52. Hepatitis flares have not previously been reported in response to anti-HDV treatment, but indications of flares have been observed in response to the lonafarnib-ritonavir cotherapy described herein. For example, two patients who received orally administered lonafarnib 100 mg BID and ritonavir 50 mg BID for 12 weeks exhibited ALT flares characterized by ALT levels 10-20 fold higher than a normal individual. ALT flares were also observed in some patients receiving lonafarnib 200 mg BID or 300 mg BID monotherapy, as well as in patients receiving lower doses of lonafarnib in lonafarnib-ritonavir co-therapy (e.g., 75 mg BID lonafarnib in combination with 100 mg BID ritonavir, and 50 mg BID lonafarnib in combination with 100 mg BID ritonavir. See Example 15 below.

The observation of flares in HDV patients suggests that co-therapy with ritonavir and lonafarnib at dosages described herein may have an unprecedented beneficial therapeutic effect in clearing HDV from the patient. Without being bound to a particular theory or mechanism, it is believed that in at least a subset of HDV patients, treatment with lonafarnib or with lonafarnib-ritonavir co-therapy results in a reactivation of the immune system that had been suppressed as a result of infection with HDV virus. Concomitant HBV/HDV infection often results in suppression of HBV replication in human patients and, in at least a subset of HDV patients, suppression of HDV infection using methods described herein results in at least a transient increase in HBV levels. Without being bound to a particular theory, it is also believed that HDV suppresses a patient's immune response in parallel with suppressing HBV; suppression of HDV by lonafarnib treatment releases the suppression of HBV and HBV replication increases. It has been found that some patients who experience immunologic reactivation and who are not receiving any anti-HBV therapy (e.g., antiviral nucleotide or nucleoside analogs) typically exhibit a transient increase of at least 3 log in HBV DNA levels within about 12 weeks from the onset of treatment. See, e.g., Example 15, below. According to the invention, the increase in HBV may be used as a surrogate marker to monitor the extent of immunologic reactivation in response to treatment (e.g., the efficacy of anti-HDV treatment). The ALT flares that are observed in at least a subset of HDV patients in response to HDV treatment, for example as described in Example 15 below, are indicative of a reactivated immune response. Without intending to be bound by a particular mechanism, it is believed that upon immunologic reactivation, the immune system begins to respond to and clear the HDV infection, resulting in the release of ALT from targeted HDV-infected hepatocytes that manifests as an ALT flare. Additionally, for at least some patients, immunologic reactivation can result in a reduction in HBV levels or clearance of HBV infection. As described in Example 15 below, patients from a variety of lonafarnib treatment cohorts who exhibited ALT flares subsequently exhibited suppression or clearance of the HDV infection and a suppression in HBV DNA levels. Without being bound to a particular theory, it is believed that in patients experiencing immunologic reactivation, as evidenced by the presence of ALT flares, suppression of HBV is due at least in part to an immune-mediated response. Thus, while prior to LNF treatment HBV is often suppressed by the HDV, after immunologic reactivation has resulted in suppression or clearance of the HDV, the observed continued or even more pronounced suppression of HBV reflects the newly improved immune-mediated response against HBV.

As described in Example 15 below, it has been found that patients who experience immunologic reactivation exhibit certain characteristics with respect to HDV RNA levels and HBV DNA levels. For example, patients who experience immunologic reactivation typically exhibit a decrease in HDV RNA levels (e.g., of at least 1 log) within the first two weeks of treatment, after which the decreased HDV RNA level is sustained (if not further reduced) for at least another two weeks, before an increase in HDV levels of at least 50% or more from the nadir. In some embodiments, a patient who experiences immunologic reactivation exhibits a transient increase of at least 3 log in HBV viral load.

In some embodiments, the method of inducing immunologic reactivation in the patient comprises administering lonafarnib or lonafarnib-ritonavir co-therapy in a first course of treatment at a first dose, followed by administering lonafarnib or lonafarnib-ritonavir co-therapy in a second course of treatment at a second dose, wherein the second dose is different from the first dose. In some embodiments the second dose is a lower lonafarnib dose (a "step-down"). In some embodiments, the first course of treatment is in the range of about 4-12 weeks, e.g., about 8-12 weeks. In some embodiments, the second course of treatment is about 2-4 weeks. In some embodiments, the first course of treatment is about 8 weeks and the second course of treatment is about 4 weeks.

In some embodiments, within about 12-24 weeks after the occurrence of an ALT flare, the patient is HDV-RNA negative. In some embodiments, within about 12-24 weeks after the occurrence of an ALT flare, the patient has normalized ALT levels (i.e., an ALT level that is within the upper limit of normal as defined in the art). In some embodiments, following the immune reactivation the patient's HDV viral load is reduced by at least 3 log compared to the patient's baseline level at the initiation of treatment. In some embodiments, following the immune reactivation the patient's HBV viral load is reduced by at least 2 log compared to the patient's baseline level at the initiation of treatment. In some embodiments, the patient's HDV viral load and/or HBV viral load is reduced to an undetectable level.

In some embodiments, treatment with lonafarnib-ritonavir co-therapy results in improved liver function in the patient. In some embodiments, the improved liver function is an improvement in one or more liver function parameters (e.g., one, two, three, four, or more parameters) selected from the group consisting of serum albumin, bilirubin, alanine aminotransferase (ALT), aspartate aminotransferase (AST), and prothrombin activity. In some embodiments, treatment results in an improvement of at least 10%, at least 20%, at least 30%, at least 40%, at least 50% or more in one or more liver function parameters selected from the group consisting of serum albumin, bilirubin, ALT, AST, and prothrombin activity. In some embodiments, treatment results in an improvement in one or more liver function parameters selected from the group consisting of serum albumin, bilirubin, ALT, AST, and prothrombin activity to the level of a healthy control subject that is not infected with HDV or HBV. In some embodiments, treatment with lonafarnib-ritonavir co-therapy results in improved liver biopsy (e.g., as assessed by histological staining, immunohistochemical staining, and/or fibrosis grading).

In some embodiments, treatment with lonafarnib-ritonavir co-therapy delays the need for a liver transplant in the patient. In some embodiments, treatment delays the need for a liver transplant for at least 3 months, at least 6 months, at least 9 months, or at least 12 months. In some embodiments, treatment delays the need for a liver transplant indefinitely.

Induction of an ALT Flare and Subsequent Suppression of HDV

In one aspect, methods for inducing an ALT flare in a patient infected with HDV are provided. As discussed herein, in at least some patients with chronic HDV who are treated with lonafarnib therapy (e.g., lonafarnib monotherapy or co-therapy with lonafarnib and ritonavir), an ALT flare is induced that is followed by a significant reduction in HDV RNA titer (see, e.g., FIGS. 26-30). In at least some patients within about 12-24 weeks after the occurrence of an ALT flare, the patient tests negative for HDV RNA. In some patients, a subsequent rise in HDV RNA levels is observed following a period of HDV RNA negativity; without intending to be bound by a particular theory, it is believed that low levels of virus may persist in a "viral reservoir" in a patient who tests negative for HDV RNA using certain assays. In some situations the persistent virus may expand (see, e.g., FIG. 26) and, if not eliminated by the patient's immune response, may require further antiviral treatment. This further antiviral treatment is typically treatment with lonafarnib, optionally as co-therapy with ritonavir and/or interferon. In general, the further treatment comprises administering lonafarnib, optionally as co-therapy with ritonavir and/or interferon, at a lower dose and/or for a shorter duration of time than the initial pre-flare treatment regimen.

For illustration and not limitation, Table 3 shows illustrative treatment protocols.

TABLE 3

| Stage | (A) Duration (D) Dose (O) | (B) Duration (D) Dose (O) | (C) Duration (D) Dose (O) | (D) Duration (D) Dose (O) |
|---|---|---|---|---|
| First Course of Treatment e.g., 2-12 weeks, usually 2-6 weeks | D: 2-12 weeks O: 50 mg BID LNF optionally with 50-100 mg BID RTN | D: 2-12 weeks O: 50 mg BID LNF optionally with 50-100 mg BID RTN | D: 2-4 weeks O: 100 mg BID LNF optionally with 50-100 mg BID RTN | D: 24 weeks O: 50 mg BID LNF optionally with 50-100 mg BID RTN |
| Optional Second course of treatment e.g., 2-12 weeks, usually 2-6 weeks | D: 2-4 weeks* O: 25 mg BID LNF optionally with 50-100 mg BID RTN | D: 2-12 weeks O: 50 mg QD LNF optionally with 50-100 mg BID RTN | D: 2-4 weeks O: 50 mg BID LNF optionally with 50-100 mg BID RTN | None |
| Optional Third course of treatment e.g., 12-60 weeks | D: 12 weeks** O: 25 mg BID LNF optionally with 50-100 mg BID RTN | D: 24 weeks O: 25 mg BID LNF with 50-100 mg BID RTN | D: 24 weeks O: 50 mg BID LNF | None |

*Beginning after the first course of treatment.
**Typically beginning after elevated HDV RNA levels (e.g., >3 log copies/mL) are detected in patients in which an ALT flare was induced and HDV RNA levels were reduced to clinically irrelevant levels, but may also be given prophylactically 2-6 months following initiation of first course of treatment.

As noted above, in addition to or as an alternative to monitoring an ALT flare, HBV DNA levels can be used to assess the efficacy of the initial treatment. As one example, a patient with chronic HDV and a fibrosis score of ≤F3 is administered a first course of treatment of 50 mg BID lonafarnib in combination with 100 mg BID ritonavir for 8 weeks (weeks 1-8). The patient is then administered a second course of treatment of 50 mg QD lonafarnib in combination with 100 mg BID ritonavir for 4 weeks (weeks 9-12). At week 12, the patient's HBV DNA levels is measured. In one approach, if the patient has an HBV DNA increase >3 log, anti-HBV treatment (e.g., using ETV or TNF) is initiated for 36 weeks (weeks 13-48).

If the patient does not show evidence of immunologic reactivation (e.g., has an HBV DNA increase <3 log) the patient receives a course of treatment of anti-HBV treatment (e.g., ETV (or TNF)) in combination with 50 mg BID lonafarnib and 100 mg BID ritonavir for 36 weeks (weeks 13-48).

Reduction of Hepatitis B Virus (HBV) Viral Load

In one aspect, the invention relates to the treatment of a patient with a chronic hepatitis B virus (HBV) infection, in which the course of lonafarnib treatment or lonafarnib-ritonavir treatment (as described herein) results in a reduction of the patient's HBV viral load compared to the baseline level at the initiation of treatment and/or compared to a similarly infected patient not receiving treatment effective to reduce the patient's HDV viral load. See Example 15, below. In some embodiments, the methods for reducing HBV viral load in a patient infected with HBV and HDV comprise administering lonafarnib therapy as described herein and detecting a reduction of at least 1 log in HBV viral load. In some embodiments, treatment results in an at least 2 log reduction of HBV viral load. In some embodiments, the patient is not being treated with antiviral nucleotide or nucleoside analogs.

Without intending to be bound by any theory, it is believed that at least some, if not most, patients will experience a decline in HBV viral load upon receipt of therapy in accordance with the invention, and that some patients, while unable to clear virus on therapy, will maintain the virus at lower levels, relative to not receiving any treatment, and will experience health benefits as a result.

IV. Pharmaceutical Compositions and Unit Dose Forms

In another aspect, the present invention provides unit dose forms and pharmaceutical compositions for providing lonafarnib and ritonavir co-therapy. In some embodiments, the lonafarnib in the unit dose form or pharmaceutical composition is amorphous lonafarnib. In other embodiments, the lonafarnib is crystalline. In some embodiments, the ritonavir in the unit dose form or pharmaceutical composition amorphous ritonavir. In other embodiments, the ritonavir is crystalline. In some embodiments, lonafarnib and ritonavir co-administration is combined with prophylactic administration of one, two or three GI stabilizing agents, as discussed in Section VI below. In some embodiments, lonafarnib and ritonavir co-administration is combined with interferon co-therapy, as discussed in Section V below.

Generally, for convenience, lonafarnib and ritonavir are formulated for oral administration and administered orally. However, in some embodiments, other routes may be preferred, so the present invention provides methods and compositions for the administration of lonafarnib and/or ritonavir to a human for the treatment of HDV infection using one or more other routes, such as administration of intravenous (IV) or subcutaneous (SQ) formulations. As another example, the methods of the invention can be practiced using patch technology, particularly patch technology that employ micro-needles, to administer the drug subcutaneously. Non-oral administration may avoid or at least ameliorate GI and other side effects. Other routes suitable for drug delivery, including systemic and localized routes of administration, may be used.

In many embodiments, however, lonafarnib and/or ritonavir are administered orally in solid dosage forms (e.g., capsules, caplets, tablets, and the like). In certain embodiments, lonafarnib and/or ritonavir are administered orally as soft gel capsules comprising liquid). In some embodiments, lonafarnib and/or ritonavir are administered as a liquid dosage form (oral suspensions, syrups, or elixirs). Liquid dosage forms for oral administration may be provided wherein each dosage unit, for example, teaspoonful, tablespoonful, milliliter, and the like contains a predetermined amount of the composition containing lonafarnib and/or ritonavir. In some embodiments, lonafarnib and ritonavir are administered as a combination of two different dosage forms (e.g., lonafarnib tablet and ritonavir solution).

Lonafarnib and ritonavir may be co-administered separately (as separate unit dosage forms) or may be combined in an oral unit dosage form that comprises both lonafarnib and ritonavir in the practice of the methods described herein. When administered as separate unit forms, typically the lonafarnib and ritonavir doses are administered (e.g., self-administered) at about the same time, e.g., simultaneously or within about 3 minutes of each other, or alternatively, within about 10, 30 or 60 minutes of each other. In some embodiments ritonavir is administered before lonafarnib is administered.

Lonafarnib has been manufactured as 50 mg and 75 mg capsules, but the invention provides, and it is within the ability of those of skill in the art in view of this disclosure to prepare dosage forms with different amounts of the lonafarnib as well as the ritonavir active ingredient. In one embodiment, a pharmaceutical formulation of the invention contains lonafarnib formulated for oral administration as a unit dose form that contains 25 mg, 50 mg, or 75 mg of lonafarnib, including forms from which 50 to 100 mg of ritonavir is also present. If a salt or a solvate is used, equivalent amounts are used will be required as is readily understood by the skilled artisan.

Ritonavir is commercially available as 100-mg tablets, 100-mg soft gelatin capsules and an 80-mg/mL oral solution, but it is within the ability of those of skill in the art in view of this disclosure to prepare dosage forms with different amounts of the active ingredient. In various embodiments, the unit dose form useful in the methods of the invention contains 50 mg or 100 mg or some amount of ritonavir between 50 mg and 100 mg. If a salt or a solvate is used, equivalent amounts are used as is readily understood by the skilled artisan.

Pharmaceutical formulations and unit dose forms suitable for oral administration are particularly useful in the treatment of chronic conditions and therapies in which the patient self-administers the drug. However, as noted above, in some cases (including but not limited to acute infections and life-threatening conditions, particularly those requiring hospitalization) intravenous formulations are desirable, and the present invention provides such formulations as well. The invention provides pharmaceutical formulations in which lonafarnib and/or ritonavir can be formulated into preparations for injection in accordance with the invention by dissolving, suspending or emulsifying the active pharmaceutical ingredients in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Unit dosage forms for injection or intravenous administration may comprise in a composition as a solution in sterile water, normal saline or another pharmaceutically acceptable carrier. Appropriate amounts of the active pharmaceutical ingredient for unit dose forms of lonafarnib and/or ritonavir are provided herein.

Lonafarnib-Ritonavir Co-Formulations

In some embodiments of the invention, lonafarnib and ritonavir are delivered to a patient in the same unit dosage form (i.e., "co-formulated"). For example, a dosage form may contain lonafarnib and ritonavir (along with excipients and auxiliary agents). Without limitation, the lonafarnib and ritonavir may be provided as an admixture, multiparticulate formulation (which may comprise small particles of lonafarnib in a matrix comprising ritonavir), bilayer formulation, a tablet-within-tablet formulation, and the like. Such forms for co-administration are well known for other drugs (see, e.g., US patent publications US 2009/0142393 and US 2008/0021078, and international patent publication WO 2009/042960, each of which is incorporated by reference herein), and such methodology can be used in accordance with this disclosure to prepare suitable unit dosage forms. Liquid formulations containing both lonafarnib and ritonavir as provided herein may also be used for co-administration.

In some embodiments, lonafarnib and ritonavir are formulated with a co-polymer. In some embodiments, the co-polymer is selected from the group consisting of povidone (polyvinylpyrrolidone), hydroxypropyl cellulose, hydroxypropyl methylcellulose (HPMC), hypromellose phthalate, polyvinylpyrrolidone-vinylacetate copolymer, hypromellose-acetate-succinate, and mixtures thereof. In some embodiments, the co-polymer is any one of povidone, hydroxypropyl cellulose, HPMC, hypromellose phthalate, polyvinylpyrrolidone-vinylacetate copolymer, or hypromellose-acetate-succinate. In some embodiments, the co-polymer is a mixture of two or more of povidone, hydroxypropyl cellulose, HPMC, hypromellose phthalate, polyvinylpyrrolidone-vinylacetate copolymer, and hypromellose-acetate-succinate. In some embodiments, the co-polymer is povidone, hydroxypropyl cellulose, or hydroxypropyl methylcellulose (HPMC). In some embodiments, the co-polymer is a polyvinylpyrrolidone-vinylacetate copolymer. In some embodiments, the co-polymer is not povidone.

In some embodiments, the co-polymer is povidone (also known as polyvinylpyrrolidone or PVP). In some embodiments, the co-polymer is polyvinylpyrrolidone K12 (povidone K12), polyvinylpyrrolidone K17 (povidone K17), polyvinylpyrrolidone K25 (povidone K25), polyvinylpyrrolidone K30 (povidone K30), or polyvinylpyrrolidone K90 (povidone K90). In some embodiments, the polyvinylpyrrolidone is polyvinylpyrrolidone K30. In some embodiments, the co-polymer is polyvinylpyrrolidone-vinylacetate copolymer. In some embodiments, the polyvinylpyrrolidone-vinylacetate copolymer is Kollidon® VA 64 copovidone.

In some embodiments, a unit dose form or pharmaceutical composition comprising lonafarnib and ritonavir comprises lonafarnib in an amount from about 20 mg to about 100 mg, e.g., from about 25 mg to about 100 mg, or from about 50 mg to about 100 mg, and comprises ritonavir in an amount from about 50 mg to about 100 mg. In some embodiments, lonafarnib is present in an amount of about 25 mg, about 50 mg, about 75 mg, or about 100 mg, and ritonavir is present in an amount of about 50 mg, about 75 mg, or about 100 mg.

In some embodiments, the unit dose form or pharmaceutical composition is formulated for oral administration and comprises lonafarnib and ritonavir in a ratio of about 1:2 (w/w) or about 1:4 (w/w). In some embodiments, a unit dose form or pharmaceutical composition comprises lonafarnib and ritonavir in a ratio of about 1:2 (w/w). In some embodiments, a unit dose form or pharmaceutical composition comprises lonafarnib and ritonavir in a ratio of about 1:4 (w/w). In some embodiments, a unit dose form or pharmaceutical composition comprises lonafarnib and ritonavir in a ratio of about 0.75:1 (w/w).

In some embodiments, a unit dose form or pharmaceutical composition comprises lonafarnib, ritonavir, and co-polymer in a ratio of about 1:1:2 (w/w), 1:2:3 (w/w), or 1:1:5 (w/w).

In some embodiments, the unit dose form or pharmaceutical composition comprising lonafarnib, ritonavir, and a co-polymer is prepared according to a method described in International Application No. PCT/US2016/028651, incorporated by reference herein. In some embodiments, the unit dose form or pharmaceutical composition is prepared by a process comprising: providing a spray solution of the lonafarnib, ritonavir, and co-polymer in a solvent (e.g., an organic solvent, e.g., dichloromethane, chloroform, isopropyl alcohol, methanol, ethanol, acetone, ethyl methyl ketone, methyl isobutyl ketone, DMSO, water, or a mixture thereof); optionally filtering the spray solution to remove insoluble matter; and substantially removing the solvent form the spray solution. In some embodiments, the solvent is removed by distillation or complete evaporation of the solvent, spray drying, vacuum drying, tray drying, lyophilization or freeze drying, agitated thin-film drying, or a combination thereof.

Defined Release Formulations

Lonafarnib and/or ritonavir dosage forms, including co-formulations comprising lonafarnib and ritonavir, may be formulated for defined release profiles including immediate release and controlled release (e.g., delayed release or sustained release). For example, lonafarnib may be formulated for delayed release and ritonavir may be formulated for immediate release (whether administered as separate or as a combination dosage form(s).

In some embodiments, the unit dosage form or pharmaceutical composition comprising lonafarnib, ritonavir, or lonafarnib and ritonavir as a co-formulation is formulated as a controlled release or delayed release formulation. Methods for making controlled or delayed release formulations are well known in the art. For illustration and not limitation, in some cases, the lonafarnib, and optionally ritonavir, is formulated with a release-delaying agent. Lonafarnib in this formulation may have zero or relatively low release of drug during a lag period after administration to the subject; and then achieves a rapid release ("burst") of drug after the lag period ends. The lag period is typically in the range of about 0.25 to 3 hours, more often in the range of about 0.5 to 2 hours. Many methods are known in the art for providing delayed-burst release, such as by diffusion, swelling, osmotic bursting or erosion (e.g., based on the inherent dissolution of the agent and incorporated excipients); see U.S. Pat. Pub. No. 2011/0313009, incorporated by reference herein.

In some cases, for illustration and not limitation, the release-delaying agent is designed to allow release of lonafarnib and/or ritonavir upon exposure to defined conditions within the body. In one embodiment, the release-delaying agent is an enteric release agent that allows the release of the drug upon exposure to a characteristic aspect of the gastrointestinal tract. In an embodiment, the enteric release agent is pH-sensitive and is affected by changes in pH encountered within the gastrointestinal tract (pH sensitive release). The enteric material typically remains insoluble at gastric pH, then allows for release of the active ingredient in the higher pH environment of the downstream gastrointestinal tract (e.g., often the duodenum, or sometimes the colon). In another embodiment, the enteric material comprises enzymatically degradable polymers that are degraded by bacterial enzymes present in the lower gastrointestinal tract, particularly in the colon. Optionally, the unit dosage form is formulated with a pH-sensitive enteric material designed to result in a release within about 0.25-2 hours when at or above a specific pH. In various embodiments, the specific pH can for example be about 4.5, 5, 5.5, 6, or 6.5. In particular embodiments, the pH-sensitive material allows release of at least 80% of the drug within 1 hour when exposed to a pH of about 5.5 or higher. In another embodiment, the pH-sensitive material allows release of at least 80% of the drug within 1 hour when exposed to a pH of about 6 or higher.

Materials used for enteric release formulations, for example as coatings, are well known in the art, for example, those described in U.S. Pat. Pub. No. 2011/0313009. Combinations of different enteric materials may also be used. Multi-layer coatings using different polymers may also be applied. In some instances, the enteric materials causes a delay of drug release in the range of about 0.25 to about 3 hours, sometimes about 0.5 to about 4 hours.

Those of ordinary skill in the art can adjust the lag period before delayed-burst release from enteric coated multiparticulates by varying the enteric layer coating weight and composition. For example, where time in the stomach is <4 hours and some amount of protection (1-3 hours) is desired after the dosage form leaves the stomach, then an appropriate level of coating that provides up to 4 hours of protection between administration and drug release. can be prepared. To identify the correct coating weight, samples of multiparticulates would be pulled from the fluid bed coater over a range of coating weights and tested via in vitro dissolution to determine the appropriate coating level. Based on these results, the correct coating weight would be selected. An example of an enteric coated multiparticulate can be found in U.S. Pat. No. 6,627,223.

Lonafarnib and/or ritonavir may be mixed with (e.g., blended, intermixed or in continuous phase with) and/or contained within (e.g., encapsulated within or coated with) one or more release-delaying agents. For example, the delayed-burst release formulation can be in the form of one or more capsules containing lonafarnib and/or ritonavir. In other instances, lonafarnib and/or ritonavir can be in multiparticulate form such as granules, microparticles (beads) or nanoparticles, coated with release delaying agents.

As described below in Section VI, in one approach it is contemplated that patients receiving lonafarnib will receive prophylactic administration of one or a combination of GI modifying agent(s). In one approach, one or more GI modifying agents is provided as a co-formulation with lonafarnib and/or ritonavir. For example, without limitation lonafarnib, ritonavir and a GI modifying agent may be formulated as a trilayer tablet. In another approach, one or more GI modifying agents provided in a common pharmaceutical package ("co-packaged"), as described below in Section VII. In one approach the one or more GI modifying agents are provided as an immediate release formulation and lonafarnib (and optionally ritonavir) is provided as a controlled release formulation. The agents formulated with different release may be co-packaged and/or co-formulated in a variety of combinations, provided that at least one GI modifying agent is formulated for rapid release and lonafarnib is formulated for controlled (e.g., delayed) release. In a preferred embodiment, the formulations allow the patient to self-administer lonafarnib and at least one GI modifying agent at substantially the same time (e.g., simultaneously or within about 5 minutes of each other) using formulations that allow the GI modifying agent(s) to take effect prior to release of lonafarnib. Using this approach the patient may have the benefits of pre-release of the GI modifying agent without increasing the number of times per day the patient must self-administer a therapeutic agent.

V. Interferon Co-Therapy

In some embodiments, lonafarnib is used in combination with interferon to treat HDV infection (i.e., HBV and HDV co-infection) or to reduce HDV viral load. In some embodiments, lonafarnib-ritonavir co-therapy is used in combination with interferon to treat HDV infection or reduce HDV viral load.

Human interferons are classified into three major types based on the type of receptor through which they signal. In various embodiments, an interferon of any of Types I-III is used in combination with lonafarnib to treat HDV infection. All type I IFNs bind to a specific cell surface receptor complex known as the IFN-alpha receptor (IFNAR) that consists of IFNAR1 and IFNAR2 chains. The type I interferons present in humans are IFN-alpha, IFN-beta, IFN-epsilon, and IFN-omega. Type II IFNs bind to IFN-gamma receptor (IFNGR) that consists of IFNGR1 and IFNGR2 chains. The type II interferon in humans is IFN-gamma. The recently classified type III interferon group consists of three IFN-lambda molecules called IFN-lambda1, IFN-lambda1 and IFN-lambda3 (also called IL29, IL28A, and IL28B, respectively). These IFNs signal through a receptor complex consisting of IL10R2 (also called CRF2-4) and IFNLR1 (also called CRF2-12). Suitable interferons for use in the treatment methods described herein are described below.

In one embodiment, lonafarnib is administered in combination with other agents, (such as interferon alpha or interferon lambda and optionally ritonavir) at lonafarnib doses of 100 mg QD or less. In one embodiment, the invention provides a method for treating HDV infection by administering at least 50 mg/day of lonafarnib (e.g., 25 mg BID, 50 mg BID, 75 mg BID, 100 mg BID, 50 mg QD, 75 mg QD, or 100 mg QD lonafarnib) in combination with ritonavir and/or an interferon. In one embodiment, the invention provides a method for treating HDV infection by administration of at least 100 mg lonafarnib QD or BID in combination with an interferon and/or ritonavir.

In one approach, the patient receiving lonafarnib (either alone or in combination with a booster such as ritonavir) is also treated with interferon (e.g., interferon alpha or interferon lambda). In some embodiments, both lonafarnib and the interferon (e.g., interferon alpha or interferon lambda) are administered to the patient, and the lonafarnib dose is at least about 25 mg BID, at least about 50 mg BID or QD, at least about 75 mg BID or QD, or about 100 mg BID or QD. In some embodiments, the administration of lonafarnib and the interferon (e.g., interferon alpha or interferon lambda) is concurrent. In some embodiments, the administration of lonafarnib and the interferon (e.g., interferon alpha or interferon lambda) is sequential. In some embodiments, the interferon is interferon alpha. In some embodiments, the interferon alpha is pegylated interferon alpha (e.g., pegylated interferon alpha-2a, also referred to herein as "Pegasys"). In some embodiments, the interferon is interferon lambda. In some embodiments, the interferon lambda is pegylated interferon lambda (e.g., pegylated interferon lambda-1a). Thus, it is contemplated that HDV-infected patients receiving lonafarnib-ritonavir co-therapy may also be treated with an interferon.

Administration of lonafarnib in combination with other agents, such as interferon (e.g., interferon alpha or interferon lambda) and ritonavir (Norvir) provides efficacious therapy at lower doses and/or reduced dosing frequency. Thus, in some cases, the patient is administered with lonafarnib, ritonavir and interferon (e.g., interferon alpha or interferon lambda). In some embodiments, the interferon is administered weekly at a dose of 120 micrograms (mcg) per week or 180 mcg per week.

In some embodiments, interferon alpha (e.g., Pegasys®, Genentech) is administered weekly. In some embodiments, the interferon alpha is administered at a dose of 120 mcg QW or 180 mcg QW. In some embodiments, pegylated interferon (Pegasys®) is administered at a dose of 180 micrograms per week.

In some embodiments, interferon lambda (e.g., pegylated lambda, e.g., pegylated lambda-1a) is administered weekly. In some embodiments, the interferon lambda is administered at a dose of 120 mcg QW or 180 mcg QW. In some embodiments, the interferon lambda is administered at a dose of 120 micrograms per week.

In these embodiments, dosing of lonafarnib (e.g., alone or in combination with ritonavir) and the interferon is continued for at least 30 days, usually at least about 60 or even 90 days or longer, including 6 months to a year or longer. In an approach administration will be continuous for about 30 days, more typically 30 or 60 days, and often as long 6 months, 9 months, and 12 months. In some embodiments, dosing will be discontinued after virus levels have decreased to undetectable levels for a period of time (such as 1 to 3 months or longer).

Interferons

In one aspect, the present invention provides combination therapies in which an interferon-alpha or interferon-lambda are used in combination with lonafarnib. The term "interferon-alpha" or "IFN-α" and "interferon-lambda" or "IFN-λ" as used herein refers to a family of related polypeptides that inhibit viral replication and cellular proliferation and modulate immune response. Suitable interferons for purposes of the invention include, but are not limited to pegylated IFN-α-2a, pegylated IFN-α-2b, consensus IFN, IFN-λ (e.g., IFN-λ1 such as IFN-λ1a), or pegylated IFN-λ (e.g., pegylated IFN-λ1 such as pegylated IFN-λ1a).

Interferon Alpha

The term "IFN-α" includes naturally occurring IFN-α; synthetic IFN-α; derivatized IFN-α (e.g., PEGylated IFN-α, glycosylated IFN-α, and the like); and analogs of naturally occurring or synthetic IFN-α. The term "IFN-α" also encompasses consensus IFN-α. Thus, essentially any IFN-α or IFN-λ that has antiviral properties, as described for naturally occurring IFN-α, can be used in the combination therapies of the invention.

The term "IFN-α" encompasses derivatives of IFN-α that are derivatized (e.g., are chemically modified relative to the naturally occurring peptide) to alter certain properties such as serum half-life. As such, the term "IFN-α" includes IFN-α derivatized with polyethylene glycol ("PEGylated IFN-α"), and the like. PEGylated IFN-α, and methods for making same, is discussed in, e.g., U.S. Pat. Nos. 5,382,657; 5,951,974; and 5,981,709. PEGylated IFN-α encompasses conjugates of PEG and any of the above-described IFN-α molecules, including, but not limited to, PEG conjugated to interferon alpha-2a (Roferon, Hoffman La-Roche, Nutley, N.J.), interferon alpha-2b (Intron, Schering-Plough, Madison, N.J.), interferon alpha-2c (Berofor Alpha, Boehringer Ingelheim, Ingelheim, Germany); and consensus interferon as defined by determination of a consensus sequence of naturally occurring interferon alphas (Infergen®, InterMune, Inc., Brisbane, Calif.).

Thus, in some embodiments of the combination therapies of the invention, the IFN-α has been modified with one or more polyethylene glycol moieties, i.e., pegylated. Two forms of pegylated-interferon, peginterferon alfa-2a (40 kD) (Pegasys®, Genentech) and peginterferon alfa-2b (12 kD) (PegIntron®, Merck), are commercially available, which differ in terms of their pharmacokinetic, viral kinetic, tolerability profiles, and hence, dosing.

Peginterferon alfa-2a (Pegasys®) consists of interferon alfa-2a (~20 kD) covalently linked to a 40 kD branched polyethylene glycol (PEG). The PEG moiety is linked at a single site to the interferon alfa moiety via a stable amide bond to lysine. Peginterferon alfa-2a has an approximate molecular weight of 60,000 daltons. The biologic activity of peginterferon-alfa-2a derives from its interferon alfa-2a moiety which impacts both adaptive and innate immune responses against certain viruses. This alpha interferon binds to and activates human type 1 interferon receptors on hepatocytes which activates multiple intracellular signal transduction pathways, culminating in the expression of interferon-stimulated genes that produce an array of antiviral effects, such as blocking viral protein synthesis and inducing viral RNA mutagenesis. Compared with the native interferon alfa-2a, the peginterferon alfa-2a has sustained absorption, delayed clear. Peginterferon alfa-2a is used as a fixed weekly dose. Peginterferon alfa-2a has a relatively constant absorption after injection and is distributed mostly in the blood and organs.

Peginterferon alfa-2b (PegIntron®) consists of interferon alfa-2b covalently linked to a 12 kD linear polyethylene glycol (PEG). The average molecular weight of the molecule is approximately 31,300 daltons. Peginterferon alfa-2b is predominantly composed of monopegylated species (one PEG molecule is attached to one interferon molecule), with only a small amount of dipegylated species. Fourteen different PEG attachment sites on the interferon molecule have been identified. The biologic activity of peginterferon alfa-2b derives from its interferon alfa-2b moiety, which impacts both adaptive and innate immune responses against certain viruses. This alpha interferon binds to and activates human type 1 interferon receptors on hepatocytes which activates multiple intracellular signal transduction pathways, culminating in the expression of interferon-stimulated genes that produce an array of antiviral effects, such as blocking viral protein synthesis and inducing viral RNA mutagenesis. Compared with the native interferon alfa-2b, the peginterferon alfa-2b has sustained absorption, delayed clearance, and a prolonged half-life. Peginterferon alfa-2b is used as a weekly dose based on the weight of the patient. Peginterferon alfa-2b has a rapid absorption and a wider distribution in the body.

The PEG molecule of a pegylated IFN-α polypeptide is conjugated to one or more amino acid side chains of the IFN-α polypeptide. In an embodiment, the pegylated IFN-α contains a PEG moiety on only one amino acid. In another embodiment, the pegylated IFN-α contains a PEG moiety on two or more amino acids, e.g., the IFN-α contains a PEG moiety attached to two, three, four, five, six, seven, eight, nine, ten, eleven, twelve, thirteen, or fourteen different amino acid residues. IFN-α may be coupled directly to PEG (i.e., without a linking group) through an amino group, a sulfhydryl group, a hydroxyl group, or a carboxyl group.

The term "IFN-α" also encompasses consensus IFN-α. Consensus IFN-α (also referred to as "CIFN" and "IFN-con" and "consensus interferon") encompasses, but is not limited to, the amino acid sequences designated IFN-con1, IFN-con1 and IFN-con3 which are disclosed in U.S. Pat. Nos. 4,695,623 and 4,897,471; and consensus interferon as defined by determination of a consensus sequence of naturally occurring interferon alphas (e.g., Infergen®, Three Rivers Pharmaceuticals, Warrendale, Pa.). IFN-con1 is the consensus interferon agent in the Infergen® alfacon-1 product. The Infergen® consensus interferon product is referred to herein by its brand name (Infergen®) or by its generic name (interferon alfacon-1). DNA sequences encoding IFN-con may be synthesized as described in the aforementioned patents or other standard methods. In an embodiment, at least one additional therapeutic agent is CIFN.

In various embodiments of the combination therapies of the invention, fusion polypeptides comprising an IFN-α and a heterologous polypeptide are used. Suitable IFN-α fusion polypeptides include, but are not limited to, Albuferon-Alpha™ (a fusion product of human albumin and IFN-α; Human Genome Sciences; see, e.g., Osborn et al., 2002, J. Pharmacol. Exp. Therap. 303:540-548). Also suitable for use in the present methods are gene-shuffled forms of IFN-α. See, e.g., Masci et al., 2003, Curr. Oncol. Rep. 5:108-113. Other suitable interferons include Multiferon (Viragen), Medusa Interferon (Flamel Technology), Locteron (Octopus), and Omega Interferon (Intarcia/Boehringer Ingelheim).

In one embodiment of these combination therapies, pegylated interferon alfa-2a (Pegasys) is administered weekly in dosages of 180 microgram (mcg) or 120 mg or 135 mcg (used for patients that react negatively to the higher dose) subcutaneously (SQ). In another embodiment of these combination therapies, pegylated interferon alfa-2b (PegIntron) is administered weekly in dosages of 1.5 mcg/kg/wk SQ. In other embodiments of these methods, alfa-interferons are used as follows: consensus interferon (Infergen) administered at 9 mcg to 15 mcg SQ daily or thrice weekly; interferon-alfa 2a recombinant administered at 3 MIU to 9 MIU SQ administered thrice weekly; interferon-alfa 2b (Intron A) recombinant administered 3 MIU to 25 MIU SQ administered thrice weekly; and pegylated interferon lambda (IL-28) administered at 80 mcg to 240 mcg SQ weekly.

In some embodiments, the interferon is pegylated IFN-alfa 2a or pegylated IFN-alfa 2b. Suitable doses of lonafarnib/pegylated IFN-alfa 2a include, but are not limited to, 100 mg BID/180 mcg QW; 75 mg BID/180 mcg QW; 50 mg BID/180 mcg QW; or 25 mg BID/180 mcg QW. Suitable doses of lonafarnib/pegylated IFN-alfa 2b include, but are not limited to, 100 mg BID/1.5 mcg/kg patient weight QW; 75 mg BID/1.5 mcg/kg patient weight QW; 50 mg BID/1.5 mcg/kg patient weight QW; or 25 mg BID/1.5 mcg/kg patient weight QW.

Interferon Lambda

The term "IFN-λ" encompasses IFN-lambda-1 (which includes IFN-lambda-1a), IFN-lambda-2, and IFN-lambda-3. These proteins are also known as interleukin-29 (IL-29), IL-28A, and IL-28B, respectively. Collectively, these 3 cytokines comprise the type III subset of IFNs. They are distinct from both type I and type II IFNs for a number of reasons, including the fact that they signal through a heterodimeric receptor complex that is different from the receptors used by type I or type II IFNs. Although type I IFNs (IFN-alpha/beta) and type III IFNs (IFN-lambda) signal via distinct receptor complexes, they activate the same intracellular signaling pathway and many of the same biological activities, including antiviral activity, in a wide variety of target cells. Interferon lambda may be administered at any therapeutically appropriate dose, including, without limitation, 80, 120 or 180 mcg QW. In some embodiments, the dose for an adult human is 120 micrograms once per week.

In some embodiments, interferon lambda (e.g., interferon lambda-1 or interferon lambda-1a) is administered in conjunction with lonafarnib, and optionally with ritonavir, for treating a HDV infection in a patient. In some embodiments, the interferon lambda is a pegylated form of interferon lambda (e.g., pegylated interferon lambda-1 or pegylated interferon lambda-1a). In some embodiments, the interferon lambda is an interferon disclosed in U.S. Pat. No. 7,157,559 incorporated by reference herein. In some embodiments, interferon lambda is administered at a dose of 120 micrograms per week. In some embodiments, interferon lambda is administered at a dose of 180 micrograms per week. In some embodiments, the interferon lambda is subcutaneously administered. In some embodiments, interferon lambda therapy is administered in conjunction with lonafarnib, and optionally with ritonavir, for treating a HDV infection in a patient for at least 1 month, 2 months, 3 months, 4 months, 5 months, 6 months or longer. Example 15 describes a prophetic example of administering interferon lambda in combination with lonafarnib and, optionally, ritonavir.

In some embodiments, the interferon is pegylated IFN lambda-1a. Suitable doses of lonafarnib/pegylated IFN lambda-1a include, but are not limited to, 100 mg BID/180 mcg QW; 75 mg BID/180 mcg QW; 50 mg BID/180 mcg QW; 25 mg BID/180 mcg QW; 100 mg BID/120 mcg QW; 75 mg BID/120 mcg QW; 50 mg BID/120 mcg QW; or 25 mg BID/120 mcg QW.

Triple Therapy

In some embodiments, interferon lambda as described herein is administered in combination with lonafarnib and ritonavir for treating a HDV infection in a patient. In some embodiments, the lonafarnib dose is 50 mg BID, the ritonavir dose is 100 mg BID, and the interferon lambda dose is 120 mcg QW. In some embodiments, the lonafarnib dose is 50 mg BID, the ritonavir dose is 100 mg BID, and the interferon lambda dose is 180 mcg QW. In some embodiments, the lonafarnib dose is 25 mg BID, the ritonavir dose is 100 mg BID, and the interferon lambda dose is 120 mcg QW. In some embodiments, the lonafarnib dose is 25 mg BID, the ritonavir dose is 100 mg BID, and the interferon lambda dose is 180 mcg QW. In some embodiments, the lonafarnib dose is 75 mg BID, the ritonavir dose is 100 mg BID, and the interferon lambda dose is 120 mcg QW. In some embodiments, the lonafarnib dose is 75 mg BID, the ritonavir dose is 100 mg BID, and the interferon lambda dose is 180 mcg QW. In some embodiments, the lonafarnib dose is 50 mg QD, the ritonavir dose is 100 mg QD, and the interferon lambda dose is 120 mcg QW. In some embodiments, the lonafarnib dose is 50 mg QD, the ritonavir dose is 100 mg QD, and the interferon lambda dose is 180 mcg QW. In some embodiments, the lonafarnib dose is 75 mg QD, the ritonavir dose is 100 mg QD, and the interferon lambda dose is 120 mcg QW. In some embodiments, the lonafarnib dose is 75 mg QD, the ritonavir dose is 100 mg QD, and the interferon lambda dose is 180 mcg QW. In some embodiments, the lonafarnib dose is 100 mg QD, the ritonavir dose is 100 mg QD, and the interferon lambda dose is 120 mcg QW. In some embodiments, the lonafarnib dose is 100 mg QD, the ritonavir dose is 100 mg QD, and the interferon lambda dose is 180 mcg QW.

VI. Prophylaxis With Gastrointestinal Modifying Therapies

As described in Example 2 and Example 4, below, some HDV-infected patients receiving lonafarnib monotherapy and lonafarnib-ritonavir co-therapy experienced gastrointestinal (GI) side effects. GI side effects are not unexpected of compounds in the farnesyl transferase class. GI intolerance is also a known side-effect of ritonavir, even though ritonavir may be dosed at doses as high as 1200 mg/day when used as a protease inhibitor. However, the severity and persistence of these symptoms in HDV patients receiving lonafarnib given the comparatively modest doses of lonafarnib and ritonavir was unexpected. Agents for treatment of gastrointestinal irritations include anti-emetics, antacids (H2-receptor antagonists and proton pump inhibitors) and anti-diarrheals. Exemplary agents (for illustration and not limitation) are listed in Table 4 below.

In accordance with the methods of the present invention, lonafarnib is used in combination with at least one, at least two, or at least three of an anti-emetic, an antacid (H2-receptor antagonist or proton pump inhibitor) and/or an anti-diarrheal to allow for continued compliance of patients while on lonafarnib therapy. In one embodiment, an anti-diarrheal agent is administered. In one embodiment, an anti-diarrheal agent and an antacid are administered. In one embodiment, an anti-diarrheal agent and an anti-emetic are administered. In one embodiment, an anti-diarrheal agent, an antacid and an anti-emetic are administered. In one embodiment, the anti-diarrheal agent is lomotil (atropine/diphenoxylate) and/or the antacid is famotidine and/or the antiemetic is ondansetron.

TABLE 4

Exemplary GI Modifying Agents

| Class | Exemplary agents |
|---|---|
| Anti-emetics | 5-HT$_3$ antagonists (such as ondansetron (Zofran ®), tropisetron (Navoban ®), granisetron (Kytril ®), palonosetron (Aloxi ®), and dolasetron (Anzemet ®)) and NK1 receptor antagonists (such as aprepritant (Emend ®), casopitant, and fosaprepitant (Emend ® IV)). |
| Antacids | H2-receptor antagonists (such as ranitidine (Zantac ®), famotidine (Pepcid ®), cimetidine (Tagamet ®) and nizatidine (Axid ®) and Proton pump inhibitors (such as omeprazole (Prilosec ®), omeprazole/sodium bicarbonate (Zegerid ®), esomeprazole magnesium (Nexium ®), esomeprazole strontium, lansoprazole (Prevacid ®), dexlansoprazole (Dexilant ®), rabeprazole, and pantoprazole sodium (Protonix ®)). |
| Anti-diarrheals | atropine/diphenoxylate (Lomotil ®, Lonox ®), loperamide HCl (Imodium ®), and bismuth subsalicylate (Kaopectate ®, Pepto-Bismol ®). |

In one approach, GI modifying therapies are administered on an as-needed basis (in response to symptoms). In one approach, GI modifying therapies are administered prophylactically. As used herein in this context, "prophylactically" refers to administration to a patient in the absence of, or before development of, symptoms. Typically prophylactic treatment entails administration according to a fixed schedule (e.g., daily) during the course of lonafarnib treatment.

In one approach, prophylactic treatment comprises administration of ondansetron (anti-emetic), lomotil (atropine/diphenoxylate) (anti-diarrheal) and famotidine (antacid). For example, ondansetron may be administered 8 mg BID, lomotil (atropine/diphenoxylate) may be administered 5 mg QID or 5 mg BID, and famotidine may be administered 20 mg BID.

In one approach, the GI modifying agents are administered daily, prior to administration of lonafarnib. In one approach GI modifying agents are administered 30 minutes to two hours before administration of lonafarnib therapy.

In one approach, the GI modifying agents are administered daily at the same time lonafarnib is administered, but lonafarnib (and optionally ritonavir) are administered as a delayed release formulation (e.g. comprising an enteric coating) so that the GI modifying agents begin to take effect prior to lonafarnib release.

Prophylactic administration of GI modifying agents is generally continued for the duration of lonafarnib therapy.

In one approach, prophylactic administration of GI modifying agents commences on the first day of lonafarnib administration. In another approach, administration of one or more of the GI modifying agents commences prior to initiation of oral lonafarnib-ritonavir therapy. For example, in one embodiment the patient takes ondansetron the day before the start of lonafarnib treatment. In one approach, one or more GI modifying agents are administered daily beginning more than one day before initiation of oral lonafarnib-ritonavir treatment.

In a preferred embodiment, a GI modifying agent is administered according to a BID or QD schedule.

H2-Receptor Antagonists

In one embodiment of the GI modifying therapies, the GI modifying therapy is an H2-receptor antagonist. In one embodiment of the GI modifying therapies, ranitidine (Zantac®) is administered at a dose of 150 mg twice daily, up to 150 mg four times daily for the duration of lonafarnib therapy. In another embodiment of these GI modifying therapies, famotidine (Pepcid®) is administered at a dose of 40 mg once daily, up to 20 mg twice daily, up to 40 mg twice daily for the duration of lonafarnib therapy. In another embodiment of the GI modifying therapies, cimetidine (Tagamet®) is administered at dose of 400 mg once daily, up to 800 mg once daily, up to 1600 mg once daily, up to 800 mg twice daily, up to 300 mg four times daily, up to 400 mg four times daily, up to 600 mg four times daily for the duration of lonafarnib therapy. In another embodiment of the GI modifying therapies, nizatidine (Axid®) is administered at dose of 150 mg once daily, up to 300 mg once daily, up to 150 mg twice daily for the duration of lonafarnib therapy.

5-HT$_3$ Antagonists

In one embodiment of the GI modifying therapies, the therapy is a 5-HT$_3$ receptor antagonist. In one embodiment of the GI modifying therapies, ondansetron (Zofran®) is administered 30 minutes to two hours before the start of lonafarnib therapy at 8 mg once daily, up to 8 mg two times daily, up to 8 mg three times daily. In this embodiment, administration is continued at least for the duration of lonafarnib treatment. In another embodiment of the GI modifying therapies, granisetron (oral Kytril®) is administered at 2 mg given up to one hour before the start of lonafarnib therapy or 1 mg twice daily. In this embodiment, administration is continued at least for duration of lonafarnib treatment.

NK-1 Receptor Antagonists

In one embodiment of the GI modifying therapies, the GI modifying therapy is an NK-1 receptor antagonist. In one embodiment of the GI modifying therapies, aprepitant (Emend®) is administered in combination with an 5-HT3 receptor antagonist and a corticosteroid as a three day treatment consisting of a 125 mg dose on day one given one hour before start of lonafarnib therapy, followed by an 80 mg dose on days two and three. In another embodiment of the GI modifying therapies, fosaprepitant (Emend® IV) is administered in combination with an 5-HT3 receptor antagonist and a corticosteroid (dexamethasone) as a single day treatment consisting of one 150 mg dose of fosaprepitant given up to 30 minutes before start of lonafarnib therapy followed by a single 12 mg dose of dexamethasone and a single dose of a 5-HT3 receptor antagonist such as odansetron, up to a single 150 mg dose of fosaprepitant given up to 30 minutes before start of lonafarnib therapy followed by a single 8 mg dose of dexamethasone and a single dose of a 5-HT3 receptor antagonist such as ondansetron on day one, and a single 8 mg dose of dexamethasone on days 2 through 4.

Proton Pump Inhibitors

In one embodiment of the GI modifying therapies, the GI modifying therapy is a proton pump inhibitor (PPI). In one embodiment of the GI modifying therapies, omeprazole (Prilosec®) is administered in combination with an antacid up to four days before the start of lonafarnib therapy at a dose of 20 mg once daily, up to 40 mg once daily for the duration of lonafarnib therapy. In another embodiment of the GI modifying therapies, omeprazole/sodium bicarbonate (Zegerid®) is administered at least one hour before a meal and before the start of lonafarnib therapy at a dose of 20 mg once daily, up to 40 mg once daily for the duration of lonafarnib therapy. In another embodiment of the GI modifying therapies, esomeprazole magnesium (Nexium®) is administered at least one hour before lonafarnib treatment at dose of 20 mg once daily, up to 40 mg once daily, up to 40 mg twice daily for the duration of lonafarnib therapy. In another embodiment of the GI modifying therapies, esomeprazole strontium is administered at least one hour before lonafarnib treatment at dose of 24.65 mg once daily, up to 49.3 mg once daily, up to 49.3 mg twice daily, for the duration of lonafarnib therapy. In another embodiment of the GI modifying therapies, lansoprazole (Prevacid®) is administered up to two hours before lonafarnib therapy at a dose of 15 mg once daily of lansoprazole, up to 30 mg once daily, up to 60 mg once daily, up to 30 mg two times daily for a duration up to 14 days, up to 30 mg three times daily for the duration of lonafarnib therapy. In another embodiment of the GI modifying therapies, dexlansoprazole (Dexilant®) is administered up to two hours before lonafarnib therapy at a dose of 30 mg once daily of dexlansoprazole, up to 60 mg once daily for the duration of lonafarnib therapy. In another embodiment of the GI modifying therapies, pantoprazole sodium (Protonix®) is administered up to seven days before lonafarnib therapy at a dose of 40 mg once daily, up to 40 mg twice daily for the duration of lonafarnib therapy.

In some embodiments of the invention, the GI modifying therapy includes administration of a proton pump inhibitor (PPI) selected due to its inhibitory effect on CYP3A4. PPI-mediated inhibition can assist in maintaining therapeutically effective lonafarnib serum levels. Such inhibitory PPIs include, without limitation, omeprazole and rabeprazole.

Anti-Diarrheal Agents

In one embodiment of the GI modifying therapies, the therapy is an anti-diarrheal. In one embodiment of the GI modifying therapies, atropine/diphenoxylate (Lomotil®, Lonox®) is administered at a dose of two Lomotil tablets four times daily or 10 ml of Lomotil® liquid four times daily (20 mg per day) until initial control has been achieved, after which the dosage may be reduced to as little as 5 mg (two tablets or 10 ml of liquid) daily. In another embodiment of the GI modifying therapies, loperamide HCl (Imodium®) is administered at a dose of 4 mg (two capsules) followed by 2 mg (one capsule) after each unformed stool, up to 16 mg (eight capsules). In another embodiment of the GI modifying therapies, bismuth subsalicylate (Kaopectate®, Pepto-Bismol®) is administered as 2 tablets or 30 mL every 30 minutes to one hour as needed, up to eight doses in 24 hours.

VII. Kits and Packaging

Lonafarnib, and/or ritonavir, and/or an interferon and/or one or more GI modifying agents, for use in treating HDV and/or HBV patients, may be delivered in a pharmaceutical package or kit to doctors and patients, e.g., HDV patients. Such packaging is intended to improve patient convenience and compliance with the treatment plan. Typically the packaging comprises paper (cardboard) or plastic. In some embodiments, the kit or pharmaceutical package further comprises instructions for use (e.g., for administering according to a method as described herein).

In some embodiments, a pharmaceutical package or kit comprises unit dose forms of lonafarnib comprising 25, 50, 75, or 100 mg lonafarnib per unit dose, or an amount between 25 mg and 100 mg lonafarnib per unit dose, and unit dose forms of ritonavir comprising 50 mg or 100 mg ritonavir per unit dose, or an amount between 50 mg and 100 mg ritonavir per unit dose. In some embodiments, the pharmaceutical package or kit further comprises, or comprises instead of ritonavir, unit dose forms of interferon. In some embodiments, the pharmaceutical package or kit comprises unit dose forms of interferon comprising 120 mcg or 180 mcg interferon (e.g., pegylated interferon lambda-1a) per unit dose. In some embodiments, the pharmaceutical package or kit further comprises unit dose forms of one or more GI modifying agents (e.g., one or more anti-emetics, antacids (H2-receptor antagonists and proton pump inhibitors) or anti-diarrheal agents).

In one embodiment, the kit or pharmaceutical package comprises lonafarnib and ritonavir in defined, therapeutically effective doses in combination in a single unit dosage form or as separate unit doses. The dose of each drug (e.g., in mg) and the form of the unit dose (e.g., tablet, capsule, immediate release, delayed release, etc.) can be any doses or forms as described herein (e.g. Section IV).

In one embodiment, the kit or pharmaceutical package includes doses suitable for multiple days of administration, such as one week, one month, or three months. In a preferred approach, in multi-day packs the doses (e.g., tablets) for each administration (e.g., once per day for QD administration, twice per day for BID administration, etc.) are separated from doses to be administered on different days or at different times.

In another embodiment, the package comprises defined therapeutically effective doses of lonafarnib, ritonavir, or a combination of lonafarnib and ritonavir, and one or more GI modifying agents, which are combined in a single package, but segregated from one another in separate compartments within said package.

VIII. Other Antiviral Therapies

It is contemplated that HDV-infected patients receiving lonafarnib-ritonavir co-therapy may also be treated with other antiviral agents such nucleoside and nucleotide analogues, compounds used to treat HBV infections, and other agents.
Nucleoside and Nucleotide Analogs Antiviral nucleoside or nucleotide analogues that may be used in combination with the lonafarnib-ritonavir cotherapy described herein include such as adefovir (Hepsera®), entecavir (Baraclude®), lamivudine (Epivir-HBV®, Heptovir®, Heptodin®), telbivudine (Tyzeka®), tenofovir (Viread®), and ribavirin (such as Rebetol® or Copegus®).
Compounds Used to Treat HBV In various combination therapies of the invention, for treatment of HDV, lonafarnib is combined with an antiviral medication directed against HBV. Anti-HBV medications that are currently approved, with the exception of interferons, inhibit reverse transcriptase and are nucleoside or nucleotide analogues. These medications, while effective against HBV, are not effective against HDV as they do not clear HBsAg, which HDV needs to replicate; however, when used in the combination therapies of the invention, improved patient outcomes can be achieved. Currently approved anti-HBV medications include: interferon alpha (Intron A®), pegylated interferon (Pegasys®), lamivudine (Epivir-HBV®, Zeffix®, or Heptodin®), adefovir dipivoxil (Hepsera®), entecavir (Baraclude®), telbivudine (Tyzeka®, Sebivo®), clevudine (Korea/Asia), tenofovir (Viread®). Truvada®, which is a combination of tenofovir and emtricitabine, is not yet approved but has been shown to be effective in reducing HBV viral titers in early clinical trials and is useful in the combination therapies of the invention.
Other Therapeutic Compounds Other therapeutic compounds that may be administered with beneficial effect to an HDV-infected patient that is being treated in accordance with the invention include a nucleoside or nucleotide analog; a thiazolide; a protease inhibitor; a polymerase inhibitor; a helicase inhibitor; a Class C CpG toll-like receptor 7 and/or 9 antagonist; an amphipathic helix disruptor or NS4B inhibitor; a statin or other HMG CoA reductase inhibitor; an immunomodulator; an anti-inflammatory; a second prenylation inhibitor; a cyclophilin inhibitor; and an alpha-glucosidase inhibitor.
Other Therapeutic Modules Oral lonafarnib-ritonavir co-therapy may be one module in a course of therapies for rapid and complete clearance of HDV infection. Thus, the treatment regimens described herein may be preceded by or followed by complementary therapies.

As one example, some patients may benefit from an initial IV infusion of lonafarnib to achieve high blood levels of the drug rapidly, which levels may be sustained by continuous or periodic IV infusion(s) for some period (one to a few days or perhaps a week) before a patient is placed on the oral therapies more specifically described herein. In these embodiments, a patient may be infused with the drug to achieve the therapeutic efficacy associated with serum levels achieved with 50 mg BID administration (and higher doses). The IV administration is done under the care of a physician other trained medical professional (for example, in a hospital), with the prophylactic therapy and monitoring to avoid or ameliorate the AEs associated with oral dosing at those high doses or to discontinue IV administration, if necessary. In other embodiments, subcutaneous infusions to provide a depot form of the drug that maintains therapeutically effective blood levels of the drug for some days or weeks may be used to achieve the same therapeutically effective results as those described herein for oral therapy.

IX. Use of Cobicistat as Boosting Agent

While ritonavir is the most widely used CYP3A4 inhibitor, the invention also provides lonafarnib combination treatments and therapies with other CYP3A4 inhibitor inhibitors. In one alternative, the invention provides embodiments, described elsewhere herein as well, in which the pharmacokinetic boosting agent cobicistat is used in combination with lonafarnib in place of ritonavir.

Cobicistat (marketed under the tradename Tybost® by Gilead Sciences) is a potent inhibitor of CYP3A. As does ritonavir, it "boosts" blood levels of other substrates of this enzyme but, unlike ritonavir, it has no anti-viral activity. In addition, while it has a pronounced effect on the enzyme system (CYP3A) responsible for breaking down certain drugs, it does not affect other enzyme systems used by many other medications which may contribute to numerous potentially harmful drug interactions.

In one aspect, the invention provides treatment of HDV patients using the methods and compositions described herein, except that a boosting agent other than ritonavir is used. In one embodiment the boosting agent cobicistat is used in the methods and compositions described herein. Cobicistat is useful in the combination therapies of the invention at its approved or any lower dose in combination with lonafarnib at any dose and dosing frequency described herein. In alternative embodiments cobicistat is administered at a lower (e.g., 75 mg) and/or more frequent (e.g., BID) dose than has been approved for use in the treatment of HIV infection. In some embodiments, a lower dose of cobicistat is used (e.g., 50 mg QD or 50 mg BID).

Exemplary doses for lonafarnib-cobicistat co-therapy, for illustration and not for limitation, are provided in Table 5 below. In some embodiments, lonafarnib is dosed at 100 mg QD or 100 mg BID and cobicistat (Tybost®) is administered at 150 mg once daily.

Each of dosing schedules A-G may be administered with prophylactic GI modifying agents (e.g., an anti-emetic agent, an anti-diarrheal agent, and an antacid), and/or with an interferon (e.g., interferon alpha or interferon lambda). See Section V and Section VI above. In one embodiment, lonafarnib-cobicistat co-therapy is administered in combination with an interferon.

TABLE 5

| | A | B | C | D | E | F | G |
|---|---|---|---|---|---|---|---|
| Dose lonafarnib | 100 mg BID | 75 mg BID | 50 mg BID | 25 mg BID | 100 mg QD | 50 mg QD | 75 mg QD |
| Dose cobicistat | 150 mg QD | 150 mg QD | 150 mg QD | 150 mg QD | 150 mg QD | 150 mg QD | 150 mg QD |

X. Examples

The following examples are offered to illustrate, but not to limit, the claimed invention.

Example 1. Treating HDV Patients with 100 mg Lonafarnib Administered BID

This example demonstrates lonafarnib's efficacy to reduce HDV RNA levels in patients with chronic HDV. The eight Group 1 patients (all with chronic HDV) were treated as follows: 6 patients (patients 1, 2, 4, 5, 6, and 8) with chronic delta hepatitis (HDV) were treated with lonafarnib and 2 patients (patients 3 and 7) were administered placebo for a duration of twenty-eight days. The 6 patients in the active treatment group were dosed at 100 mg BID (orally administered) for 28 days. The mean change in HDV RNA levels from baseline to nadir in the lonafarnib active treatment group was −0.74 log HDV RNA copies/mL and in the placebo group was −0.24 log HDV RNA copies/mL.

Patients 4, 5, 6 and 8 were responsive to therapy, as defined by greater than or equal to a 0.5 log HDV RNA copies/mL decline in quantitative serum HDV RNA levels from baseline to nadir during active treatment. See Table 6 (showing change in HDV RNA viral load for each patient, during treatment and post-treatment) and FIG. 1 (showing the time course of the log HDV RNA copies/mL levels of patients 4, 5, and 6). The change in patient 4's HDV RNA levels from baseline to the end of the treatment (EOT) was −1.34 log HDV RNA copies/mL. The change in patient 5's HDV RNA levels from baseline to EOT was −0.82 log HDV RNA copies/mL. The change in patient 6's HDV RNA levels from baseline to EOT was −1.41 log HDV RNA copies/mL.

HDV RNA Viral Load Correlates with Plasma Concentrations of Lonafarnib.

FIG. 2 illustrates the correlation between plasma levels of lonafarnib and viral load. Patients with higher plasma levels of lonafarnib experienced greater declines in HDV RNA titers during treatment. Plasma levels ranged between 200 ng/mL and 1,100 ng/mL during treatment.

Post-Treatment Viral Rebound

Patients 4, 5, and 6 exhibited viral rebound or an increase in serum HDV RNA levels after lonafarnib therapy was discontinued on day 28. Patient 4's HDV RNA level increased 1.7 log HDV RNA copies/mL after discontinuation of lonafarnib. Patient 5's HDV RNA level increased 1.4 log HDV RNA copies/mL after discontinuation of lonafarnib. Patient 6's HDV RNA level increased after discontinuation of lonafarnib. Patients 4, 5, and 6 exhibited subsequent decreases in HDV RNA levels, beginning approximately 4-8 weeks after lonafarnib therapy was discontinued, which is considered to be attributed to virus to virus dynamics between HDV RNA and HBV DNA.

Example 2. Treating HDV Patients with 200 mg and 300 mg Lonafarnib Administered BID Six human subjects known to be infected with HDV, as documented by baseline HDV RNA viral titers ranging from 5.8 log HDV RNA copies/mL to 8.78 log HDV RNA copies/mL, were treated with lonafarnib at doses of either 200 mg BID or 300 mg BID for a period of 84 days.

Effect of 28 Days Treatment

Figure 3:
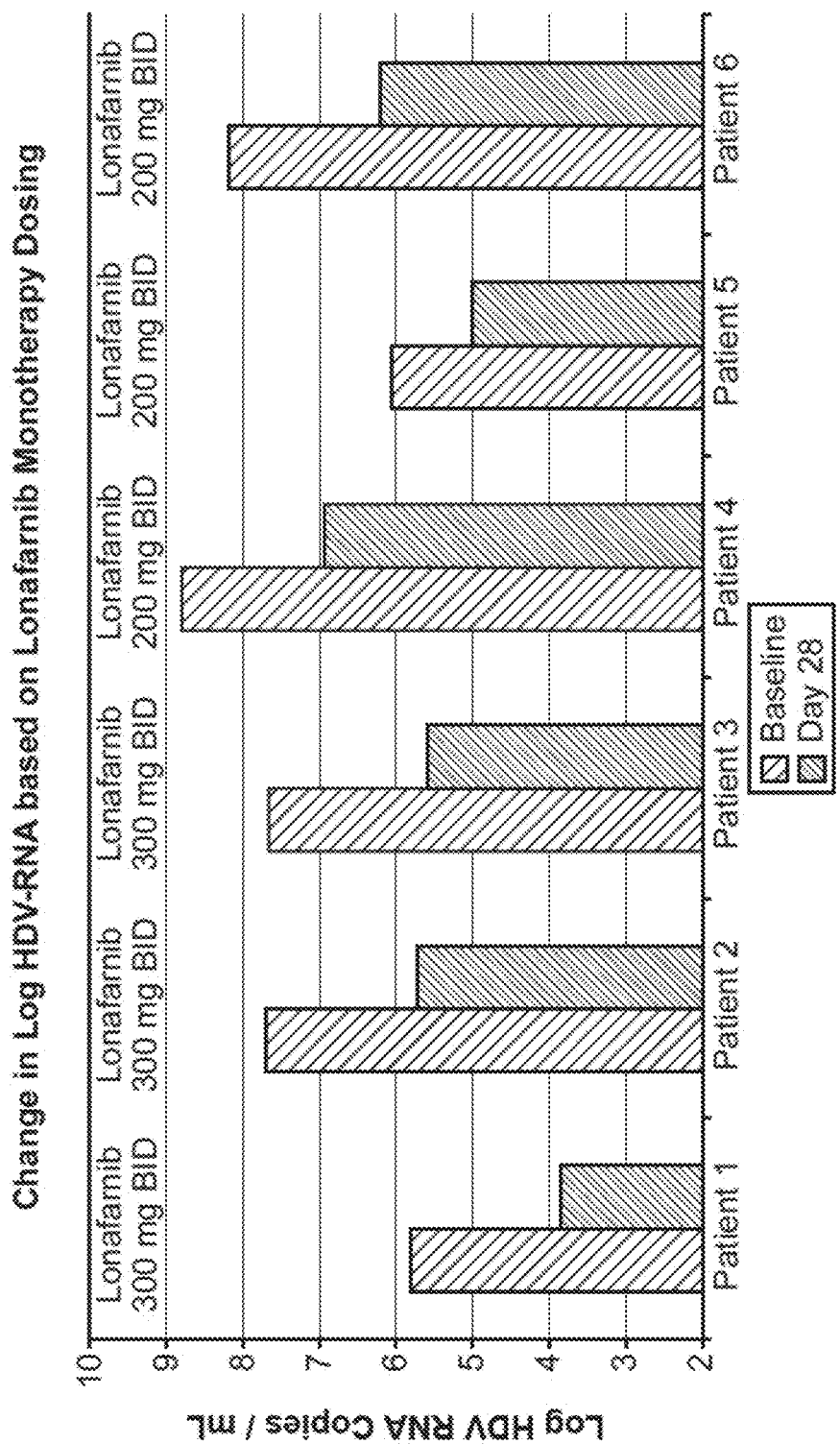
FIG. 3. HDV RNA viral titers in human patients treated with lonafarnib in doses of either 200 mg BID or 300 mg BID for a period of 28 days. See Example 2.

At the end of 28 days of treatment, the mean change in viral load across the six subjects from baseline to day 28 was −1.63 log copies/mL for the 200 mg BID group and −2.00 log copies/mL for the 300 mg BID group. See Table 7 and FIG. 3.

TABLE 6

| | 100 mg BID Lonafarnib Monotherapy Baseline vs EOT on Rx vs Post | | | | | | | |
|---|---|---|---|---|---|---|---|---|
| | Patient 1 | Patient 2 | Patient 4 | Patient 5 | Patient 6 | Patient 8 | Patient 3 | Patient 7 |
| Dose lonafarnib (mg BID) | 100 | 100 | 100 | 100 | 100 | 100 | Placebo | Placebo |
| Composite Baseline (log copies/mL) | 7.33 | 8.08 | 7.77 | 8.59 | 8.78 | 7.19 | 7.29 | 8.33 |
| Change log Baseline to EOT | −0.20 | −0.19 | −1.34 | −0.82 | −1.41 | −0.46 | −0.29 | −0.14 |
| Change log Baseline to post-FU | −0.10 | +0.27 | −0.16 | −0.43 | −1.63 | +0.20 | −0.10 | −0.13 |

TABLE 7

| | 300 mg BID lonafarnib | | | 200 mg BID lonafarnib | | |
|---|---|---|---|---|---|---|
| | Patient 1 | Patient 2 | Patient 3 | Patient 4 | Patient 5 | Patient 6 |
| HDV RNA viral load baseline (log copies/mL) | 5.8 | 7.7 | 7.66 | 8.78 | 6.06 | 8.19 |
| Δ log Baseline to Day 28 | −1.95 | −1.97 | −2.07 | −1.85 | −1.06 | −1.98 |

The results at Day 28 demonstrated superior efficacy of the 200 mg BID and 300 mg BID administration schedule over the 100 mg BID administration schedule. However, additional efficacy with fewer side effects was believed to be required for significant therapeutic benefit.

Effect of 56-84 Day Treatment

When 200 mg BID and 300 mg BID dosing was continued for 56 days (days 29-56 may be referred to as Month 2) and 84 days (days 57-84 may be referred to as Month 3), the change in viral loads across the six patients either plateaued or increased from viral load levels at 28 days. This no change or rise in viral loads was attributed to poor gastrointestinal tolerance to lonafarnib and associated poor compliance with protocol. These six patients did not receive GI modifying agents prophylactically to mitigate gastrointestinal distress. It is likely that compliance or drug absorption or both were suboptimal due to GI intolerance and attendant side effects.

Example 3. Combination Treatment of HDV Patients with 100 mg BID Lonafarnib and Interferon Three human subjects known to be infected with HDV, as documented by baseline HDV RNA viral titers ranging from 4.34 log HDV RNA copies/mL to 5.15 log HDV RNA copies/mL and ALT values ranging from 155-174 IU/L, were treated with lonafarnib in doses of 100 mg BID in combination with Pegasys® (peg interferon alfa-2a) 180 µg per week for a period of 56 days (2 months).

At the end of 28 days, all three patients' HDV RNA viral titers had decreased from baseline, ranging from −1.04 log HDV RNA copies/mL to −2.00 log HDV RNA copies/mL drop in HDV-RNA, with an average drop across the three subjects of −1.8 log HDV RNA copies/mL. At the end of 56 days, all three patients' HDV RNA viral titers continued to decline with a mean viral load decline of 3 log copies/mL at day 56. In addition, the ALT values of all three patients decreased from baseline through day 56, continuing to decline after therapy was stopped, normalizing in two of three patients by post week 4 of treatment cessation. Upper limit of normal for ALT values is estimated to be 40 U/L.

Figure 4:
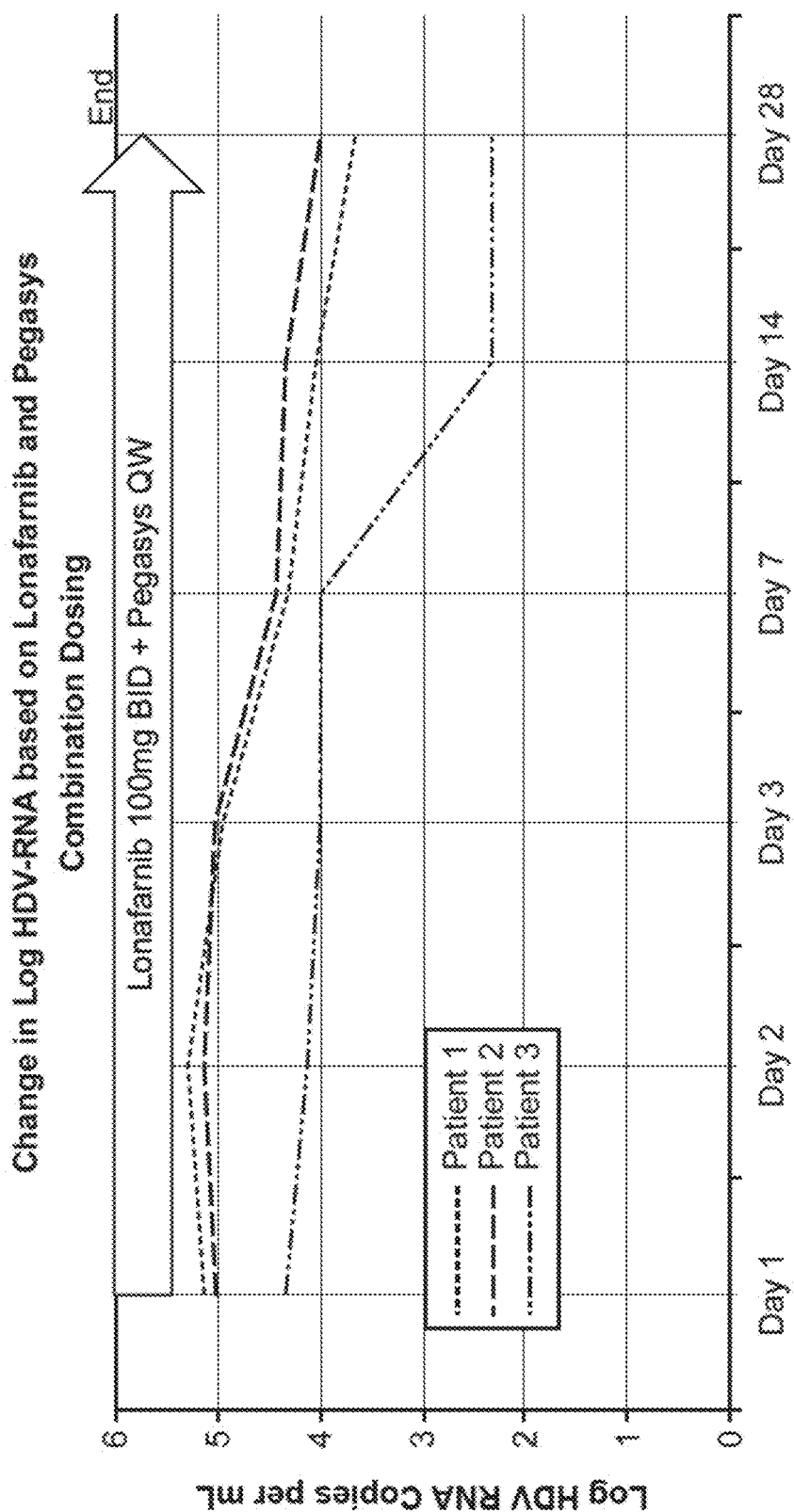
FIG. 4. Changes in HDV RNA viral titers in patients treated with lonafarnib and interferon (Pegasys) at doses described in Example 3.

The change in HDV RNA viral load and ALT values for each patient is tabulated below in Table 8. See also FIG. 4.

TABLE 8

| Combination therapy of lonafarnib 100 mg BID and PEG IFN 180 mcg QW | | | | | | | |
|---|---|---|---|---|---|---|---|
| | Log HDV RNA copies/mL | | | | | | ALT (U/L)* |
| Patient | Day 1 | Day 2 | Day 3 | Day 7 | Day 14 | Day 28 | Change | Day 1 to Day 28 to Day 56 to Post Wk 4** |
| 1 | 5.15 | 5.28 | 4.98 | 4.32 | 4.04 | 3.64 | −1.51 | 161→73→66→28 |
| 2 | 5.04 | 5.15 | 5.04 | 4.43 | 4.34 | 4.00 | −1.04 | 174→144→69→55 |
| 3 | 4.34 | 4.15 | 4.04 | 4.04 | 2.34 | 2.34 | −2.00 | 155→80→56→40 |

*Upper limit of normal = 40 U/L
**Post Wk 4 refers to the end of the first week following termination of treatment.

These viral load results demonstrate comparable efficacy to the 200 mg BID lonafarnib regimen and superior efficacy over the 100 mg BID lonafarnib regimen and fewer grade 2 adverse events (AEs) compared to 200 mg BID lonafarnib.

Example 4. Combination Treatment of HDV Patients with 100 mg BID Lonafarnib and 100 mg QD Ritonavir Three human subjects known to be infected with HDV, as documented by baseline HDV RNA viral titers ranging from 5.14 log HDV RNA copies/mL to 6.83 log HDV RNA copies/mL and ALT values of 84-195 U/L, were treated with lonafarnib at doses of 100 mg BID in combination with ritonavir at doses of 100 mg QD for a period of 8 weeks, substantially as otherwise described in Example 1.

At the end week 4, all three patients' HDV RNA viral titers had decreased from baseline, ranging from −1.71 log HDV RNA copies/mL to at least −2.76 log HDV RNA copies/mL drop in HDV-RNA, with an average drop across the three patients of −2.2 log HDV RNA copies/mL. At the end of week 8, all three patients' HDV RNA viral titers continued to decrease, with patient 2's viral titers being undetectable. See FIG. 5. The average viral load decline for the three patients at week 8 was −3.2 log HDV-RNA.

In addition, all three subjects' ALT values decreased from baseline, ranging from 35-50 U/L. Upper limit of normal for ALT values is estimated to be 40 U/L. See Table 9, which also shows the change in HDV RNA viral load for each patient.

TABLE 9

Combination therapy of 100 mg lonafarnib BID and 100 mg ritonavir QD

| | | Log HDV RNA copies/mL | | | | | | | ALT (U/L)* |
|---|---|---|---|---|---|---|---|---|---|
| Patient | Baseline | Wk 1 | Wk 2 | Wk 4 | Wk 5 | Wk 6 | Wk 8 | Change | Baseline to Wk 4 to Wk 8 |
| 1 | 6.34 | 4.96 | 4.40 | 4.63 | 4.48 | 4.18 | 3.97 | −2.37 | 83→50→43 |
| 2 | 5.14 | 4.21 | 3.30 | 2.38 | 1.86 | 2.08 | ND** | >−5 | 206→58→32 |
| 3 | 6.83 | 5.82 | 5.38 | 4.68 | 4.62 | 4.23 | 3.99 | −2.84 | 72→35→43 |

*Upper limit of normal = 40 U/L
**Below detection limit.

These results demonstrate superior efficacy compared to 200 mg BID and 300 mg BID lonafarnib monotherapy and over the combination treatment of 100 mg BID lonafarnib and Pegasys® (peg interferon alfa-2a) 180 μg per week. In addition, there were fewer grade 2 AEs observed as compared to 200 mg BID lonafarnib. See Table 10.

TABLE 10

| | N = 3 LNF 200 mg BID | | | | N = 3 LNF 300 mg BID | | | | N = 3 LNF 100 mg BID RTN 100 mg QD | | | | N = 3 LNF 100 mg BID PEG IFN 180 mcg QW | | | |
|---|---|---|---|---|---|---|---|---|---|---|---|---|---|---|---|---|
| Grade | 1 | 2 | 3 | 4 | 1 | 2 | 3 | 4 | 1 | 2 | 3 | 4 | 1 | 2 | 3 | 4 |
| Nausea | ✓ | | | | ✓ | | | | ✓ | | | | | ✓ | | |
| Diarrhea | ✓ | | | | ✓ | | | | | ✓ | | | ✓ | | | |
| Fatigue | ✓ | | | | ✓ | | | | | ✓ | | | | ✓ | | |
| Wt Loss | ✓ | | | | ✓ | | | | ✓ | | | | ✓ | | | |
| Anorexia | ✓ | | | | ✓ | | | | | ✓ | | | ✓ | | | |

Table 11 below shows the mean serum concentrations obtained with lonafarnib monotherapy (200 mg BID or 300 mg BID), lonafarnib-ritonavir co-therapy (100 mg BID lonafarnib in combination with 100 mg QD ritonavir), and lonafarnib-interferon co-therapy (100 mg BID lonafarnib in combination with 180 mcg QW pegylated interferon) at specific timepoints.

TABLE 11

| | Mean Serum Concentrations (ng/mL) | | | |
|---|---|---|---|---|
| | N = 3 LNF 200 mg BID | N = 3 LNF 300 mg BID | N = 3 LNF 100 mg BID RTN 100 mg QD | N = 3 LNF 100 mg BID Peg IFN 180 mcg QW |
| Day 7 | 2555 | 2994 | 2745 | 587 |
| Day 14 | 2959 | 1548 | 2720 | 896 |
| Day 21 | | | | |
| Day 28 | 2771 | 1984 | 2741 | 572 |
| Day 35 | | | 2860 | 1325 |
| Day 42 | | | 3633 | |
| Day 56 | 1656 | 2032 | 3767 | 643 |
| Day 84 | 443 | 977 | | |

Example 5. Treatment of HDV Patients with Lonafarnib and Ritonavir

The example describes the anti-HDV effect of the combination therapy of lonafarnib and ritonavir. Eight patients with chronic HDV infection were treated with four different dose combinations of lonafarnib and ritonavir (orally administered) for 84 days under the regimens summarized in Table 12.

Results

The changes in patients' HDV RNA levels from baseline as a result of lonafarnib and ritonavir combination therapy are summarized in Table 12 below.

TABLE 12

| Lonafarnib-Ritonavir Co-therapy | | | | | | | | |
|---|---|---|---|---|---|---|---|---|
| | Patient 1 | Patient 2 | Patient 3 | Patient 4 | Patient 5 | Patient 6 | Patient 7 | Patient 8 |
| Group | Group 1 | | Group 2 | | Group 3 | | Group 4 | |
| Dose lonafarnib | 100 mg BID | | 100 mg BID | | 100 mg QD | | 150 mg QD | |
| Dose ritonavir | 100 mg QD | | 50 mg BID | | 100 mg QD | | 100 mg QD | |
| Change log VL Baseline to Nadir | −2.32 | −3.37 | −2.37 | −1.99 | −2.05 | −2.12 | −1.45 | −1.39 |

TABLE 12-continued

Lonafarnib-Ritonavir Co-therapy

| | Patient 1 | Patient 2 | Patient 3 | Patient 4 | Patient 5 | Patient 6 | Patient 7 | Patient 8 |
|---|---|---|---|---|---|---|---|---|
| Change log VL Baseline to Day 28 | −2.32 | −2.45 | −2.37 | −1.94 | na | −2.01 | −1.39 | −1.39 |
| Change log VL Baseline to Day 56 | −1.56 | −2.23 | −1.79 | −1.20 | −1.58 | −1.61 | −1.00 | −0.70 |
| Change log VL Baseline to Day 84* | −1.47 | −0.61 | 1.09 | −0.62 | −2.05 | −2.00 | −0.71 | 0.21 |
| LNF Serum Concentration at Week 4 (ng/mL) | 3101 | 4827 | 3474 | 4580 | No data | 1411 | 1198 | 2042 |
| LNF Serum Concentration at Week 8 (ng/mL) | 1678 | 1484 | 3070 | 2969 | 1502 | 1662 | 1475 | 3139 |
| LNF Serum Concentration at Week 12 (ng/mL) | 1243 | 0 | 2377 | 423 | 1337 | 1807 | 1727 | 0 |

*See TABLE 12 for discussion of dose reductions in weeks 7-12

Figure 6A:
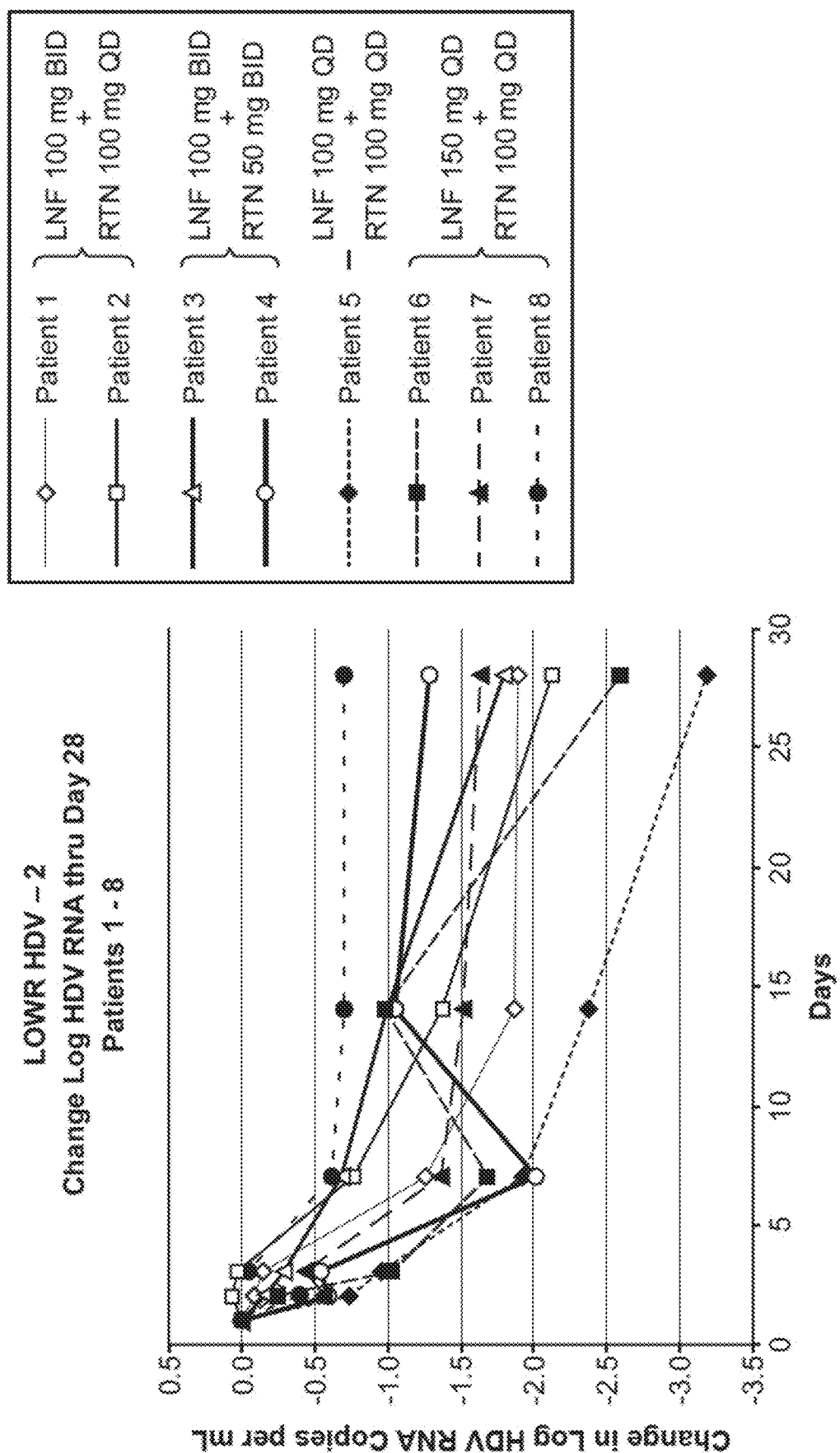
FIG. 6A-6C. Changes in HDV RNA viral titers.
Figure 6B:
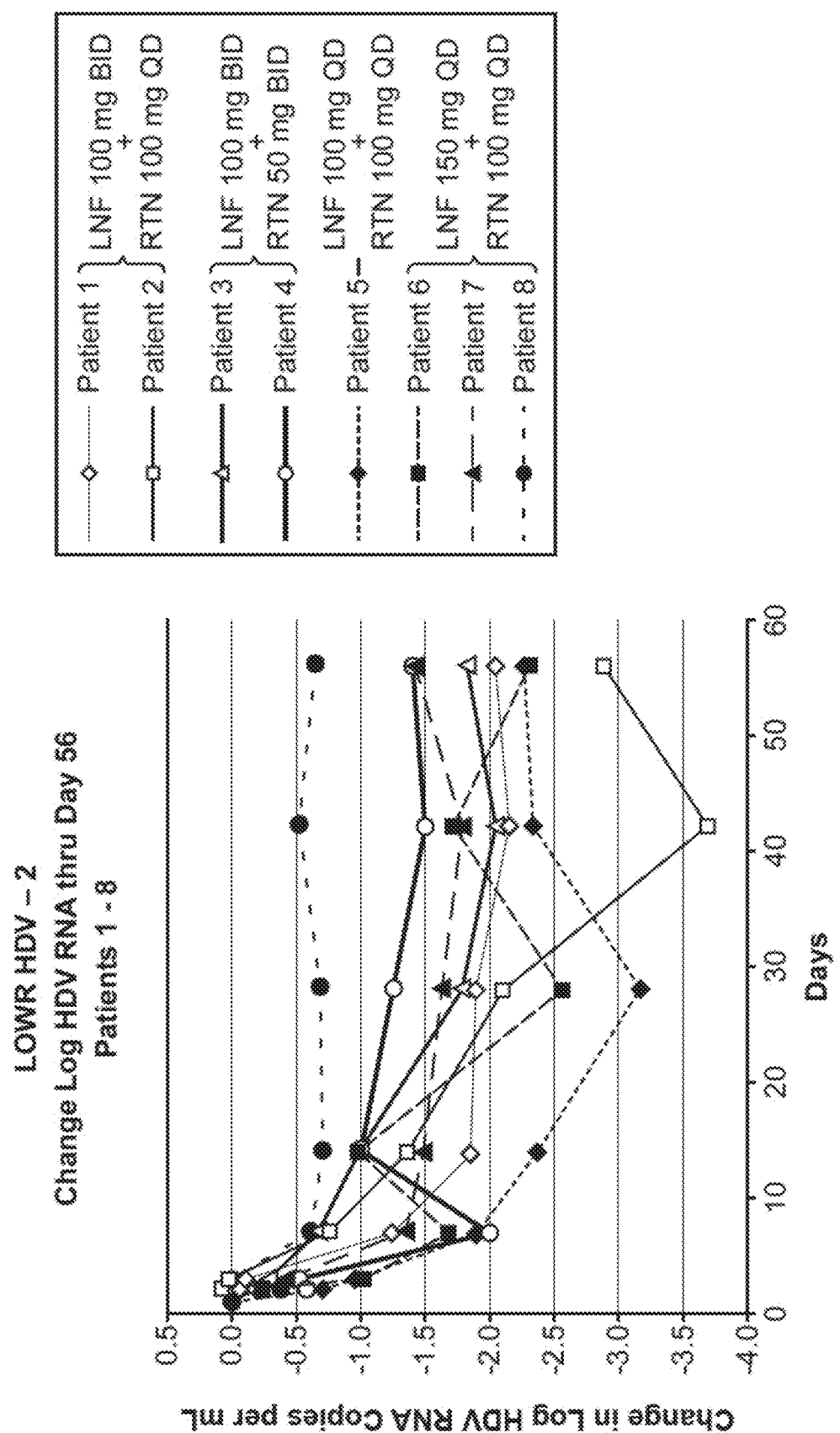
Figure 6C:
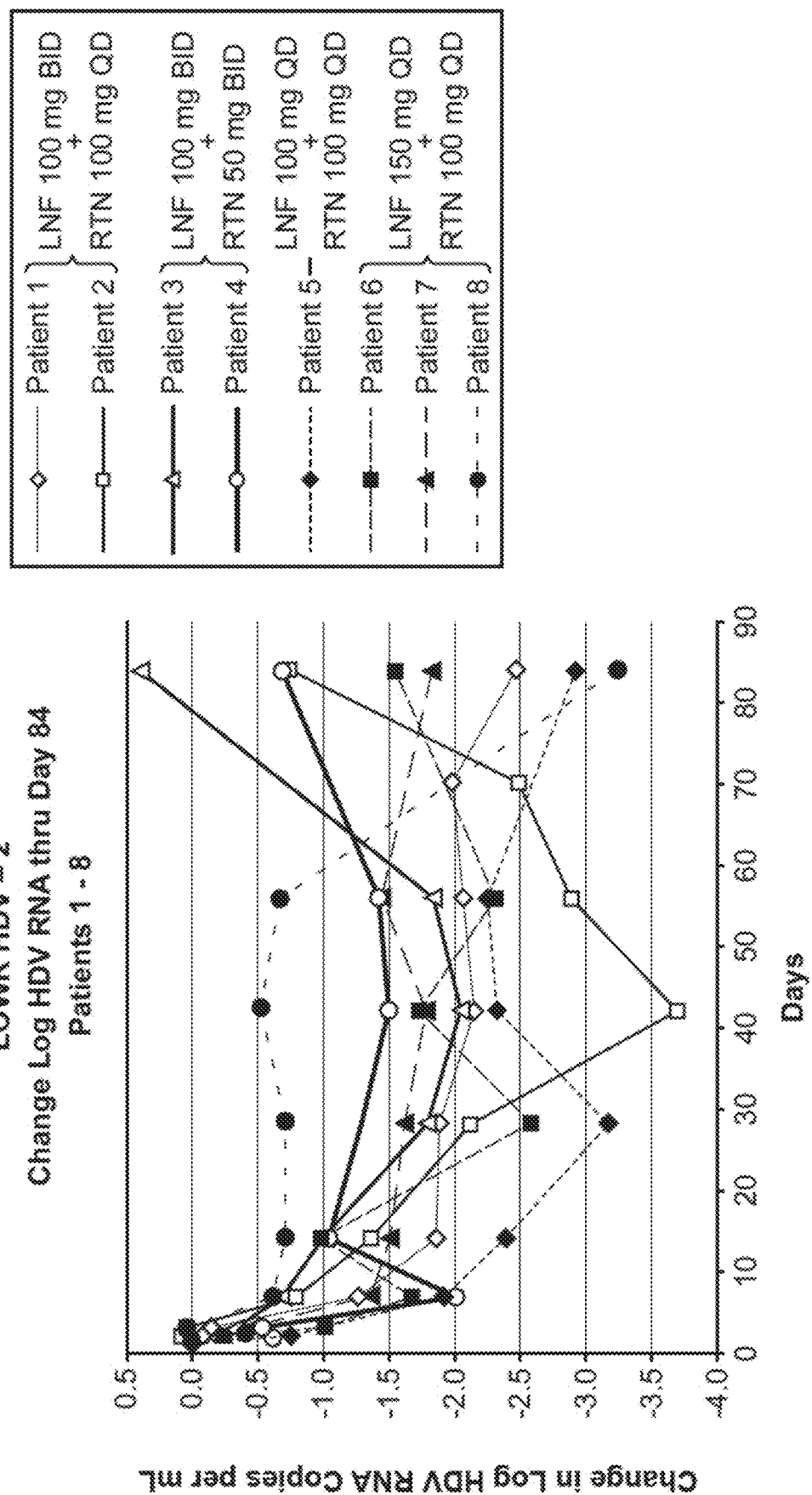

Time courses showing changes in HDV RNA levels in patients 1-8 through Day 28, Day 56 and Day 84 are shown in FIGS. 6A, 6B, and 6C, respectively (change relative to a normalized baseline). The mean change in log viral load was −1.89 after Day 28, −1.86 after Day 56 and −1.62 after Day 84. Nadirs were reached between week 4 to 6, after which viral load (VL) plateaued or in some cases, elevated slightly. Group 4 may have reached a saturable absorption point, supporting potentially even greater efficacy of a lower lonafarnib dose.

Figure 10:
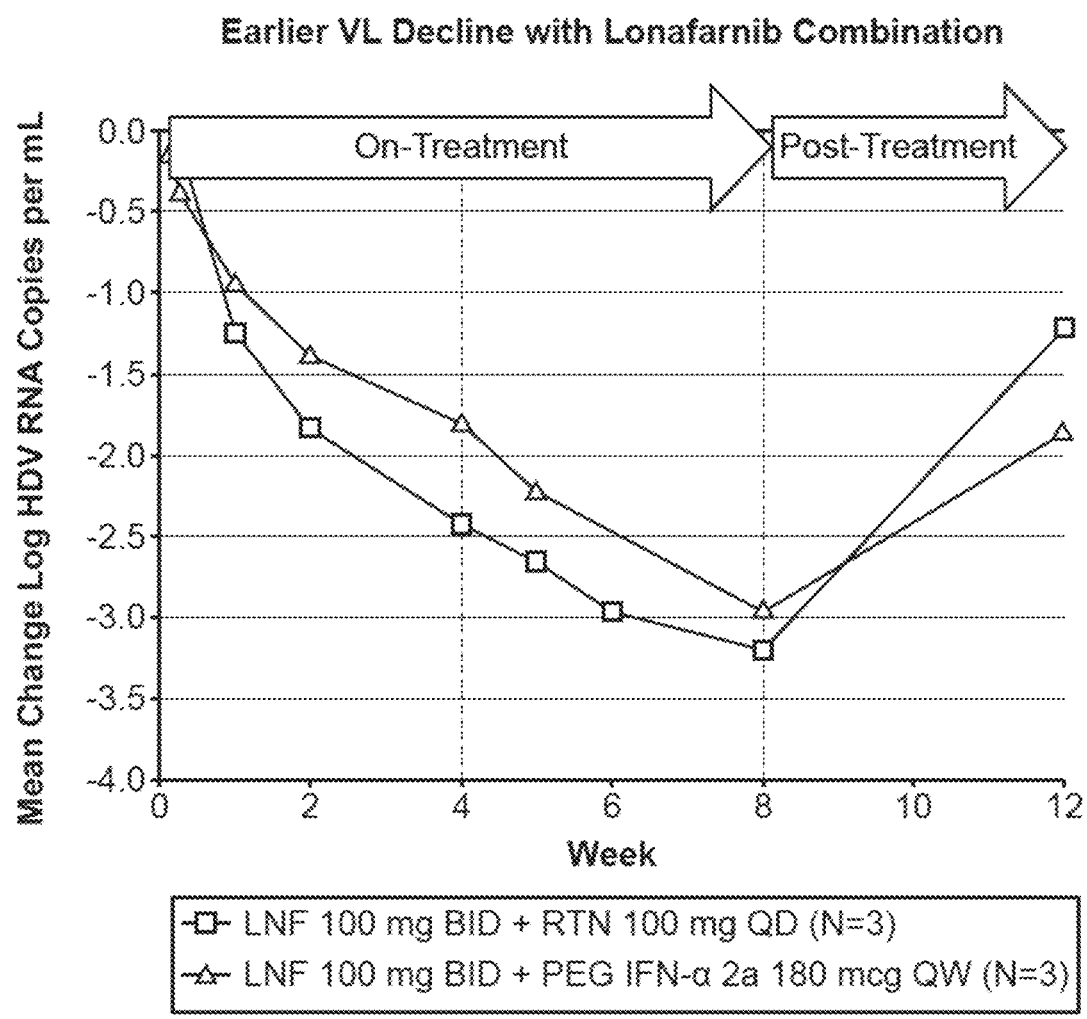
FIG. 10. Changes in HDV RNA viral titers in patients treated with lonafarnib and a pegylated interferon or lonafarnib and ritonavir.
Figure 11:
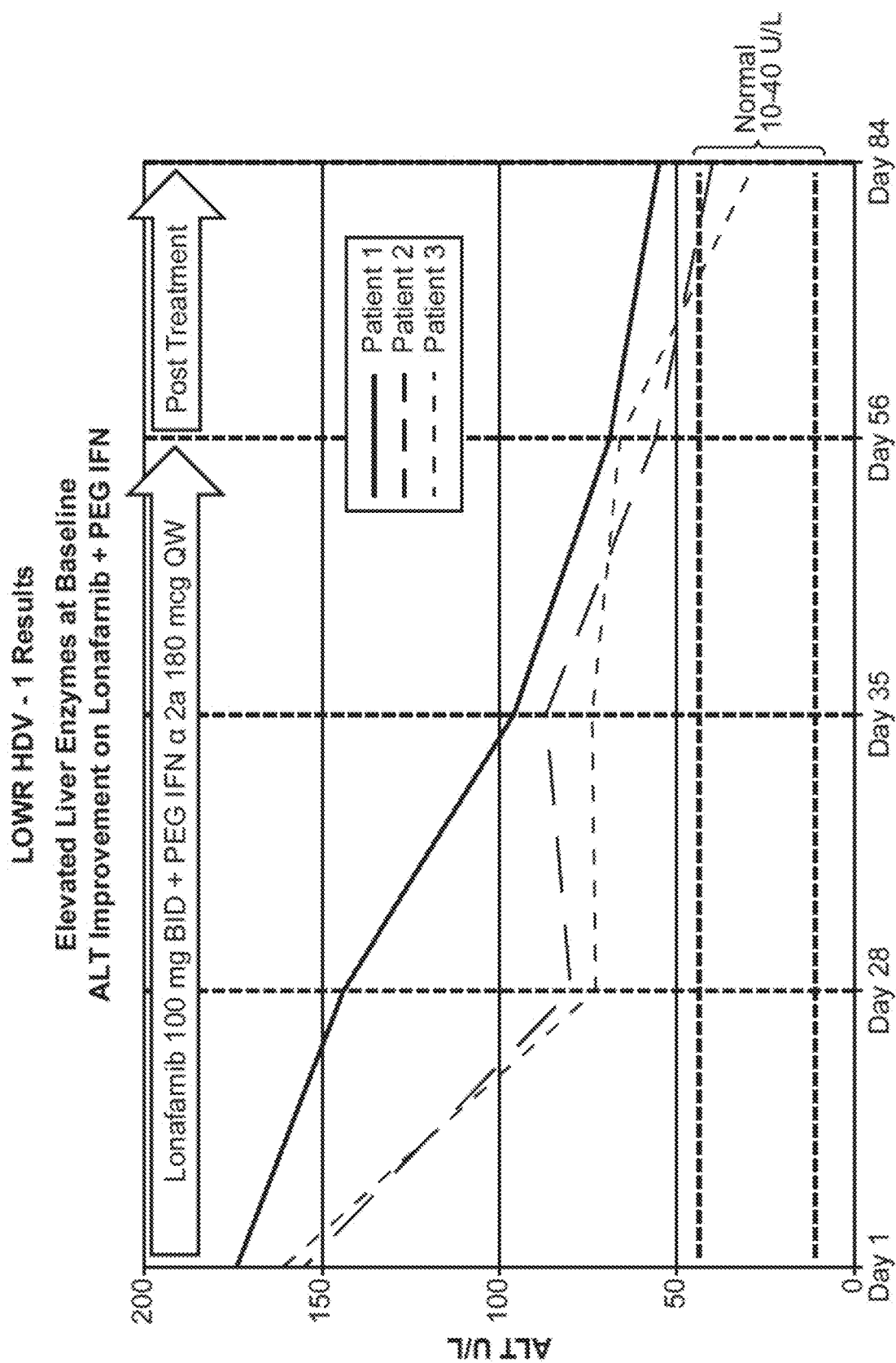
FIG. 11. Changes in ALT values in patients treated with lonafarnib and a pegylated interferon.

Groups 1 and 2 maintained the highest $C_{min}$. These two groups received either BID lonafarnib (Group 1) or BID ritonavir (Group 2). These results support the conclusion that higher or more frequent ritonavir doses are beneficial, e.g., BID administration. FIG. 10 illustrates that QD dosing of ritonavir (as shown in the graph) provides lonafarnib (LNF) serum concentrations that are in the 2500-3500 ng/mL range. Increasing ritonavir dosing to BID in patients may achieve higher lonafarnib serum concentrations of >5000 ng/mL.

Figure 8:
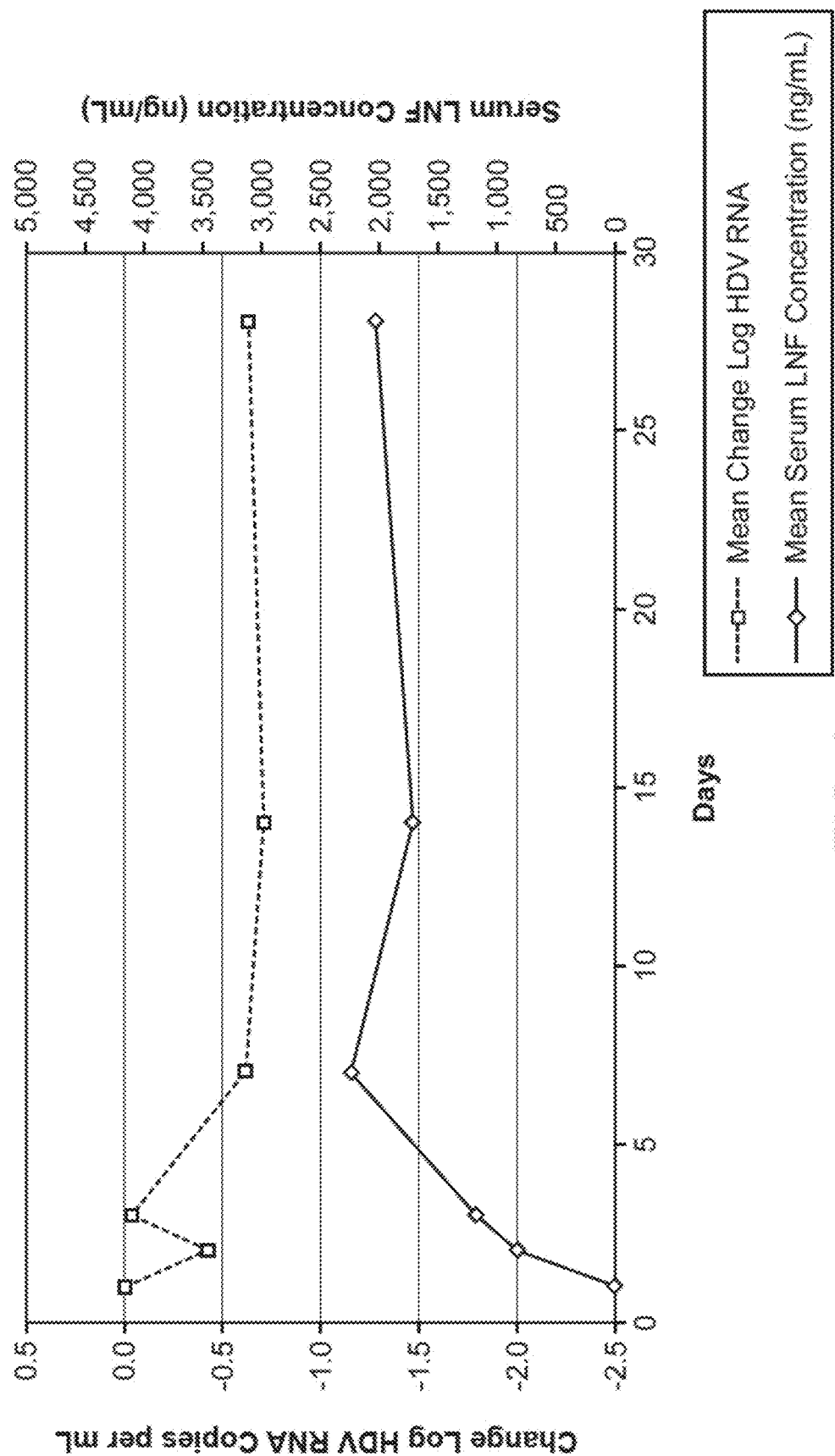
FIG. 8. Reduced correlation between lower lonafarnib serum levels and HDV viral load in a patient administered 150 mg lonafarnib QD and 100 mg ritonavir QD.
Figure 9:
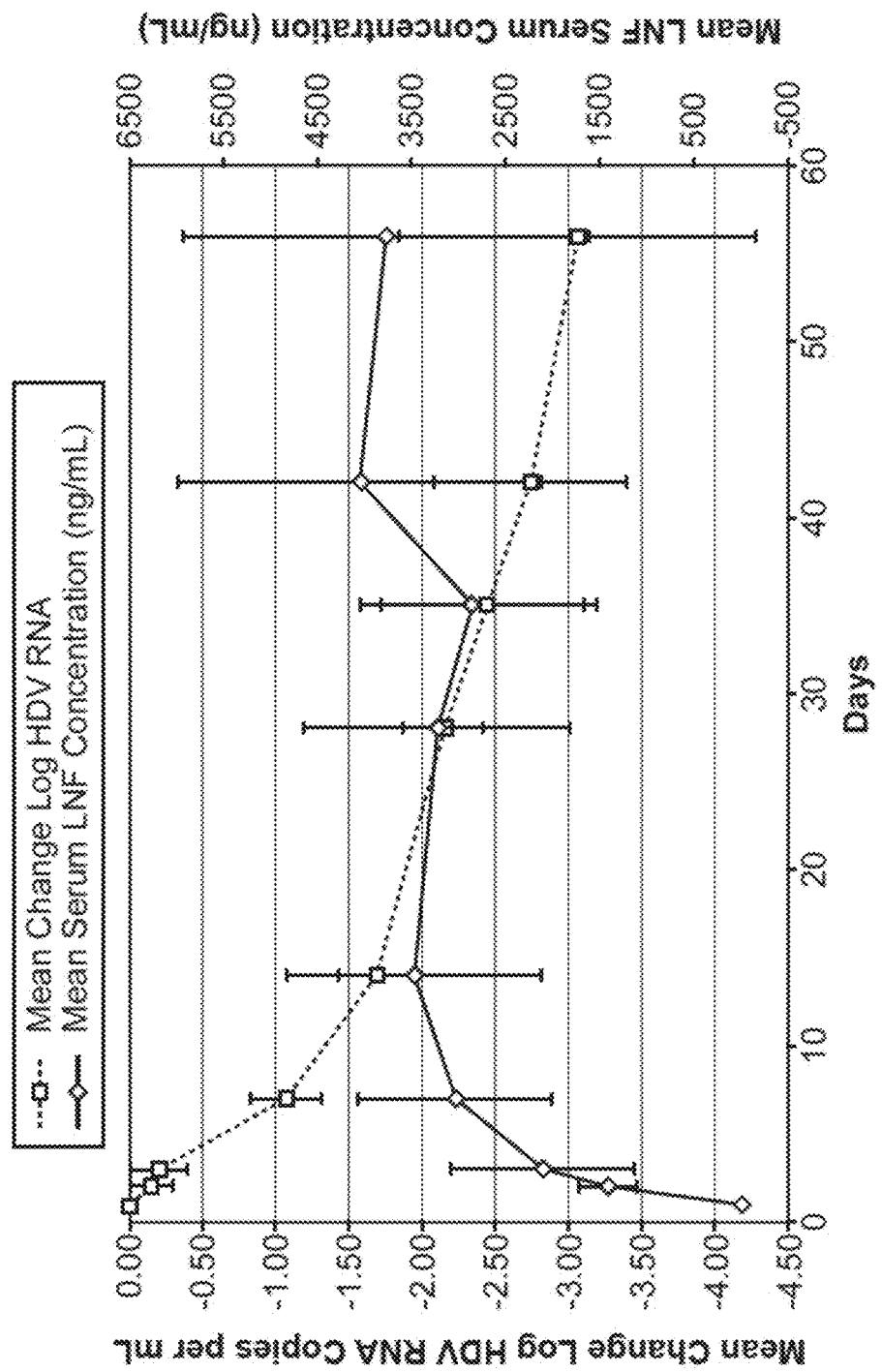
FIG. 9. Relationship between lonafarnib serum concentration and change in viral load in patients administered 100 mg lonafarnib BID and 100 mg ritonavir QD.

The correlation of increasing serum levels of lonafarnib with decreasing levels of HDV RNA in hepatitis delta infected patients treated with lonafarnib-ritonavir co-therapy is exemplified in patient 2 (FIG. 7) and patient 8 (FIG. 8). Patients with serum lonafarnib levels below 2000 ng/mL, such as patient 8 for example, are likely to have lower viral load declines (<1.5 log HDV-RNA) compared to patients with lonafarnib levels approaching or greater than 5,000 ng/mL (>2 log HDV-RNA).

Adverse Effects

Table 13 summarizes patients' adverse events during the first 6 weeks of therapy, and shows that 75% of patients in the study (six of eight patients) required at least one dose reduction in weeks 7-10. Dose reductions often resulted in a rise or plateau in HDV RNA levels.

TABLE 13

Lonafarnib Dose Reductions in Patients Experiencing Side Effects

| Patient | Lonafarnib Dose Reduction | Adverse events of LOWR2 patients during the course of the six week treatment |
|---|---|---|
| 1 | Dose reduction at "week 7" from 100 mg BID to 100 mg QD | Diarrhea and severe fatigue |
| 2 | Dose reduction at "week 7" from 100 mg BID to 50 mg (am) + 100 mg (pm) | Diarrhea. Fatigue and anorexia unbearable |
| 3 | Dose reduction at "week 8" from 100 mg BID to 150 QD | Diarrhea 2-3 times in a week (5-6 times per day), anorexia, fatigue |
| 4 | Dose reduction at "week 8" from 100 mg BID to 150 mg QD Further dose reduction at "week 10" from 150 mg QD to 50 mg QD | Severe anorexia, dry mouth, diarrhea 2-3 days per week |
| 5 | Dose reduction at "week 7" from 100 mg QD to 50 mg QD | Diarrhea 2 days per week, 3-4 bowel movements per day, anorexia and vomiting, fatigue |
| 6 | No dose reductions | nausea (moderate), diarrhea (rarely |
| 7 | No dose reductions | Diarrhea continued (7-8 times per day), anorexia (moderate) |
| 8 | Dose reduction a "week 10" from 150 mg QD to 100 mg QD | Diarrhea 20 times per day, mild anorexia and nausea, severe fatigue |

Lonafarnib dose was reduced in 6 of 8 patients (patients 1, 2, 3, 4, 5, 8) due to side effects. Dose reductions correlated with viral load plateau or increase. Lomotil and ondansetron were used by three of the eight patients (beginning at week 4). Of these three patients, two did not require lonafarnib dose reduction.

Example 6. Treatment of HDV Patients with Low Doses of Lonafarnib-Ritonavir Cotherapy and Lonafarnib-Ritonavir-Pegylated Interferon Alpha Triple Therapy FIG. 12 shows HDV levels in three patients with chronic HDV infection (Patients 13, 14 and 15) treated with lonafarnib (75 mg BID) in combination with ritonavir (100 mg BID) for 12 weeks. At week 12, ritonavir administration was discontinued and PEG-IFN-α was administered (180 mcg QW). At week 16, ritonavir (100 mg BID) administration was reinitiated.

Results

Time courses showing changes in HDV RNA levels in patients 13, 14 and 15 are shown in FIG. 12 (change relative to a normalized baseline). Between Weeks 12 and 16 (lonafarnib-interferon co-therapy) viral load was about constant (patients 13 and 15) or increased (patient 14). From Week 16 to Week 20, the patients received triple therapy resulting in a significant decrease in viral load (patients 13 and 14).

Example 7. Triple Therapy with Low (50 mg BID) Dose Lonafarnib

Three patients with chronic HDV infection (patients 25, 26 and 27) were treated with lonafarnib (50 mg BID), ritonavir (100 mg BID), and pegylated interferon alpha (180 mcg QW) for 4 weeks. See FIG. 13. A significant reduction in viral load was seen at 2 weeks. At 4 weeks all patients had significantly reduced viral load relative to baseline. These results support the conclusion that lower doses of lonafarnib can be administered in combination with a boosting agent (e.g., ritonavir) and an interferon (e.g., interferon alpha or interferon lambda) that enable patients to achieve significant therapeutic benefit.

Example 8. Triple Therapy with Low (50 mg BID) and Very Low (50 mg QD) Dose Lonafarnib FIG. 14 shows the effect on viral load of triple therapy in 3 patients with chronic HDV infection. Patients 2 and 3 received 50 mg BID lonafarnib, 100 mg BID ritonavir, and 180 mcg QW pegylated interferon alpha for 8 weeks. Patient 1 received 50 mg BID lonafarnib, 100 mg BID ritonavir, and 180 mcg QW pegylated interferon alpha for almost 3 weeks, at which time the dose of lonafarnib was reduced to 50 mg QD (except for 1 day during week 8 on which 50 mg BID was administered). The patients received proton pump inhibitors (esomeprazole or rabeprazole on a QD basis) and an anti-diarrheal (lomotil or loperamide BID or TID).

As shown in FIG. 14, the mean decrease in log HDV viral load is greater than 2 (patient 3) or greater than 3 (patient 2) after 8 weeks at the 50 mg BID dose, and was greater than 3 (patient 1) at the 50 mg QD dose. The therapy was well tolerated, with diarrhea the most prominent side effect, indicating that triple therapy is well suited for long term therapy (6 months or greater).

Example 9: Exemplary Treatment Regimens

This prophetic example describes treating HDV infection by administration of varying doses of lonafarnib and ritonavir as disclosed in Table 14 below. A patient infected with HDV self-administers the following regimen daily for 90-180 days. During the course of the treatment the patient's lonafarnib serum levels and HDV viral load are determined periodically. After 90 days of treatment the patient's viral load is reduced over baseline.

Example 10. A Phase 2 Study to Evaluate the Safety, Tolerability, and Pharmacodynamics of Pegylated Interferon Lambda-1a (PEG-IFN-λ) Monotherapy in Patients with Chronic Hepatitis D Virus Infection This prophetic example describes a Phase 2 clinical study protocol for evaluating the safety, tolerability, and pharmacodynamics of pegylated interferon lambda monotherapy in patients with chronic HDV infection. The efficacy demonstrated by interferon lambda monotherapy in this protocol is indicative that interferon lambda therapy in combination with lonafarnib, and optionally in combination with an additional boosting agent such as ritonavir, will be efficacious for the treatment of HDV infection.

Two dose levels of PEG-IFN-λ (120 µg per week or 180 µg per week are administered by subcutaneous injection over a 48 week treatment period and the safety and tolerability of treatment is evaluated based on HDV levels, ALT levels, and Hepatitis B surface antigen (HBsAg) levels.

At least one patient from the cohort of patients who receive at least 80% of the total study drug dose throughout the entire 48-week treatment period and for whom HDV viral load data are available for the Day 1 (baseline) and end-of-treatment (Week 48) study visits shows improvement in one or more endpoints as described in the protocol. In some embodiments, a patient receiving treatment with interferon lambda monotherapy exhibits a reduction in HDV viral load at end-of-treatment as compared to baseline. In some embodiments, a patient receiving treatment with interferon lambda monotherapy exhibits a reduction in HBV viral load at end-of-treatment as compared to baseline. In some embodiments, a patient receiving treatment with interferon lambda monotherapy exhibits a reduction in the level of HBsAg at end-of-treatment as compared to baseline. In some embodiments, a patient receiving treatment with interferon lambda monotherapy exhibits improved clearance of HBsAg antigen.

Example 11: Triple Therapy

This prophetic example describes treating HDV infection by administration of interferon lambda in combination with lonafarnib and ritonavir. Administration of pegylated interferon lambda in combination with lonafarnib and ritonavir provides efficacious therapy at lower doses and/or reduced dosing frequency.

TABLE 14

| Illustrative Embodiment 9 | Illustrative Embodiment 10 | Illustrative Embodiment 11 |
|---|---|---|
| lonafarnib 50 mg QD ritonavir 100 mg QD | lonafarnib 50 mg BID ritonavir 50 mg BID ondansetron 8 mg BID lomotil 5 mg BID famotidine 20 mg BID. | lonafarnib 75 mg QD ritonavir 100 mg QD ondansetron 8 mg BID lomotil 5 mg BID famotidine 20 mg BID. |
| Illustrative Embodiment 12 | Illustrative Embodiment 13 | Illustrative Embodiment 14 |
| lonafarnib 75 mg BID ritonavir 50 mg BID ondansetron 8 mg BID lomotil 5 mg BID* famotidine 20 mg BID omeprazole 20 mg BID | lonafarnib 25 mg BID ritonavir 100 mg BID ondansetron 8 mg BID lomotil 5 mg BID famotidine 20 mg BID. | lonafarnib 50 mg BID ritonavir 100 mg BID |

*titrate to dose

A patient infected with HDV is administered pegylated interferon lambda at 120 mcg QW or 180 mcg QW, in combination with one of the following lonafarnib+ritonavir dosage combinations:

lonafarnib 50 mg BID+ritonavir 100 mg BID
lonafarnib 25 mg BID+ritonavir 100 mg BID
lonafarnib 75 mg BID+ritonavir 100 mg BID
lonafarnib 50 mg QD+ritonavir 100 mg QD
lonafarnib 75 mg QD+ritonavir 100 mg QD
lonafarnib 100 mg QD+ritonavir 100 mg QD
lonafarnib 50 mg QD+ritonavir 100 mg BID
lonafarnib 75 mg QD+ritonavir 100 mg BID
lonafarnib 100 mg QD+ritonavir 100 mg BID During the course of the treatment the patient's HDV viral load is determined periodically. After 90 days of treatment the patient's viral load is reduced over baseline.

Example 12. Combination Regimens of Lonafarnib-Ritonavir Co-Therapy

This example demonstrates the efficacy and tolerability of various combination regimens of lonafarnib and ritonavir, with or without pegylated interferon-α, in patients known to be infected with HDV. 38 patients were dosed as shown below in Table 15. The duration of treatment was 12-24 weeks. On day 1 and day 28 of treatment, a 72 hour pharmacokinetics (PK) and pharmacodynamics (PD) evaluation was performed. Additionally, during the course of treatment biochemical parameters and HDV RNA level (as measured by quantitative real-time PCR) were measured on days 1, 2, 3, 7, 14, and 28, and then every 4 weeks thereafter.

TABLE 15

Dosing regimen for lonafarnib-ritonavir cotherapy ± interferon

| Amount of lonafarnib | Amount of ritonavir | Amount of Pegylated interferon-α | Number of patients |
|---|---|---|---|
| 100 mg BID | 100 mg QD | — | 3 |
| 100 mg BID | 50 mg BID | — | 2 |
| 100 mg QD | 100 mg QD | — | 5 |
| 150 mg QD | 100 mg QD | — | 3 |
| 75 mg BID | 100 mg BID | — | 3 |
| 50 mg BID | 100 mg BID | — | 6 |
| 25 mg BID | 100 mg BID | — | 5 |
| 50 mg BID | 100 mg BID | 180 mcg QW | 3 |
| 25 mg BID | 100 mg BID | 180 mcg QW | 7 |

Figure 15B:
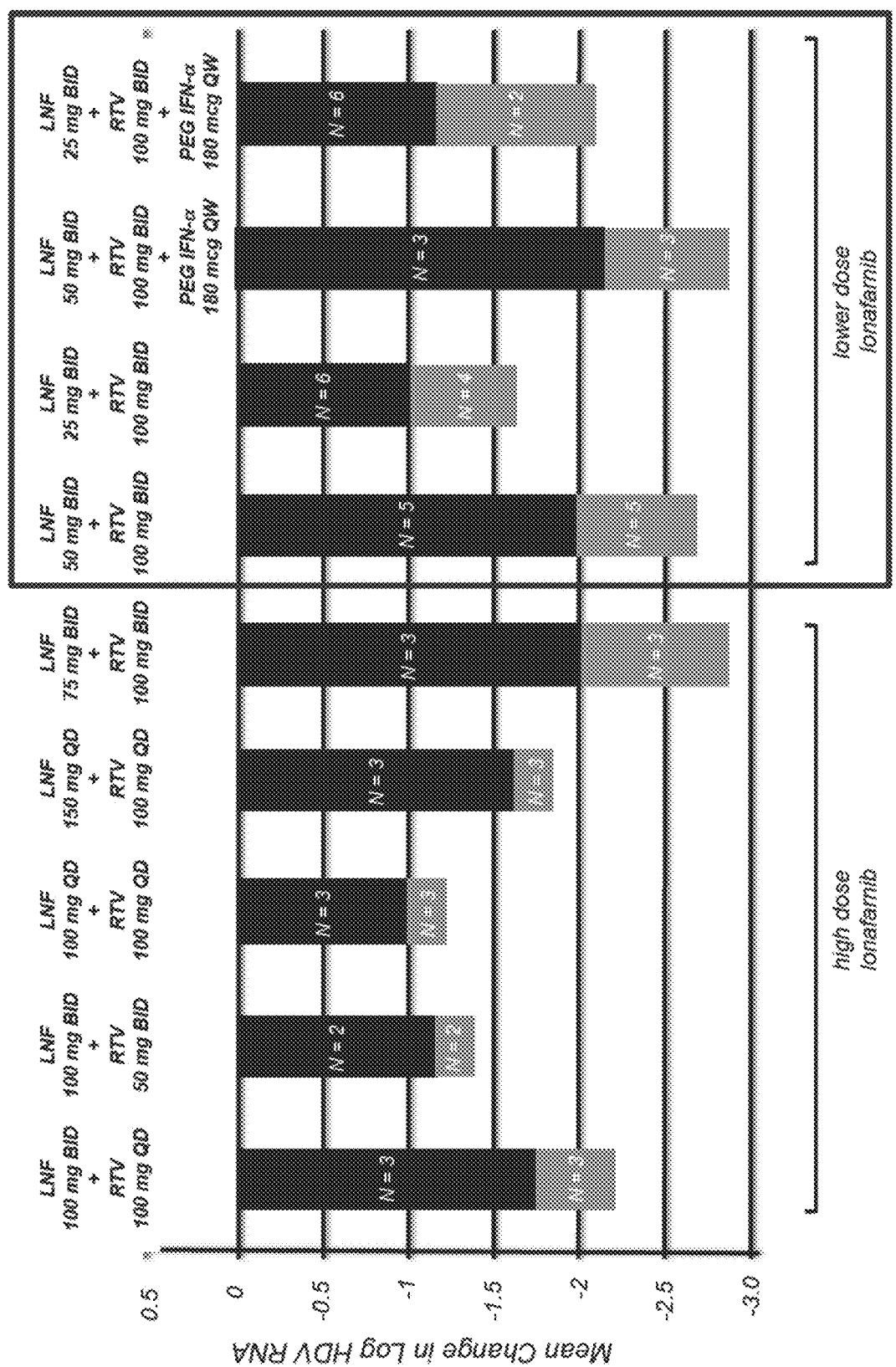

For all treatment groups, HDV RNA viral load was measured after 4 weeks and 8 weeks of treatment and compared to baseline HDV RNA virus load. As shown in FIG. 15A, when HDV RNA viral load was measured after 4 weeks, comparable viral load decline was observed for patients receiving 25 mg BID or 50 mg BID lonafarnib in combination with 100 mg BID ritonavir, with or without pegylated interferon-α, as compared to patients receiving higher doses of lonafarnib in the lonafarnib-ritonavir co-therapy. As shown in FIG. 15B, when HDV RNA viral load was measured after 8 weeks, comparable viral load was observed for patients receiving 25 mg BID or 50 BID lonafarnib in combination with 100 mg BID ritonavir, with or without pegylated interferon-α, as compared to patients receiving higher doses of lonafarnib in the lonafarnib-ritonavir co-therapy.

Figure 18:
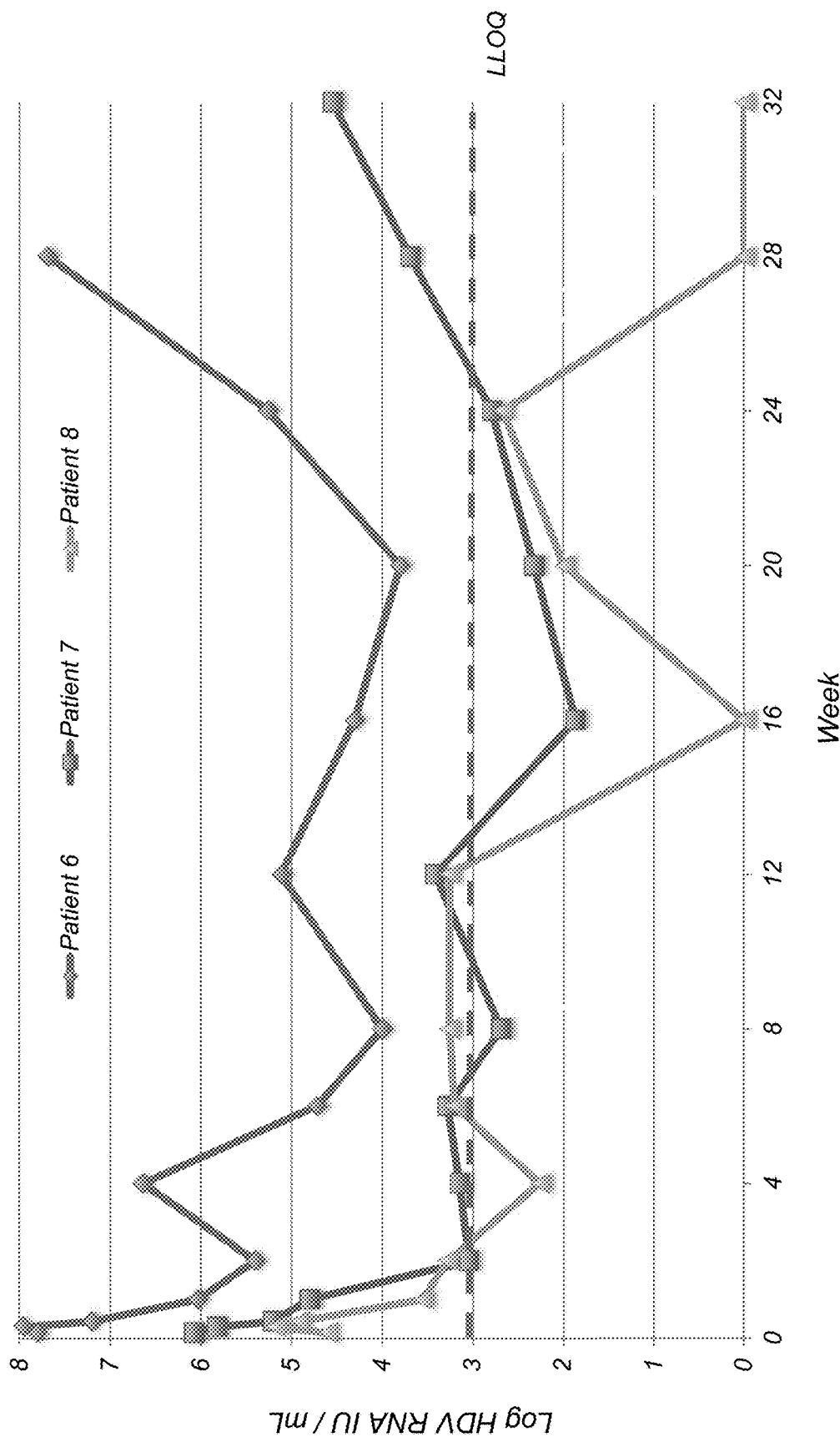
FIG. 18. Time course of HDV RNA levels (copies/mL) in patients treated with 50 mg BID lonafarnib, 100 mg BID ritonavir, and 180 mcg QW pegylated interferon-α as described in Example 12.

FIG. 16 shows that rapid declines in HDV viral levels were observed in patients receiving 25 mg BID or 50 mg BID lonafarnib in combination with 100 mg BID ritonavir, with or without pegylated interferon-α. For patients receiving 50 mg BID lonafarnib in combination with 100 mg BID ritonavir and patients receiving 50 mg BID lonafarnib in combination with 100 mg BID ritonavir and 180 mcg QW PEG IFN-α, the change in HDV RNA viral load after 8 weeks was comparable to the change in HDV RNA viral load after 48 weeks of treatment with 180 mcg QW PEG IFN-α in combination with tenofovir. Additionally, for a subset of patients receiving 50 mg BID lonafarnib in combination with 100 mg BID ritonavir, 50 mg BID lonafarnib in combination with 100 mg BID ritonavir and 180 mcg QW PEG IFN-α, or 25 mg BID lonafarnib in combination with 100 mg BID ritonavir and 180 mcg QW PEG IFN-α, HDV RNA viral negativity (clearance) was observed. See FIG. 17 and FIG. 18.

For the group of patients receiving 50 mg BID lonafarnib in combination with 100 mg BID ritonavir, patients 2, 3, 4, and 5 were responsive to therapy, as defined by greater than or equal to a 0.5 log HDV RNA copies/mL decline in quantitative serum HDV RNA levels from baseline to nadir during active treatment. See FIG. 17 (showing the time course of the log HDV IU/mL over 12 weeks of treatment).

For the group of patients receiving 50 mg BID lonafarnib in combination with 100 mg BID ritonavir and 180 mcg QW PEG IFN-α, patients 7 and 8 were responsive to therapy, as defined by greater than or equal to a 0.5 log HDV RNA copies/mL decline in quantitative serum HDV RNA levels from baseline to nadir during active treatment. See FIG. 18 (showing the time course of the log HDV IU/mL over 32 weeks of treatment).

Figure 19:
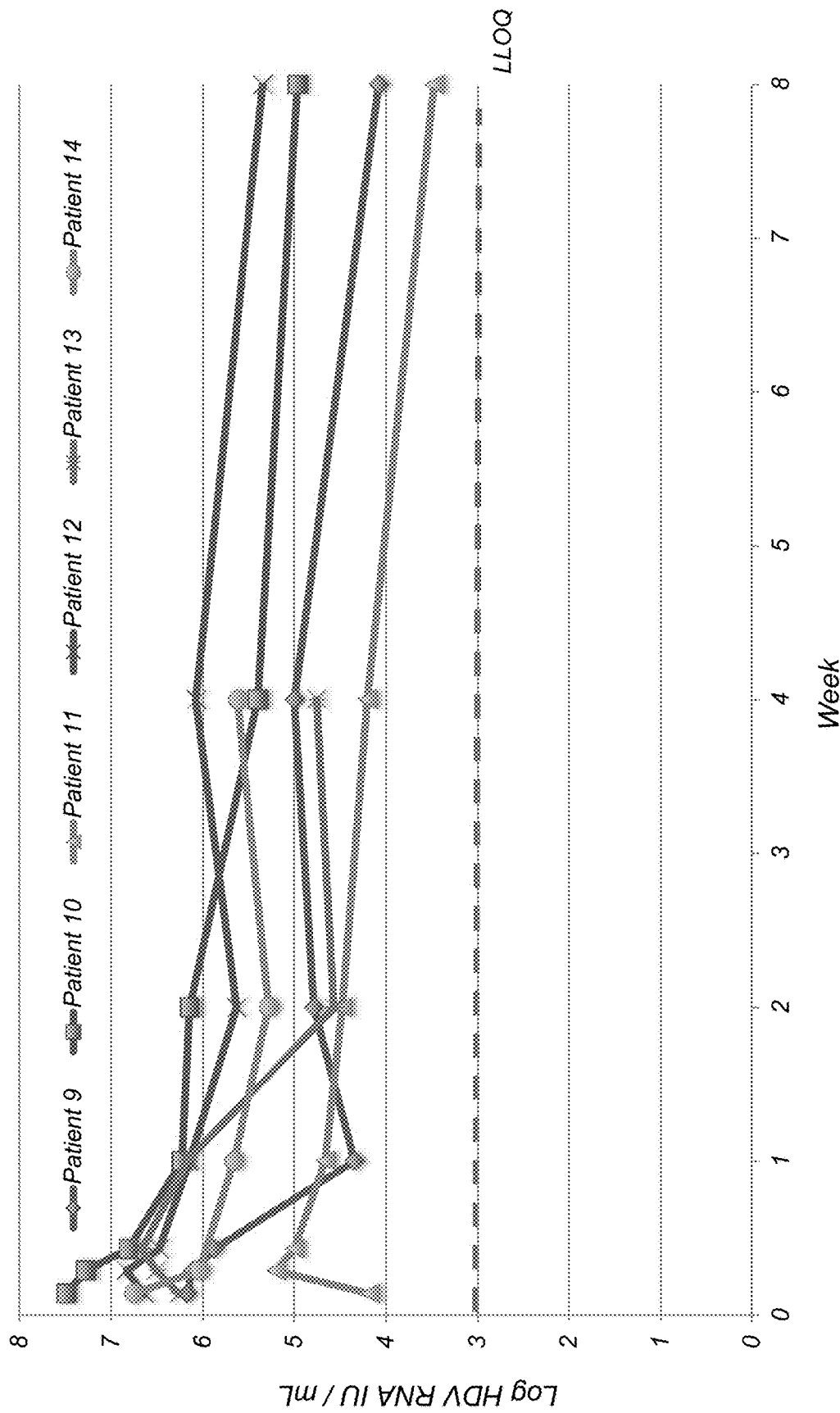
FIG. 19. Time course of HDV RNA levels (copies/mL) in patients treated with 25 mg BID lonafarnib and 100 mg BID ritonavir as described in Example 12.

For the group of patients receiving 25 mg BID lonafarnib in combination with 100 mg BID ritonavir, patients 9, 10, 11, 12, 13, and 14 were responsive to therapy, as defined by greater than or equal to a 0.5 log HDV RNA copies/mL decline in quantitative serum HDV RNA levels from baseline to nadir during active treatment. See FIG. 19 (showing the time course of the log HDV IU/mL over 8 weeks of treatment).

Figure 20:
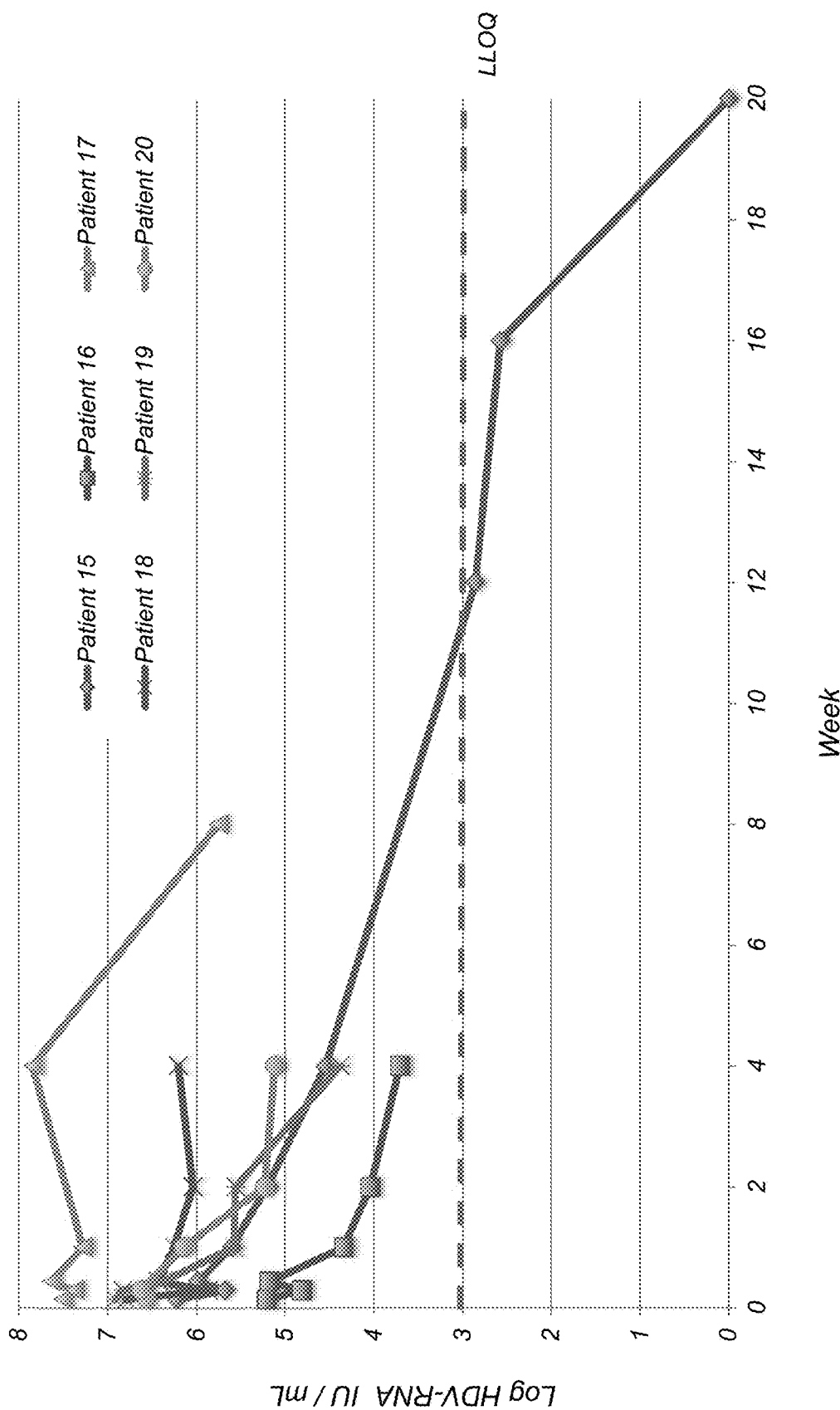
FIG. 20. Time course of HDV RNA levels (copies/mL) in patients treated with 25 mg BID lonafarnib, 100 mg BID ritonavir, and 180 mcg QW pegylated interferon-α as described in Example 12.

For the group of patients receiving 25 mg BID lonafarnib in combination with 100 mg BID ritonavir and 180 mcg QW PEG IFN-α, patients 15, 16, 17, 19, and 20 were responsive to therapy, as defined by greater than or equal to a 0.5 log HDV RNA copies/mL decline in quantitative serum HDV RNA levels from baseline to nadir during active treatment. See FIG. 20 (showing the time course of the log HDV IU/mL over 20 weeks of treatment).

Figure 21:
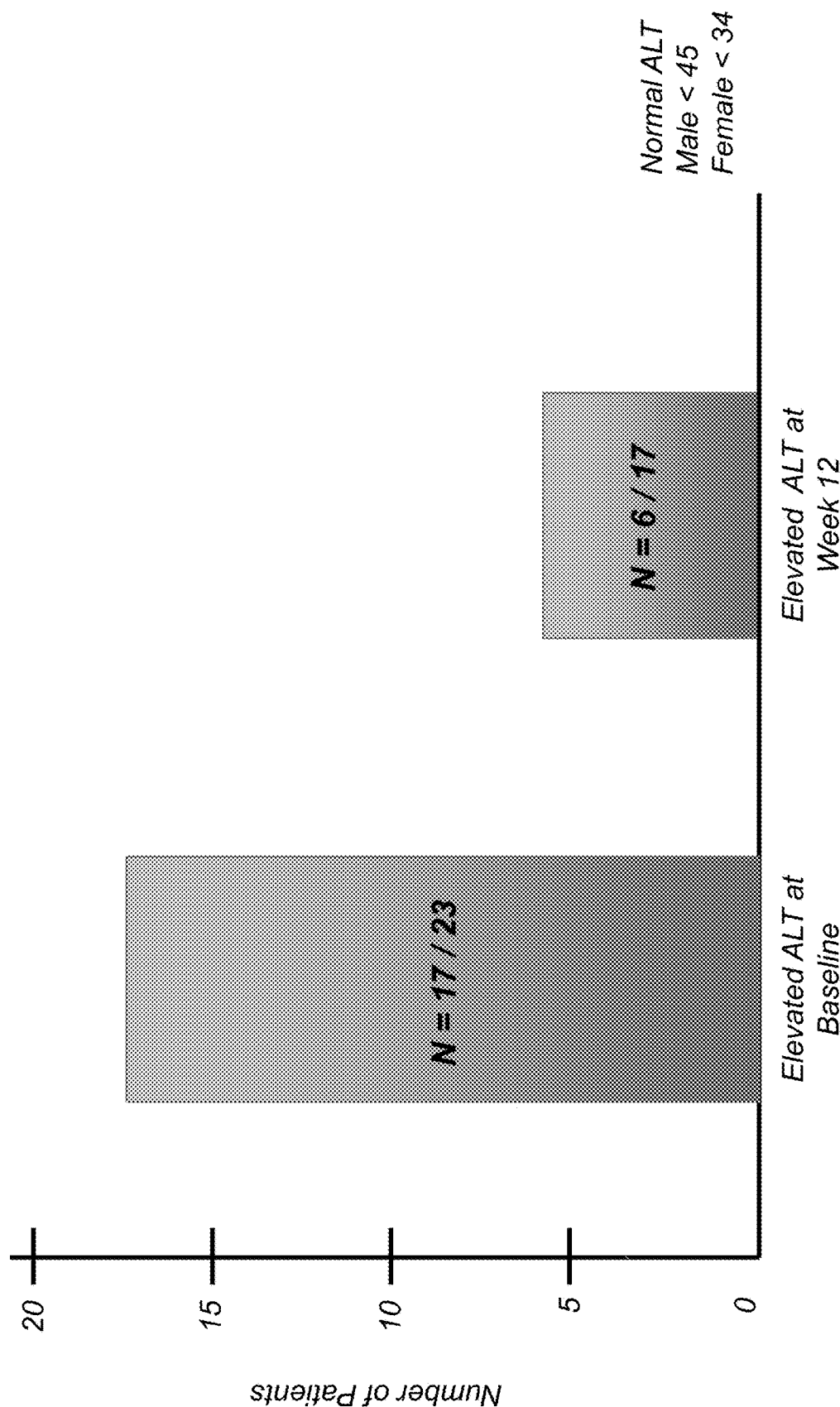
FIG. 21. Changes in ALT values at week 12 of treatment as described in Example 12.

In addition, normalization of ALT values was observed for 65% of patients at week 12. As shown in FIG. 21, 17 patients had elevated ALT values at baseline, but only 6 patients had elevated ALT values at week 12. The upper limit of normal for ALT values was 45 for males and 34 for females.

Dosing regimens with lower dosages are also better tolerated, as shown in Table 16 below. The numbers in the table indicate the number of patients experiencing an adverse event. Mostly grade 1 gastrointestinal AEs were observed with the lower doses.

TABLE 16

| Grade | N = 4*<br>LNF 100 mg<br>BID + RTV<br>100 mg QD | | N = 3*<br>LNF 100 mg<br>BID + RTV<br>50 mg BID | | N = 5**<br>LNF 100 mg<br>QD + RTV<br>100 mg QD | | N = 3<br>LNF 150 mg<br>QD + RTV<br>100 mg QD | | N = 3<br>LNF 75 mg<br>BID + RTV<br>100 mg BID | | N = 5<br>LNF 50 mg<br>BID + RTV<br>100 mg BID | | N = 3<br>LNF 50 mg BID +<br>RTV 100 mg BID +<br>PEG IFNα 180 mcg QW | |
|---|---|---|---|---|---|---|---|---|---|---|---|---|---|---|
| | 1-2 | 3-4 | 1-2 | 3-4 | 1-2 | 3-4 | 1-2 | 3-4 | 1-2 | 3-4 | 1-2 | 3-4 | 1-2 | 3-4 |
| Nausea | 1 | | | | 4 | | 2 | | 2 | | 2 | | 1 | |
| Diarrhea | 1 | 2 | 2 | | 3 | 1 | | 2 | 2 | 1 | 4 | | 3 | |
| Fatigue | 2 | 1 | 2 | | 2 | 2 | 2 | 1 | 2 | 1 | 4 | | 3 | |
| Anorexia | 2 | 1 | 2 | | 3 | | 2 | 1 | 3 | | 2 | | 2 | |
| Wt loss | | | | | | | | | | | | | 2 | |
| Vomiting | | | | | 3 | | 1 | | | | 1 | | | |

*1 discontinuation
**2 discontinuations

Example 13. Lonafarnib-Ritonavir Co-Therapy Duration Study

This example demonstrates the efficacy and tolerability of three doses of lonafarnib (50 mg, 75 mg, and 100 mg) administered once daily, each in combination with ritonavir 100 mg administered once daily for 12 or 24 weeks. 21 patients with chronic HDV infection were randomized into one of six treatment groups as summarized in Table 17 below:

TABLE 17

| Months 1-3 | Months 4-6 | Number of patients |
|---|---|---|
| Lonafarnib 100 mg QD +<br>ritonavir 100 mg QD | Lonafarnib 100 mg QD +<br>ritonavir 100 mg QD | 4 |
| Lonafarnib 75 mg QD +<br>ritonavir 100 mg QD | Lonafarnib 75 mg QD +<br>ritonavir 100 mg QD | 4 |
| Lonafarnib 50 mg QD +<br>ritonavir 100 mg QD | Lonafarnib 50 mg QD +<br>ritonavir 100 mg QD | 4 |
| Placebo | Lonafarnib 100 mg QD +<br>ritonavir 100 mg QD | 3 |
| Placebo | Lonafarnib 75 mg QD +<br>ritonavir 100 mg QD | 3 |
| Placebo | Lonafarnib 50 mg QD +<br>ritonavir 100 mg QD | 3 |

The lonafarnib/ritonavir co-therapy is expected to result in mean HDV-RNA declines of 2 log after 12 weeks of co-therapy. It is anticipated that doses of 50 mg QD lonafarnib in combination with 100 mg QD ritonavir, and 75 mg QD lonafarnib in combination with 100 mg QD ritonavir will be tolerable to enable greater than 24 weeks of dosing. It is anticipated that the addition of an interferon (e.g., pegylated interferon alpha or pegylated interferon lambda) for greater than 24 weeks may achieve HDV-RNA negativity in a subset of patients.

Example 14. Lonafarnib-Ritonavir Co-Therapy Dose Titration Study

This example demonstrates the efficacy, safety, and tolerability of lonafarnib and ritonavir co-therapy administered twice daily. 15 patients (11 male) were enrolled in a 24-week open-label study that included the option of dose escalation at the discretion of the investigator. The study was a Phase 2 study of 24 weeks of treatment with a dose-titration regimen of lonafarnib/ritonavir in patients chronically infected with HDV. Lonafarnib was administered starting at 50 mg BID and escalating to 75 mg BID and then 100 mg BID as tolerated, in combination with ritonavir administered at 100 mg BID. The initial dose of lonafarnib (50 mg BID) and ritonavir (100 mg BID) was maintained for at least 4 weeks; subsequent dose escalation occurred at an interval of no less than 2 weeks after patients had first received a particular dose.

At baseline (BL), the mean HDV RNA viral load for the patients was 6.53 $\log_{10}$ IU/mL (range 4.43-8.31 $\log_{10}$ IU/mL). The mean serum ALT level was 111 U/L (range 53-362 U/L). Liver stiffness (fibrosis) was also assessed by FibroScan®. Two patients were cirrhotic on biopsy. 11 patients were receiving a nucleoside or nucleotide analogue (NUC) at BL.

By Week 8 of treatment, 10 of the 15 patients (66%) were able to be dose-escalated to 100 mg BID lonafarnib in combination with ritonavir. All patients exhibited declines in HDV RNA viral load, with a mean decline from BL to Week 8 of 1.87 $\log_{10}$ IU/mL (range 0.88-3.13 $\log_{10}$ IU/mL). Three patients exhibited HBV DNA rebound associated with HDV RNA decline, and two of the patients were started on treatment with the anti-HBV medication tenofovir. AE were mostly grade 1-2 intermittent diarrhea; 3 patients had grade 3 AE (2 diarrhea; 1 asthenia), all transient and non-recurring; no patients had a grade 4 AE. This data from 8 weeks treatment demonstrates that dose-escalation of lonafarnib in combination with ritonavir was feasible, and led to early decline in HDV RNA in all patients. HDV RNA decline was associated with a rebound of HBV DNA in patients not receiving a NUC, suggesting a suppressive effect of HDV on HBV replication. These data support the use of longer durations of therapy.

Figure 22:
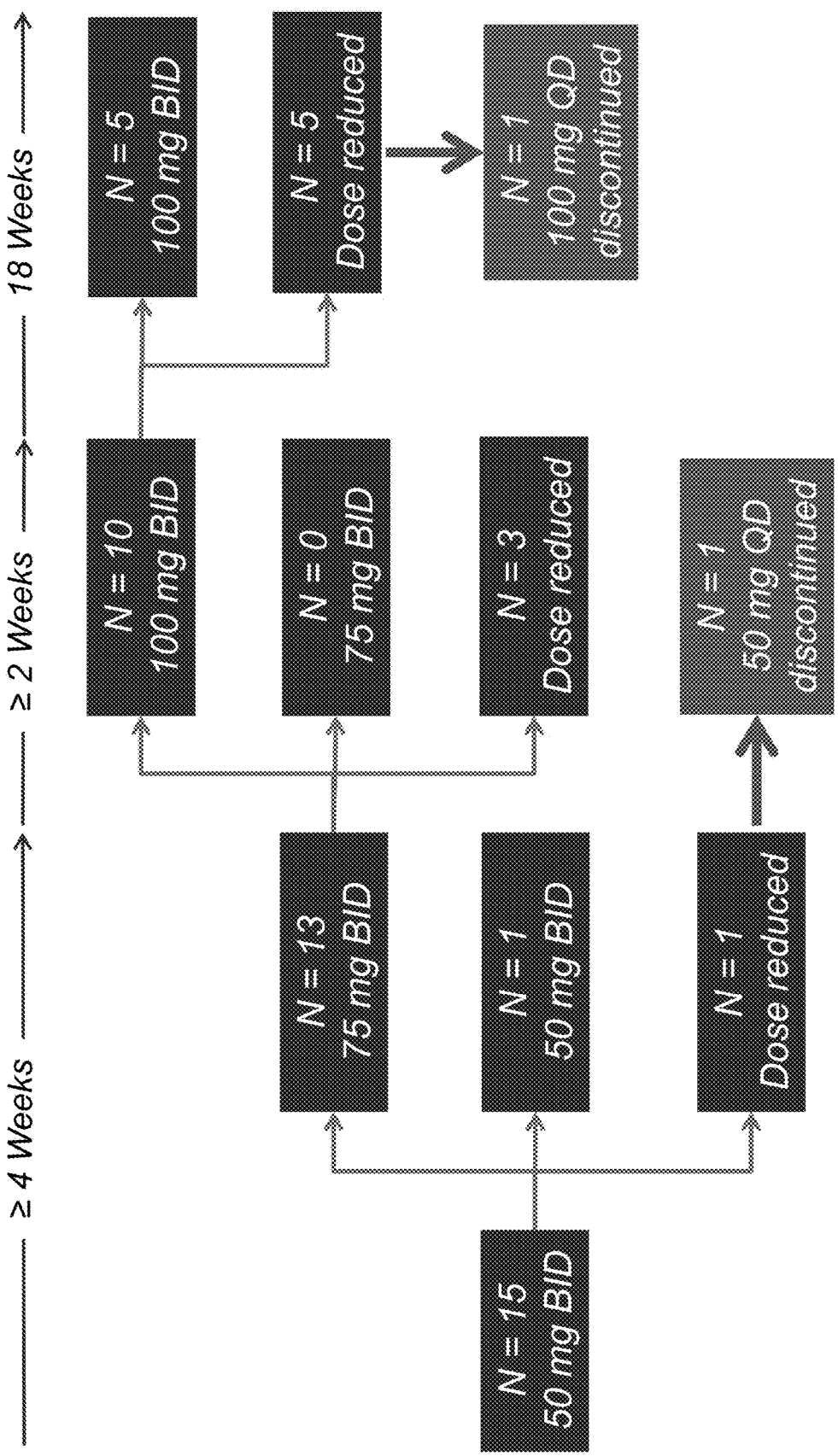
FIG. 22. Dose titration regimen through 24 weeks of treatment for lonafarnib/ritonavir co-therapy as described in Example 14. Ritonavir adjustments are not shown.
Figure 23:
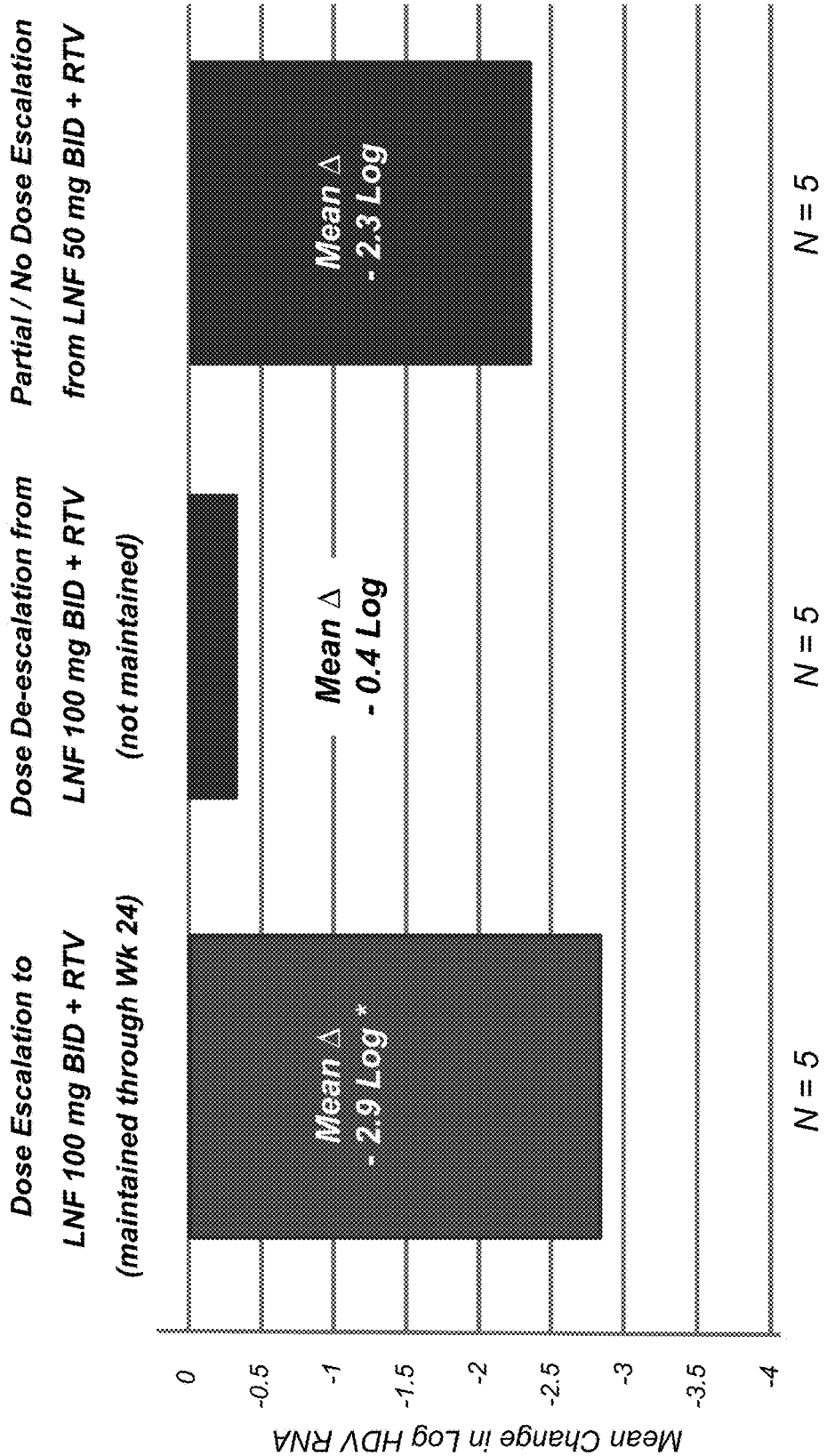
FIG. 23. Changes in HDV RNA viral titers in patients treated with lonafarnib and ritonavir using the combinations, doses, and schedule shown in the figure and described in Example 14.

A schematic of the dose titration regimen through 24 weeks of treatment is shown in FIG. 22. As shown in FIG. 22, after 24 weeks of treatment, 5 of the 15 patients (33%) maintained a dose of 100 mg BID lonafarnib in combination through Week 24 (EOT). The patients who maintained the dose of 100 mg BID lonafarnib in combination with ritonavir exhibited a mean decline in HDV RNA viral load from BL to Week 24 of 2.9 $\log_{10}$ IU/mL. See FIG. 23. Of these 5 patients, one patient (patient 3) achieved HDV-RNA negativity at Week 24, and one patient reduced HDV-RNA viral load to 32 IU/mL (i.e., 1.5 $\log_{10}$ IU/mL) at Week 24 (the lower limit of detection is 14 IU/mL). See FIG. 24.

Of the 10 patients who were dose-escalated to 100 mg BID lonafarnib in combination with ritonavir by Week 8 of treatment, 5 patients were de-escalated to a lower dose. See FIG. 23. These patients exhibited a lower decline in HDV-RNA viral load than patients who maintained the dose of 100 mg BID lonafarnib in combination with ritonavir through Week 24. The remaining 5 patients, who received either a "partial" dose escalation (patient was not successfully escalated to 100 mg lonafarnib BID) or no dose escalation from 50 mg BID lonafarnib in combination with ritonavir, exhibited a mean decline in HDV RNA viral load from BL to Week 24 of 2.3 $\log_{10}$ IU/mL.

Figure 25:
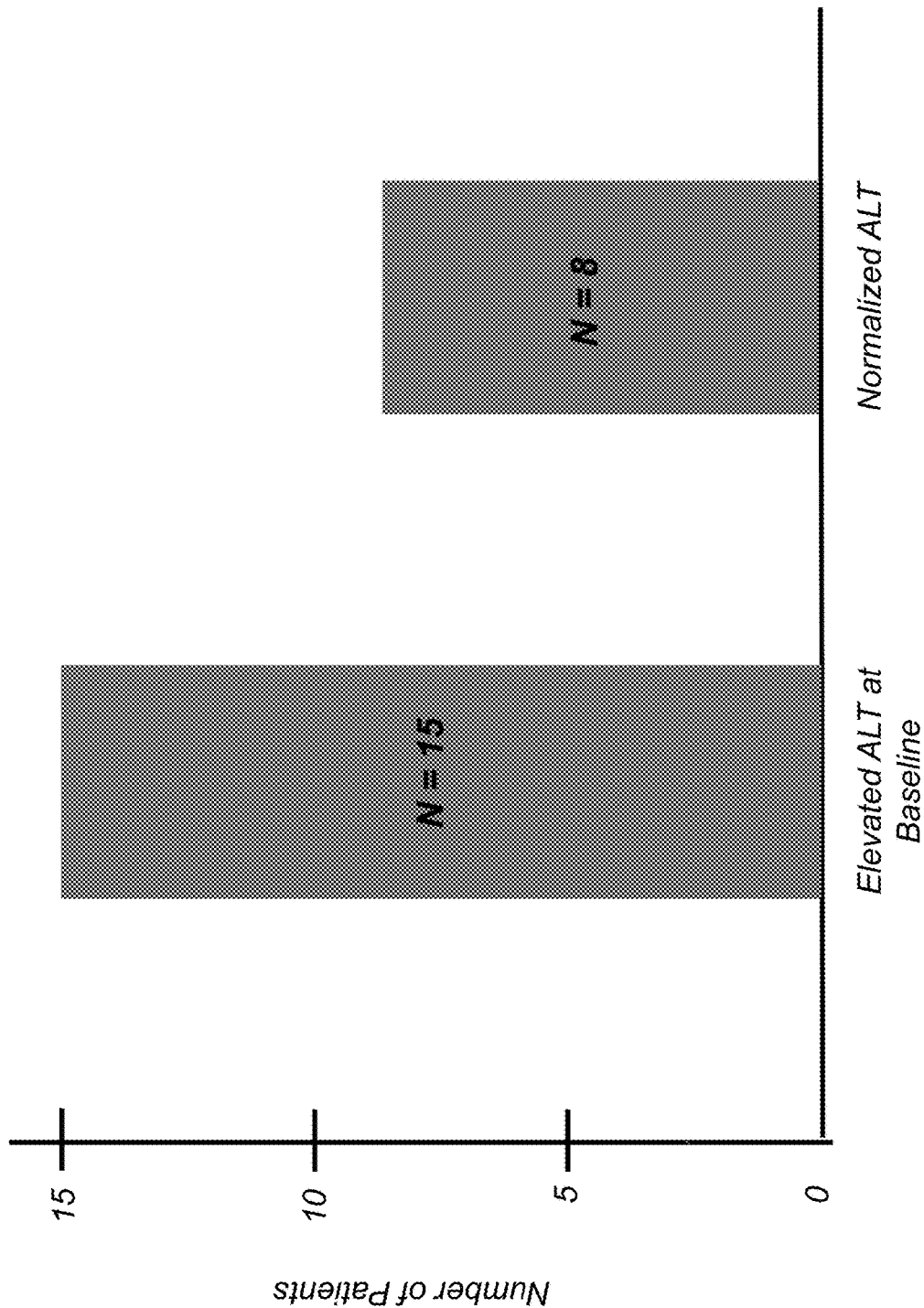
FIG. 25. Changes in ALT values at week 24 of treatment as described in Example 14.

Normalization of ALT values was observed for 53% of patients at week 24. As shown in FIG. 25, all 15 patients had elevated ALT values at baseline, but only 7 patients had elevated ALT values at week 24. Patients experienced predominantly grade 1-2 GI adverse events, as shown in Table 18 below. Table 18 shows the number of patients experiencing a particular grade of GI AE at least once during the 24-week study. The most common AE was intermittent diarrhea, grades 1-2. No grade 4 AEs were observed.

TABLE 18

| Adverse Event | Grade 1 | Grade 2 | Grade 3 | Grade 4 |
|---|---|---|---|---|
| Nausea | 7 | 6 | 0 | 0 |
| Diarrhea | 15 | 7 | 2 | 0 |
| Asthenia | 3 | 3 | 1 | 0 |
| Anorexia | 7 | 6 | 0 | 0 |
| Weight Loss | 8 | 5 | 0 | 0 |
| Vomiting | 4 | 1 | 0 | 0 |

Example 15. Induction of Post-Treatment ALT Flares with Lonafarnib Therapy

This example describes post-treatment ALT flares and their outcomes in patients treated with 12 or 24 weeks of lonafarnib in various treatment regimens, such as the regimens described in Example 12 above. Twenty-seven (27) patients were analyzed who had detectable HDV RNA after receiving lonafarnib for 12 or 24 weeks at various doses of lonafarnib, in some cases in combination with ritonavir and/or pegylated interferon alpha. A post-treatment ALT flare was defined as elevation of ALT to >2× baseline ALT level.

Figure 26:
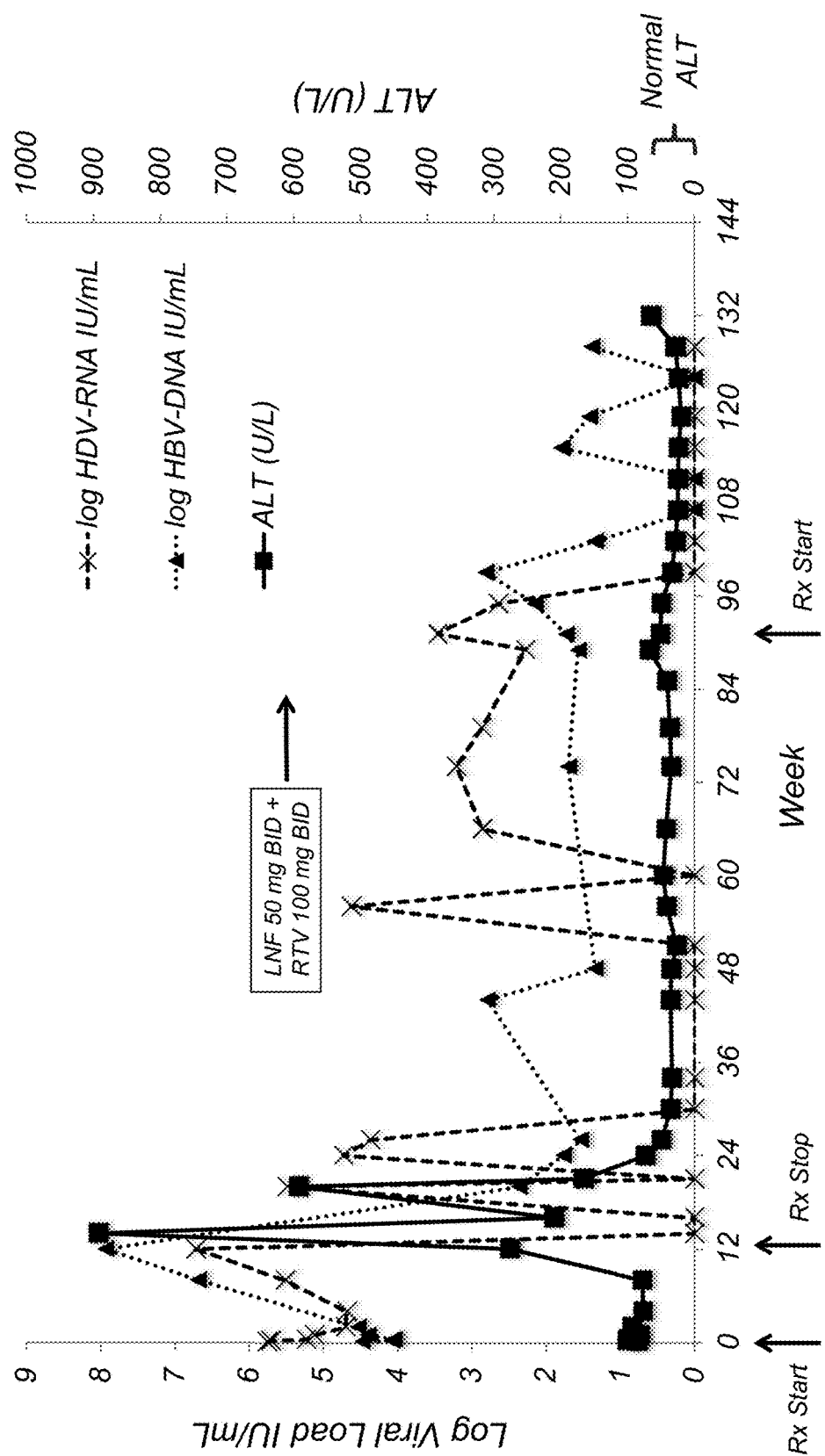
FIG. 26. Post-treatment ALT flare in patient A-001-5 treated with 200 mg BID lonafarnib as described in Example 15, showing HDV-RNA negativity and ALT normalization following ALT flare and suppression of HDV RNA and HBV DNA.
Figure 27:
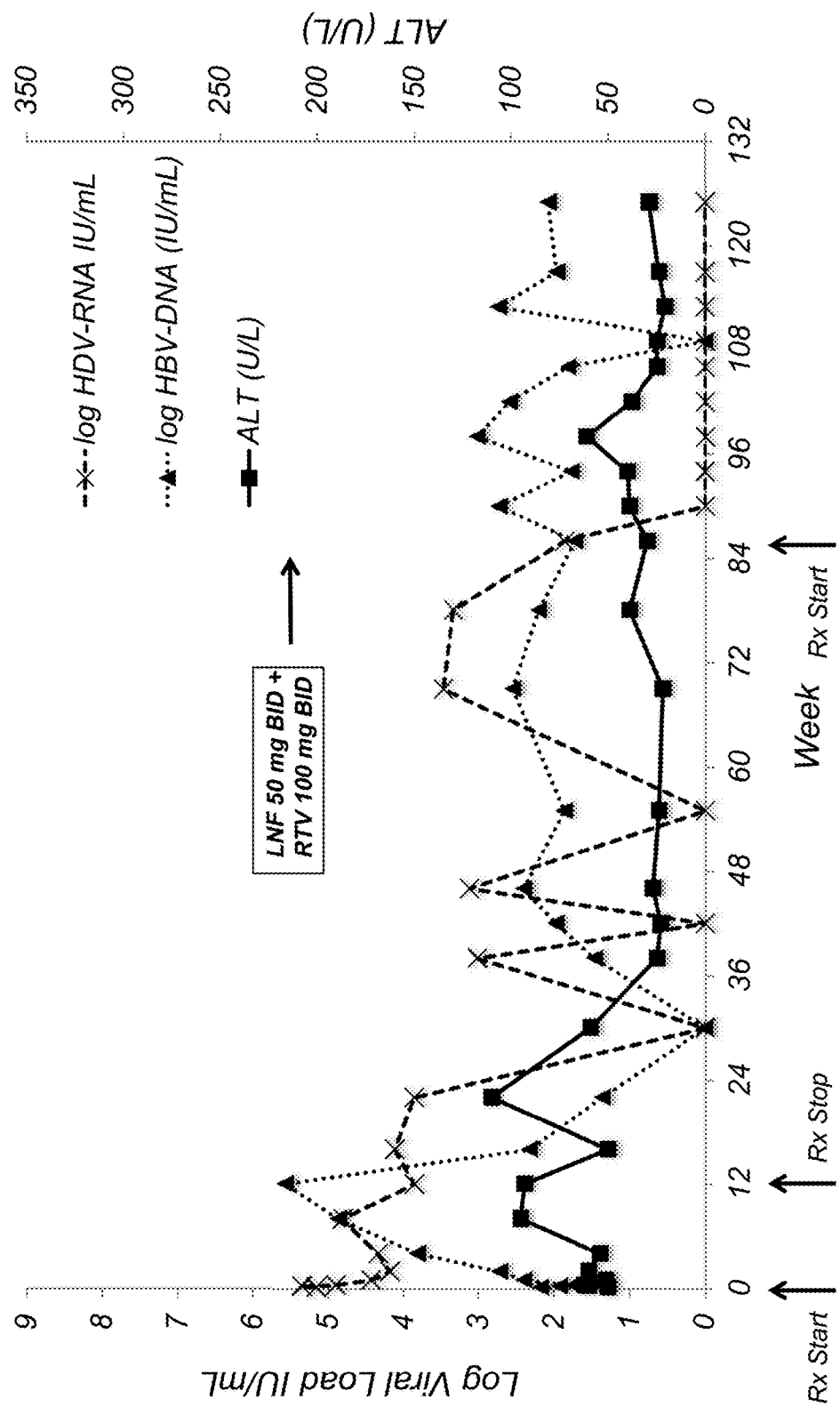
Figure 28:
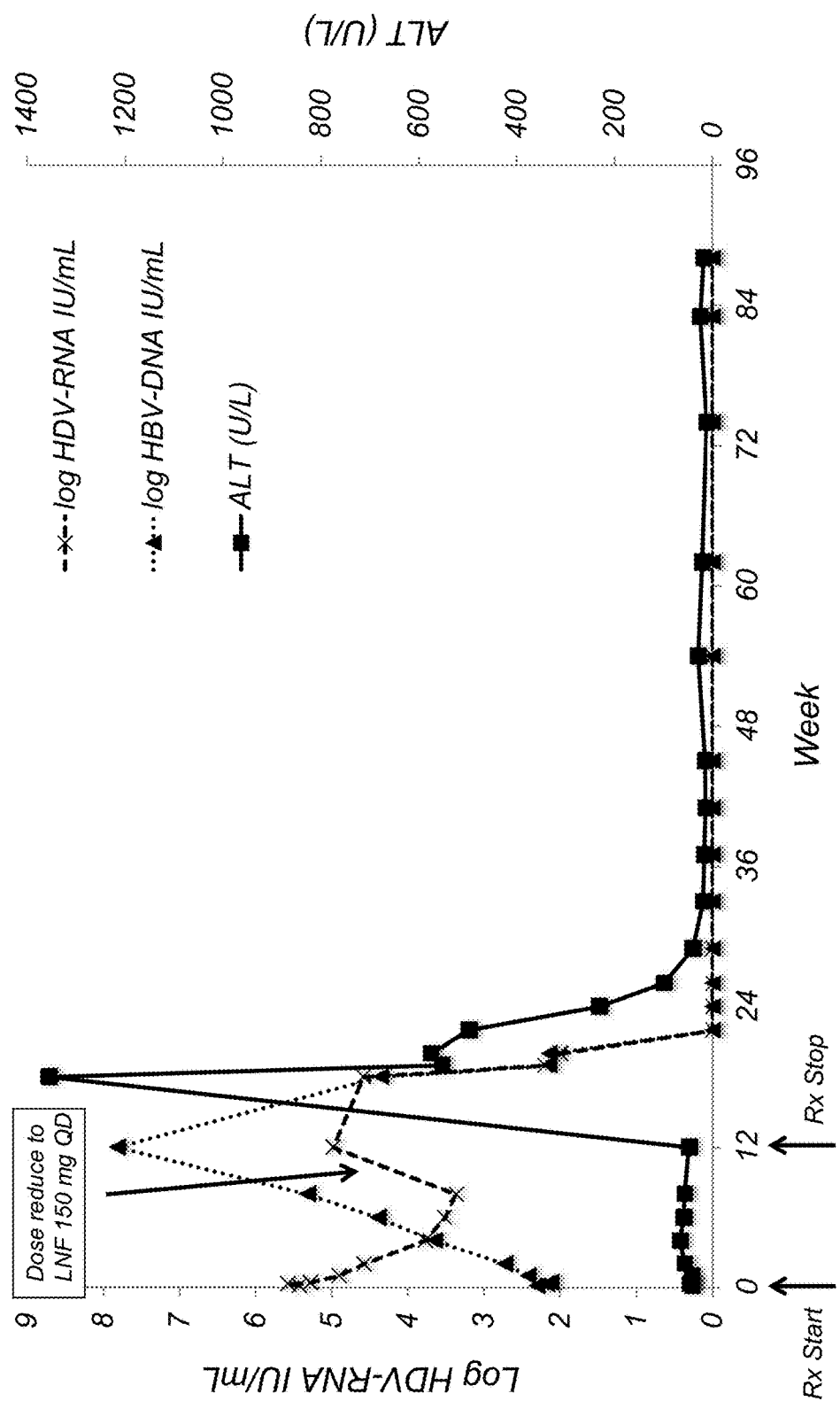

To date, 5 of 27 (18.5%) patients studied have experienced post-treatment ALT flares. These post-treatment flares (median ALT 190 U/L, range 110-1355 U/L) led to ALT normalization and HDV RNA negativity within 12-24 weeks. These 5 patients came from the following lonafarnib treatment cohorts:

Patient A-001-5. 200 mg BID lonafarnib administered for 12 weeks (FIG. 26);
Patient A-001-1. 300 mg BID lonafarnib administered for 12 weeks (FIG. 27);
Patient A-002-3. 100 mg BID lonafarnib in combination with 50 mg BID ritonavir administered for 12 weeks (FIG. 28);
Patient A-002-14. 75 mg BID lonafarnib in combination with 100 mg BID ritonavir administered for 12 weeks, followed by addition of pegylated interferon alpha for 12 weeks (FIG. 29); and
Patient A-002-23. 50 mg BID lonafarnib in combination with 100 mg BID ritonavir administered for 24 weeks (FIG. 30).

One patient (patient A-002-3) cleared HBV DNA and subsequently cleared HBsAg. See FIG. 28. Two other patients (patient A-001-5 and patient A-002-23) exhibited declines in HBV DNA of 2 logs or greater. See FIG. 26 and FIG. 30. All 5 patients exhibited rapid initial declines of HDV RNA upon initiation of lonafarnib treatment; these rapid initial declines were eventually followed by more gradual rises upon therapy associated with decreased lonafarnib exposure (due to dose reductions or excessive GI side effects).

As illustrated in FIG. 26 in Patient A-001-5, a 12-week course of treatment with lonafarnib (200 mg BID) resulted in an ALT flare and a suppression of HDV RNA to undetectable levels. A subsequent rise in HDV viral load (at about week 50) was suppressed by a second course of treatment with lonafarnib (50 mg BID) and ritonavir (100 mg BID). As shown in FIG. 26, HDV become undetectable in this patient and the patient remained apparently virus-free when measured at 132 weeks. Surprisingly, HBV VL (i.e., HBV DNA level) was also suppressed from a baseline of about 4 log IU/mL to approximately 1.5 log IU/mL (i.e., below than the LOQ). See FIG. 26.

As illustrated in FIG. 27 in Patient A-001-1, a 12-week course of treatment with lonafarnib (300 mg BID) resulted in an ALT flare and a suppression of HDV RNA below about 3 logs (weeks 30-54). A rise in HDV VL was observed (e.g., week 78), and was suppressed by a second course of treatment with low dose lonafarnib therapy (50 mg BID) and ritonavir (100 mg BID). The transient rise in HBV DNA level was also suppressed following the ALT flare. The patient remained apparently virus-free when measured at 125 weeks.

As illustrated in FIG. 28 in Patient A-002-3, treatment with lonafarnib (100 mg BID) and ritonavir (50 mg BID) for about 10 weeks followed by lonafarnib (150 mg QD) and ritonavir (50 mg BID) for 2 weeks resulted in an ALT flare. HDV RNA and HBV DNA levels dropped to undetectable levels. The patient remained apparently virus-free when measured at 95 weeks.

Figure 29:
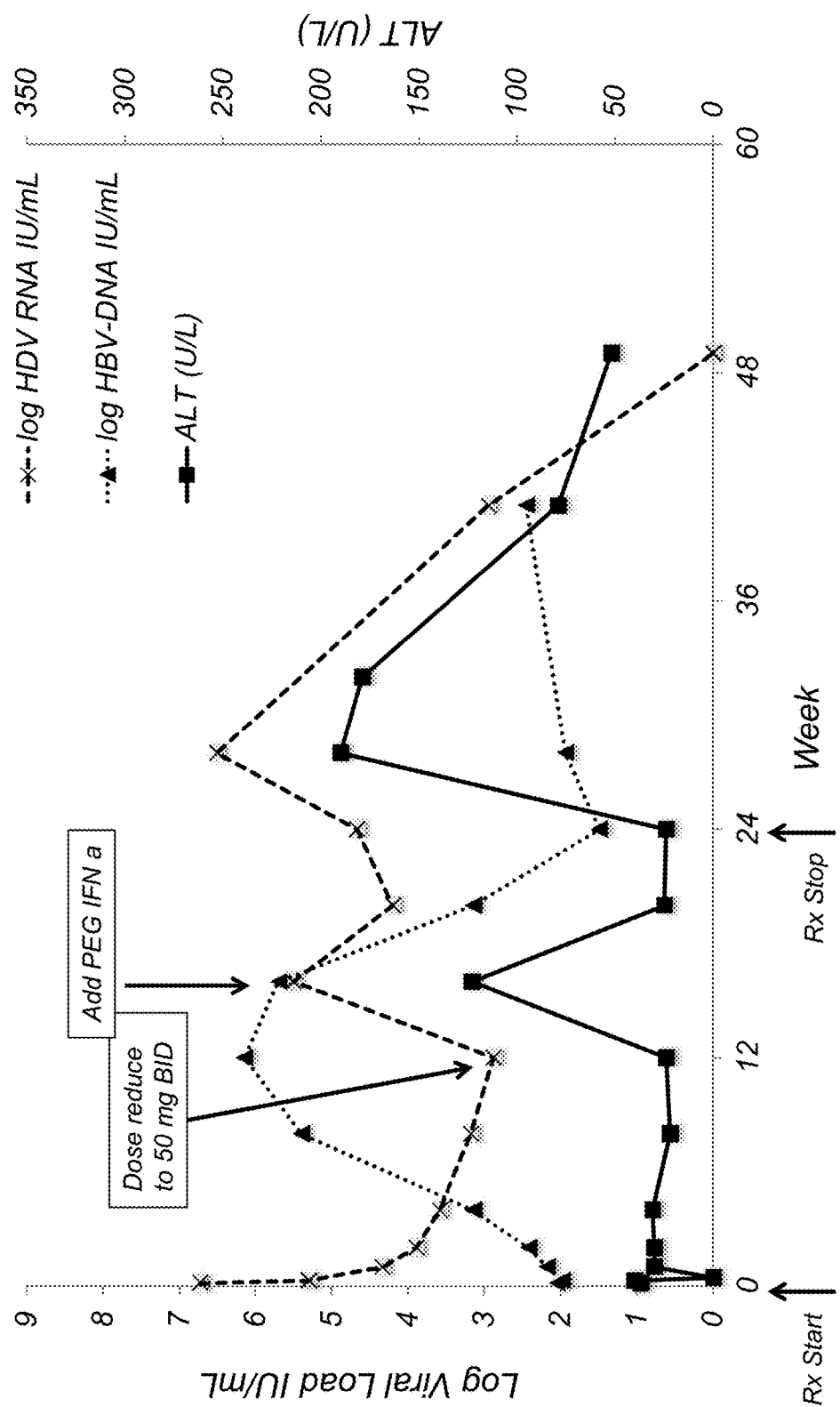
Figure 30:
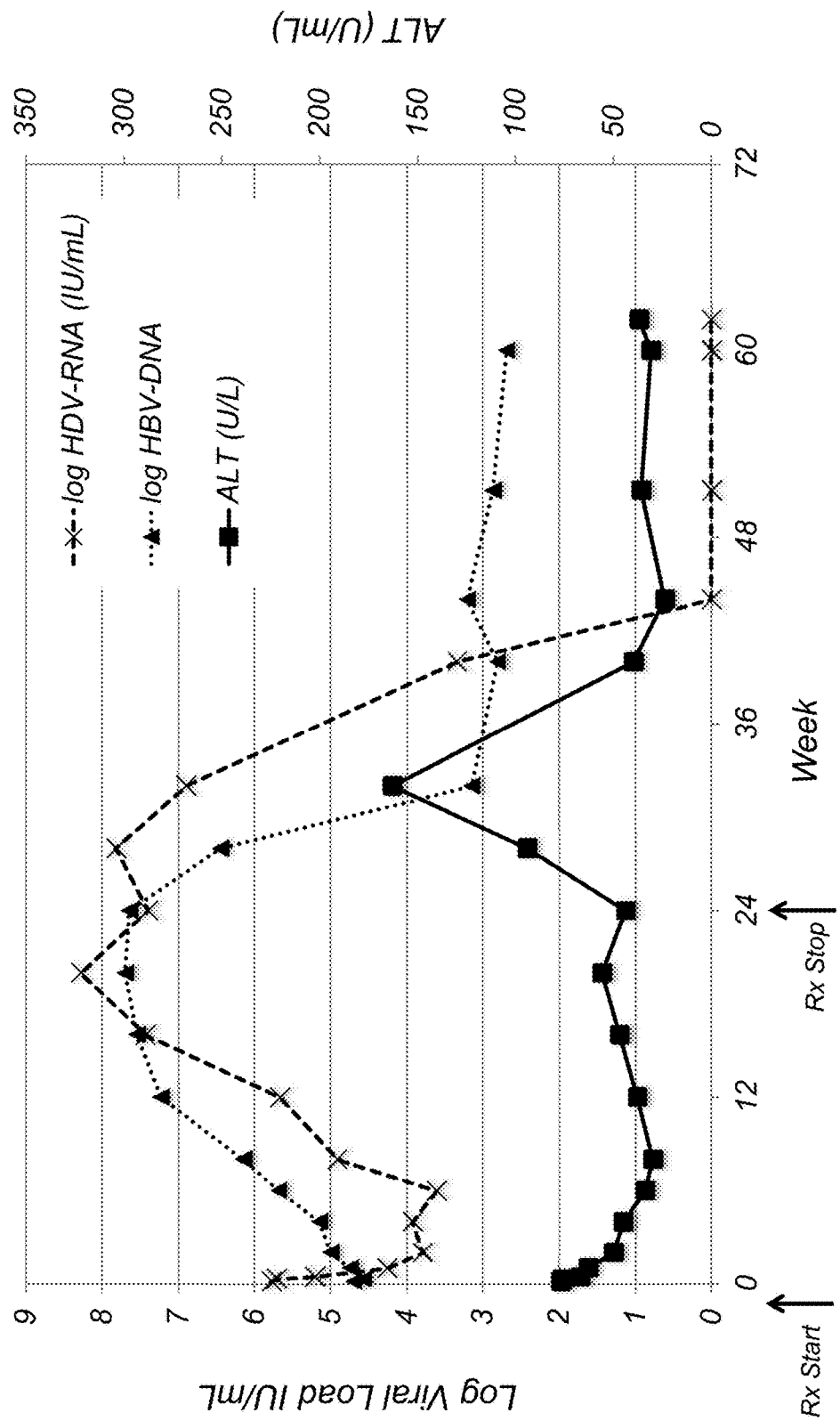

As illustrated in FIG. 29 in Patient A-002-14, a 24-week course of treatment with lonafarnib, ritonavir and pegylated interferon alpha as shown in the figure resulted in an ALT flare and the suppression of HDV RNA VL from greater than 6 log IU/mL to below the limit of quantitation for the assay (i.e., less than 3.2 log IU/mL).

As illustrated in FIG. 30 in Patient A-002-23, a 24-week course of treatment with lonafarnib (50 mg BID) and ritonavir (100 mg BID) resulted in an ALT flare and a suppression of HDV RNA to approximately 0 log IU/mL.

The data presented herein suggest that a short course of lonafarnib may contribute to an effective reset and activation of the immune reactivity in chronic delta hepatitis, which surprisingly in some cases may spread to HBV. Thus, there appear to be at least two pathways for achieving HDV negativity with lonafarnib therapy: first, lonafarnib-induced progressive suppression to HDV negativity with ALT normalization during the course of treatment (a more classical anti-viral approach), and second, lonafarnib-induced anti-HDV ALT flares that occur post-treatment and result in HDV clearance.

Example 16. Preparation of Lonafarnib-Ritonavir-Copolymer Compositions (A) 1:1:2 Co-Precipitate
5.0 gram of ritonavir, 5.47 gram of lonafarnib, and 10.0 gram of Povidone K30 were dissolved in 600 mL of dichloromethane by stirring at room temperature. The solution was spray dried using a Model GB22 Yamato Lab Spray Dryer with the following operating parameters: internal nozzle diameter 711 µm; pump rate 12-14 mL/min; inlet temperature 60° C.; outlet temperature NMT 45° C.; atomization air pressure 0.15 MPa and air flow 0.5 m$^3$/min. For 20.47 g of solids in the spray solution, 15.9 g were collected in the receiving flask for a yield of 77%. The total solids in the spray solution was 3% (w/v).

(B) 1:2:3 Co-Precipitate
6.5 gram of the ritonavir-lonafarnib-povidone (1:1:2) co-precipitate of (A) (which corresponds to 1.6 gram of ritonavir, 1.6 gram lonafarnib, and 3.3 gram of povidone K30), an additional 1.6 gram of ritonavir (for a total quantity of ritonavir of 3.2 gram), and an additional 1.5 gram of povidone K30 (for a total quantity of povidone K30 of 4.8 gram) were dissolved in 300 mL of dichloromethane by stirring at room temperature. The solution was spray dried using a Model GB22 Yamato Lab Spray Dryer with the following operating parameters: internal nozzle diameter 711 µm; pump rate 12-14 mL/min; inlet temperature 60° C.; outlet temperature NMT 45° C.; atomization air pressure 0.15 MPa and air flow 0.5 m³/min. For 9.6 g of solids in the spray solution, 5.6 g were collected in the receiving flask for a yield of 58%. The total solids in the spray solution was 3% (w/v).

(C) 1:1:5 Co-Precipitate 7.5 gram of the ritonavir-lonafarnib-povidone (1:1:2) co-precipitate of (A) (which corresponds to 1.9 gram of ritonavir, 1.9 gram lonafarnib, and 3.8 gram of povidone K30), and an additional 5.0 gram of povidone K30 (for a total quantity of povidone K30 of 8.8 gram) were dissolved in 390 mL of dichloromethane by stirring at room temperature. The solution was spray dried using a Model GB22 Yamato Lab Spray Dryer with the following operating parameters: internal nozzle diameter 711 μm; pump rate 12-14 mL/min; inlet temperature 60° C.; outlet temperature NMT 45° C.; atomization air pressure 0.15 MPa and air flow 0.5 m³/min. For 12.5 g of solids in the spray solution, 8.8 g were collected in the receiving flask for a yield of 70%. The total solids in the spray solution was 3% (w/v).

(D) 1:1:2 Co-Precipitate with HPMC Polymer 2.5 gram of ritonavir, 2.61 gram of lonafarnib, and 5.0 gram of hydroxymethylcellulose (HPMC) were dissolved in 340 mL of dichloromethane by stirring at room temperature. The solution was spray dried using a Model GB22 Yamato Lab Spray Dryer with the following operating parameters: internal nozzle diameter 711 μm; pump rate 12-14 mL/min; inlet temperature 60° C.; outlet temperature NMT 45° C.; atomization air pressure 0.15 MPa and air flow 0.5 m³/min. For 10.1 g of solids in the spray solution, 7.2 g were collected in the receiving flask for a yield of 71%. The total solids in the spray solution was 3% (w/v).

Analysis of Lonafarnib-Ritonavir-Copolymer Compositions

Figure 31:
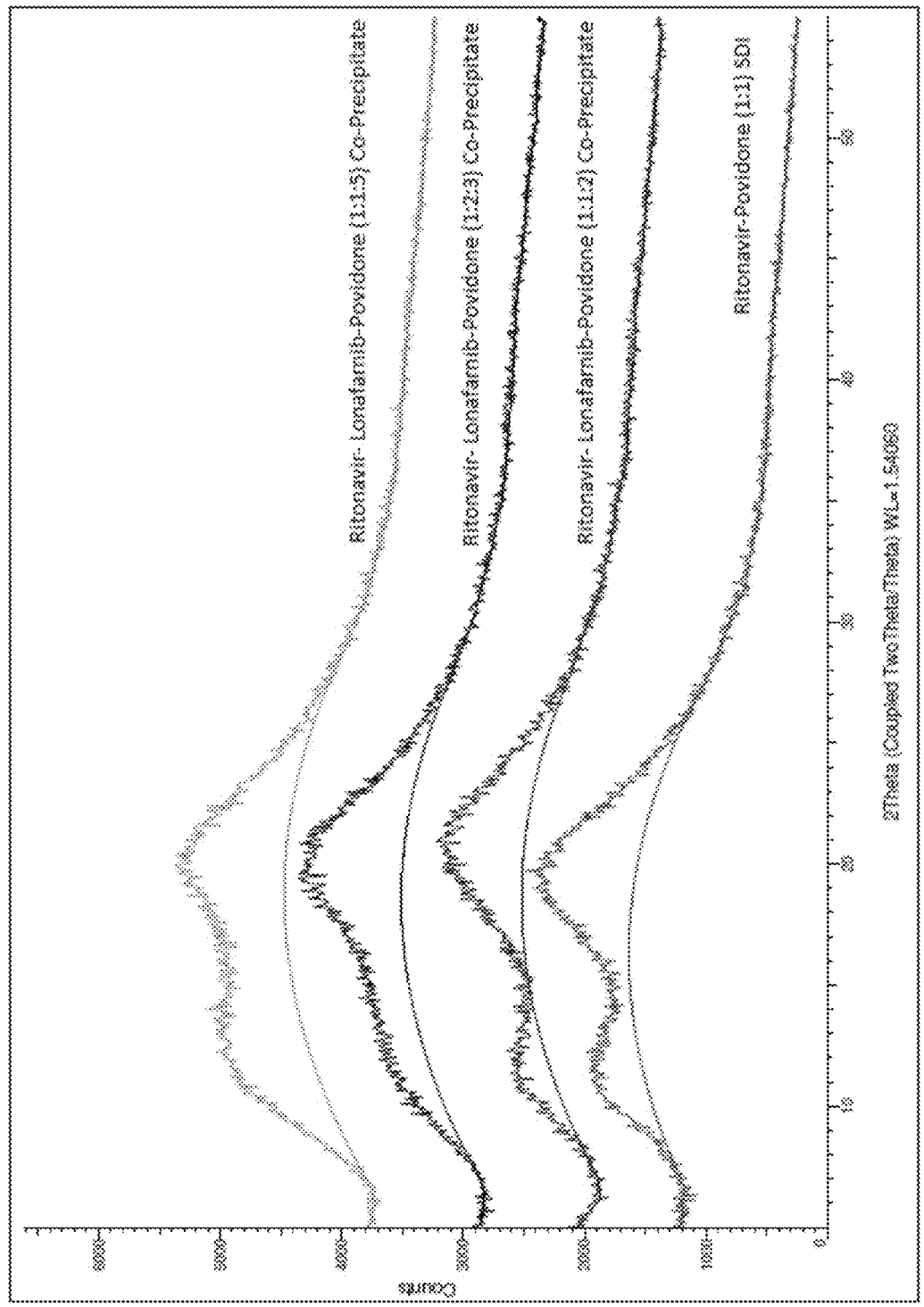
FIG. 31. Characteristic powder X-ray diffraction (XRPD) patterns of ritonavir-lonafarnib-povidone compositions at ratios of 1:1:2 (w/w), 1:2:3 (w/w), and 1:1:5 (w/w), prepared as described in Example 16.

The amorphous state of each co-precipitate of (A)-(D) was verified by X-ray powder diffraction (XRPD). The diffraction pattern was verified by X-ray diffraction using a Bruker D2 Phaser X-ray diffractometer with Lynxeye detector, Cu Kα radiation (λ=1.5406 Å). Acquisition was done over a range of 5-55° 2θ, increment of 0.05° 2θ, 1.0 s step time and 0.6 mm opening slit and a 2.5 mm detector windows. The samples were analyzed using a low volume sample holder and kept under a constant rotation of 15 rpm during the analysis. FIG. 31 is a powder X-ray pattern of the amorphous 1:1:2, 1:2:3, and 1:1:5 ritonavir-lonafarnib-copolymer co-precipitates with povidone as the co-polymer. Consistent with the characteristic of amorphous solid form, the amorphous 1:1:2, 1:2:3, and 1:1:5 co-precipitates do not exhibit crystalline diffraction peaks. The amorphous 1:1:2 co-precipitate with HPMC also does not exhibit crystalline diffraction peaks (data not shown).

Residual solvent from spray-dried material was verified by thermogravimetric analysis (TGA). The analysis was performed using a TA Instrument Q50 thermogravimetric analyzer at scanning speed of 10° C. min⁻¹ over a temperature range of 25 to 200° C. The samples were heated in a platinum open pan under nitrogen purge (60 mL min⁻¹).

Figure 32A:
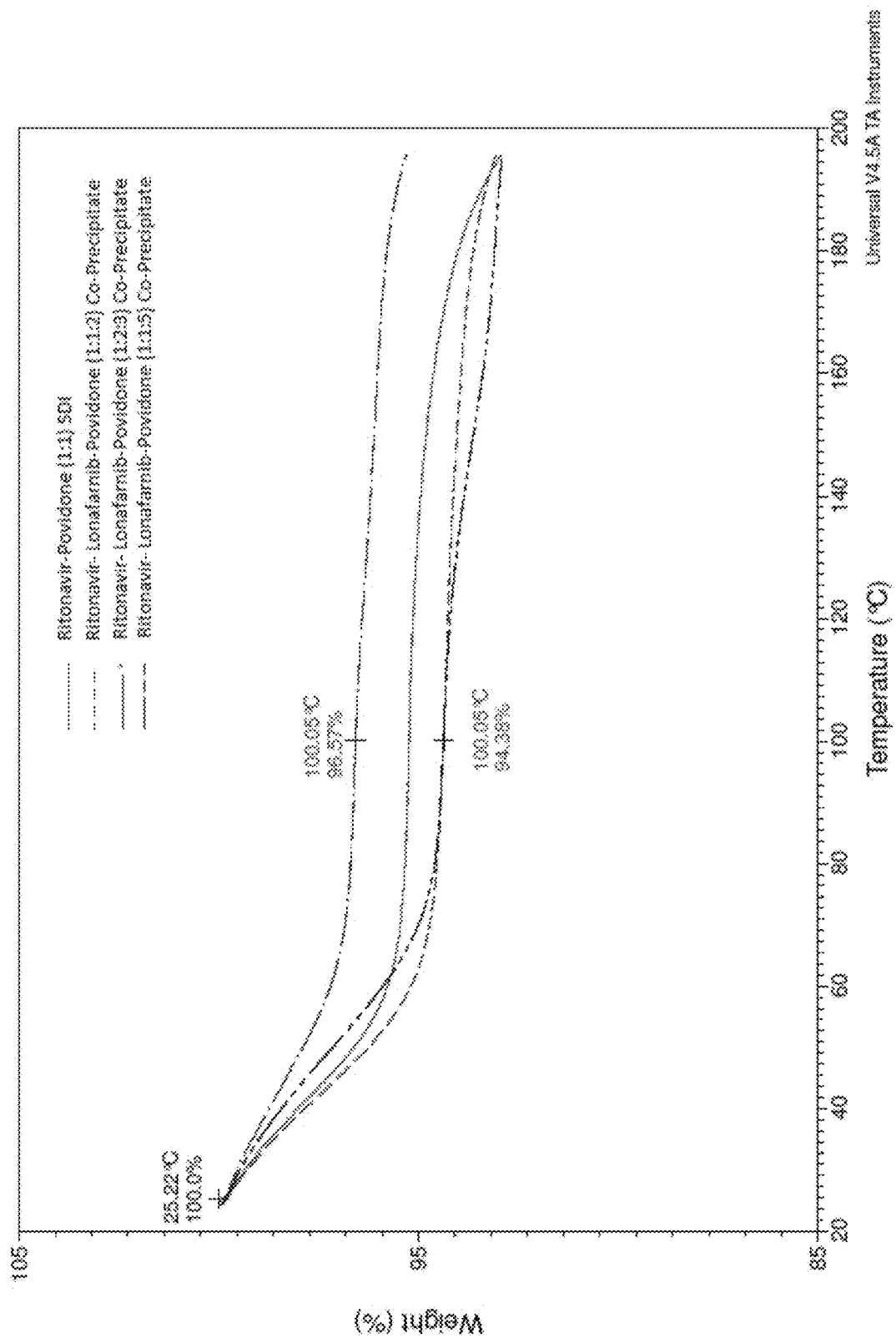
FIG. 32A-32B. Thermogravimetric analysis (TGA). (A) Characteristic powder TGA thermogram of ritonavir-povidone (1:1) and ritonavir-lonafarnib-povidone (1:1:2), (1:2:3), and (1:1:5) co-precipitates prepared as described in Example 16. (B) Characteristic powder TGA thermogram comparing ritonavir-lonafarnib-povidone (1:1:2) and ritonavir-lonafarnib-HPMC (1:1:2) co-precipitates prepared as described in Example 16.

FIG. 32A illustrates the sample weight (in percent of original weight) as a function of temperature. This material exhibited distinct weight-loss steps. The first step (weight loss 4.8-5.6%) at temperatures between 25 and 100° C. corresponds to loss of volatile compounds (water and dichloromethane) followed by material decomposition initiated at approximately 180° C. Identification and quantification of residual solvents using more sophisticated techniques such gas chromatography should be employed to ensure compliance with ICH Q3C guidelines.

Figure 32B:
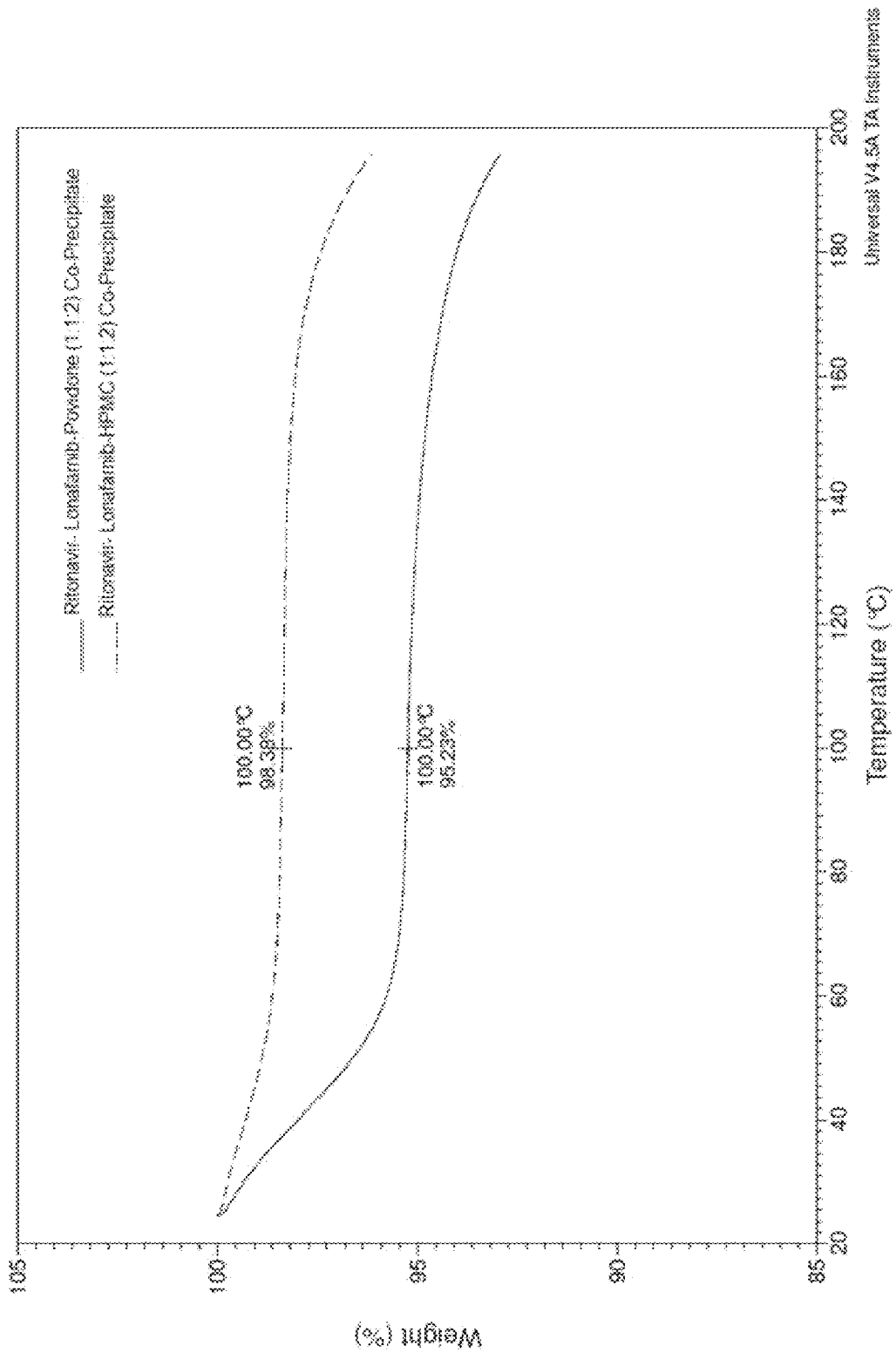

FIG. 32B compares samples with similar API (active pharmaceutical ingredient) compositions but different polymers, a 1:1:2 ritonavir-lonafarnib-povidone containing sample and a 1:1:2 ritonavir-lonafarnib-HPMC containing sample. As shown in FIG. 23B, the HPMC-containing sample contains 1.7% of volatiles, much lower compared to the povidone-containing sample at 4.8%. This difference is likely linked to higher hygroscopicity and/or dichloromethane affinity of povidone versus HPMC.

Example 17. Exemplary Co-Therapy Dosages

For illustration and not limitation, this example provides exemplary doses for lonafarnib-ritonavir co-therapy and for lonafarnib-interferon lambda co-therapy. For lonafarnib-ritonavir co-therapy, exemplary doses include the following combinations (with reference to Table 19): L1+(R1 or R2 or R3), where L1 and R are from the same row.

TABLE 19

| L1 | R1 | R2 | R3 |
|---|---|---|---|
| 25 BID | 50 BID | 75 BID | 100 BID |
| 50 BID | 50 BID | 75 BID | 100 BID |
| 75 BID | 50 BID | 75 BID | 100 BID |
| 100 BID | 50 BID | 75 BID | 100 BID |
| 50 QD | 50 QD | 75 QD | 100 QD |
| 75 QD | 50 QD | 75 QD | 100 QD |
| 100 QD | 50 QD | 75 QD | 100 QD |
| 50 QD | 50 BID | 75 BID | 100 BID |
| 75 QD | 50 BID | 75 BID | 100 BID |
| 100 QD | 50 BID | 75 BID | 100 BID |

For lonafarnib-interferon lambda co-therapy, exemplary doses, for illustration and not limitation, include the following combinations (with reference to Table 20):

TABLE 20

| Lonafarnib dose | Interferon lambda dose |
|---|---|
| 50 mg BID | 120 mcg QW |
| 75 mg BID | 120 mcg QW |
| 100 mg BID | 120 mcg QW |

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

It should be understood that although the present invention has been specifically disclosed by certain aspects, embodiments, and optional features, modification, improvement and variation of such aspects, embodiments, and optional features can be resorted to by those skilled in the art, and that such modifications, improvements and variations are considered to be within the scope of this disclosure.

The inventions have been described broadly and generically herein. Each of the narrower species and subgeneric groupings falling within the generic disclosure also form part of the invention. In addition, where features or aspects of the invention are described in terms of Markush groups, those skilled in the art will recognize that the invention is also thereby described in terms of any individual member or subgroup of members of the Markush group.

What is claimed is:

1. A method for inducing immune reactivation in a patient infected with hepatitis delta virus (HDV) and hepatitis B virus (HBV), the method comprising:
   (i) administering lonafarnib and ritonavir co-therapy to the patient, wherein the lonafarnib is administered at a dose of 25 mg BID or 50 mg BID and the ritonavir is administered at a dose of 100 mg BID to 200 mg BID; and
   (ii) detecting a hepatitis flare in the patient.

2. The method of claim 1, wherein the detecting step comprises measuring serum alanine aminotransferase (ALT) levels in the patient.

3. The method of claim 1, wherein the lonafarnib and ritonavir co-therapy is administered for a period of 2 to 12 weeks.

4. The method of claim 1, wherein the method further comprises administering an interferon to the patient.

5. The method of claim 4, wherein the interferon is administered at a dose of 120 micrograms QW or 180 micrograms QW.

6. The method of claim 4, wherein the interferon is interferon lambda.

7. A method for inducing immune reactivation in a patient infected with HDV and HBV, the method comprising administering to the patient lonafarnib at a first dose, followed by administering lonafarnib at a second dose, wherein the second dose is lower than the first dose.

8. The method of claim 7, wherein the first dose is administered for at least 8 weeks and the second dose is administered for at least 4 weeks.

9. The method of claim 7, wherein the first dose of lonafarnib is 50 mg BID and the second dose of lonafarnib is 25 mg BID.

10. A method for inducing immune reactivation in a patient infected with hepatitis delta virus (HDV) comprising:
   administering lonafarnib-ritonavir co-therapy to the patient, wherein the lonafarnib is administered at a dose of 25 mg BID to 75 mg BID and the ritonavir is administered at a dose of 100 mg BID to 200 mg BID; and wherein the patient experiences a serum alanine aminotransferase (ALT) flare of over 5 fold the upper limit of normal (ULN) during treatment.

11. The method of claim 10, wherein the patient experiences a decrease in HDV RNA levels of at least 1 log before experiencing an increase in HDV RNA levels of at least 50% or more from the nadir during treatment.

12. The method of claim 10, wherein the patient is also infected with hepatitis B virus (HBV) and experiences a transient increase of at least 3 log in HBV viral load.

13. The method of claim 10, wherein the patient has improved liver function during or after treatment.

14. The method of claim 13, wherein improvement in liver function is an improvement in one or more of serum albumin, bilirubin, ALT, aspartate aminotransferase (AST), or prothrombin activity by at least 10%, by at least 20%, or by at least 30%.

15. The method of claim 10, wherein during or after treatment the patient has improved liver biopsy as assessed by one or more of the following: histological staining, immunohistochemical staining, and fibrosis grading.

16. The method of claim 10, wherein the patient has a delay in the need for a liver transplant for at least 3 months.

17. The method of claim 10, wherein the serum lonafarnib concentration is greater than 2,000 ng/mL or greater than 4,000 ng/mL, or in a range from 3,500 ng/mL to about 7,500 ng/mL.

18. The method of claim 10, wherein the patient has a baseline viral load of at least $10^4$ HDV RNA copies per mL serum.

19. The method of claim 10, wherein the patient has a baseline ALT level that is at least two fold higher than the ULN.

20. The method of claim 10, wherein the patient experiences a sustained reduction in HDV RNA levels for a least one month.

* * * * *